United States Patent
Wempe et al.

(10) Patent No.: US 10,005,750 B2
(45) Date of Patent: Jun. 26, 2018

(54) DEVELOPING POTENT URATE TRANSPORTER INHIBITORS: COMPOUNDS DESIGNED FOR THEIR URICOSURIC ACTION

(75) Inventors: Michael F. Wempe, Aurora, CO (US); Hitoshi Endou, Tokyo (JP)

(73) Assignee: J-Pharma Co., Ltd., Tokyo (JP)

( * ) Notice: Subject to any disclaimer, the term of this patent is extended or adjusted under 35 U.S.C. 154(b) by 203 days.

(21) Appl. No.: 13/823,522

(22) PCT Filed: Oct. 6, 2011

(86) PCT No.: PCT/US2011/055006
§ 371 (c)(1),
(2), (4) Date: Apr. 29, 2013

(87) PCT Pub. No.: WO2012/048058
PCT Pub. Date: Apr. 12, 2012

(65) Prior Publication Data
US 2013/0225673 A1    Aug. 29, 2013

Related U.S. Application Data

(60) Provisional application No. 61/390,604, filed on Oct. 6, 2010, provisional application No. 61/468,976, filed on Mar. 29, 2011.

(51) Int. Cl.
C07D 307/84 (2006.01)
C07D 209/12 (2006.01)
(Continued)

(52) U.S. Cl.
CPC ......... *C07D 307/84* (2013.01); *C07D 209/12* (2013.01); *C07D 307/79* (2013.01); *C07D 307/80* (2013.01)

(58) Field of Classification Search
CPC .. C07D 209/12; C07D 307/79; C07D 307/80; C07D 307/84
(Continued)

(56) References Cited

U.S. PATENT DOCUMENTS 3,012,042 A   12/1961 Hoi et al.
3,853,923 A   12/1974 Ito et al.
(Continued)

FOREIGN PATENT DOCUMENTS

DE    3342624 A1    3/1984
DE    19624292 A1   1/1998
(Continued)

OTHER PUBLICATIONS

CN101658519, English translation, Mar. 3, 2010.*
(Continued)

*Primary Examiner* — Umamaheswari Ramachandran
(74) *Attorney, Agent, or Firm* — Osha Liang LLP

(57) ABSTRACT

A compound represented by the general Formula I:

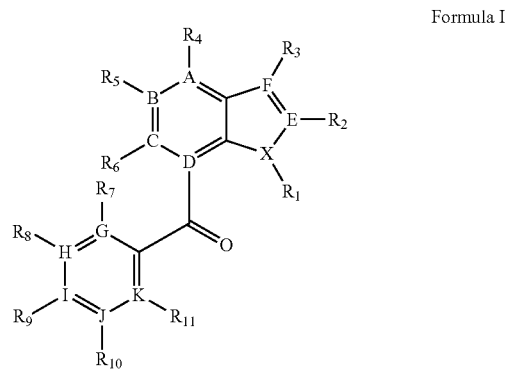

Formula I a pharmaceutically acceptable salt or ester thereof, a solvate thereof, a chelate thereof, a non-covalent complex thereof, a pro-drug thereof, a deuterated radiolabeled analog thereof, and mixtures of any of the foregoing, wherein: A-K are individually selected from carbon or nitrogen; X=—O, —NR$_1$, or —S; R$_{1-11}$ are individually selected from the group consisting of —H, C$_1$-C$_6$ alkyl, C$_6$-C$_{14}$ aryl, substituted C$_6$-C$_{14}$ aryl, C$_1$-C$_{14}$-alkoxy, halogen, hydroxyl, carboxy, cyano, C$_1$-C$_6$-alkanoyloxy, C$_1$-C$_6$-alkylthio, C$_1$-C$_6$-alkylsulfonyl, trifluoromethyl, hydroxy, C$_2$-C$_6$-alkoxycarbonyl, C$_2$-C$_6$-alkanoylamino, —O—R$_{12}$, S—R$_{12}$, —SO$_2$—R$_{12}$, —NHSO$_2$R$_{12}$ and —NHCO$_2$R$_{12}$, wherein R$_{12}$ is phenyl, naphthyl, or phenyl or naphthly substituted with one to three groups selected from C$_1$-C$_6$-alkyl, C$_6$-C$_{10}$ aryl, C$_1$-C$_6$-alkoxy and halogen, and C$_4$-C$_{20}$ hydroxyheteroaryl wherein the heteroatoms are selected from the group consisting of sulfur, nitrogen, and oxygen.

10 Claims, 17 Drawing Sheets

(51) Int. Cl.
  *C07D 307/79*  (2006.01)
  *C07D 307/80*  (2006.01)
(58) Field of Classification Search
  USPC .......................................... 514/469; 549/468
  See application file for complete search history.

(56) References Cited

U.S. PATENT DOCUMENTS

| | | | |
|---|---|---|---|
| 3,920,707 | A | 11/1975 | Descamps et al. |
| 3,944,330 | A | 3/1976 | Tsunoda et al. |
| 4,056,626 | A | 11/1977 | Ito et al. |
| 4,117,151 | A | 9/1978 | Descamps et al. |
| 5,266,711 | A | 11/1993 | Boudet et al. |
| 5,380,857 | A | 1/1995 | Roduit et al. |
| 6,103,708 | A | 8/2000 | Dollings et al. |
| 6,348,474 | B1 | 2/2002 | Kayakiri et al. |
| 7,521,570 | B2 | 4/2009 | Endou et al. |
| 2002/0099212 | A1 | 7/2002 | Kayakiri et al. |
| 2004/0180947 | A1 | 9/2004 | Kayakiri et al. |
| 2005/0250820 | A1 | 11/2005 | Chen |
| 2006/0264481 | A1 | 11/2006 | Chen |
| 2010/0004208 | A1 | 1/2010 | Chaplin et al. |
| 2010/0160351 | A1* | 6/2010 | Jenkins et al. ............. 514/262.1 |
| 2012/0214770 | A1 | 8/2012 | Chaplin et al. |
| 2013/0053351 | A1 | 2/2013 | Chaplin et al. |
| 2013/0225673 | A1 | 8/2013 | Wempe et al. |
| 2014/0171642 | A1 | 6/2014 | Chaplin et al. |

FOREIGN PATENT DOCUMENTS

| | | | |
|---|---|---|---|
| EP | 0 399 773 | A1 | 11/1990 |
| GB | 1299247 | A | 12/1972 |
| GB | 1493237 | * | 5/1976 |
| JP | 49-059648 | A | 5/1974 |
| JP | S4959658 | A | 6/1974 |
| JP | S49-69658 | A | 7/1974 |
| JP | 48-075561 | A | 5/1976 |
| JP | S52116446 | A | 9/1977 |
| JP | 59-051275 | | 3/1984 |
| JP | 59-073579 | A | 4/1984 |
| JP | 04/005286 | | 1/1992 |
| JP | 2002-514636 | A | 5/2002 |
| JP | 2007527918 | A | 10/2007 |
| JP | 2009531281 | A | 9/2009 |
| JP | 5844376 | B2 | 1/2016 |
| WO | 98/39323 | A1 | 9/1998 |
| WO | 99000372 | A1 | 1/1999 |
| WO | 2008/019357 | A2 | 2/2008 |

OTHER PUBLICATIONS

Torii Document (Torii Pharmaceuticals, 2004).*
Myung In Pharm (Myung In Pharm, 2008).*
Bundgaard, Design of Prodrugs, 1985, chapter 1.*
Silverman (Prodrugs and Drug Delivery Systems, The Organic Chemistry of Drug Design and Drug Action, pp. 352-399, 1992).*
Wolff (Burger's Medicinal Chemistry, 5, vol. 1, 1995).*
Banker (Modem Pharmaceutics, 3rd edition, 1996).*
Sorensen et al. (Arthritis and Rheumatism, 19, 2, 1976).*
PCT International Preliminary Report on Patentability (IPRP) with Written Opinion dated Apr. 9, 2013, from The International Bureau of WIPO, for related International Patent Application No. PCT/US2011/055006 (9 pages).
STN Registry file [online], 2001 (2 pages).
Astoin, Jacques, et al., "Recherchessur le benzoiuranne,LIX, Orientation de l'aroylation de l'éhtyl-2 benzofuranne selon la nature du chloruze d'aruyle utilisé"; Journal of Heterocyclic Chemistry, Aug. 1977, vol. 14, No. 5; pp. 861-866.
Nakanishi, Teru, et al., "Thin-Layer Chromatography of Benzofuran Derivatives"; Japan Society for Bioscience, Biotechnology, and Agrochemistry; Jan. 7, 1969, vol. 43, No. 8; pp. 591-593.

The Merck Index, 2001, Thirteenth Edition; p. 182 and p. 186.
Locuson II, Charles W., et al., "Quantitative Binding Models for CYP2C9 Based on Benzbromarone Analogues"; Biochemistry, 2004, vol. 43; pp. 6948-6958.
Deltour, G., et al., "Recherches Dans La Série Des Benzofurannes XXI. Effet inhibiteur de dérivés benzofuranniques phenoliques et de quelques analogues sur la xanthine oxydase hépatique du rat in vitro"; Archives Internationales de Pharmacodynamie et de Therapie, 1967, vol. 165, No. 1; pp. 25-29 (7 pages).
STN Registry file [online], Nov. 2, 2016.
Office Action issued in corresponding Japanese Application No. 2015-225135 with English Translation dated Nov. 15, 2016 (19 pages).
McDonald, Matthew G., et al., "Sequential Metabolism and Bioactivation of the Hepatotoxin Benzbromarone: Formation of Glutathione Adducts From a Catechol Intermediate"; Chemical Research in Toxicology, vol. 20, 2007; pp. 1833-1842.
Enomoto, Atsushi, et al., "Molecular identification of a renal urate-anion exchanger that regulates blood urate levels"; Letters to Nature, vol. 417, 2002; pp. 447-452.
Anzai, Naohiko, et al., "New insightsinto renal transport of urate"; Current Opinion in Rheumatology, vol. 19, 2007 Lippiincott Williams & Wilkins; pp. 151-157.
Anzai, Naohiko, et al., "Plasma Urate Level is Directly Regulated by a Voltage-driven Urate Efflux Transporter URATv1 (SLC2A9 ) in Humans."; Journal of Biological chemistry, vol. 283, No. 46, Oct. 3, 2008; pp. 26834-26838; with Additions and Corrections dated Nov. 14, 2008; p. 32152.
Anzai, Naohiko, et al., "Renal Solute Transporters and Their Relevance to Serum Urate Disorder"; Current Hypertension Reviews, 6, 2010 Bentham Science Publishers Ltd.; 1573-4021/10; pp. 148-154.
Becker, MD, Michael A., et al., "Hyperuricemia and Associated Diseases"; Rheumatic Disease Clinics of North America, vol. 32 (2006); pp. 275-293.
Caulfield, Mark J., et al., "SLC2A9 is a High-Capacity Urate Transporter in Humans"; PLoS Medicine (www.plosmedicine.org), vol. 5, Issue 10, Oct. 2008 (e197); pp. 1509-1523.
Feig, M.D., Ph.D., Daniel I., et al., "Uric Acid and Cardiovascular Risk"; The New England Journal of Medicine, vol. 359, No. 17, Oct. 23, 2008; pp. 1811-1821.
Jutabha, Promsuk, et al., "Human Sodium Phosphate Transporter 4 (hNPT4/SLC17A3) as a Common Renal Secretory Pathway for Drugs and Urate"; The Journal of Biological Chemistry, vol. 285, No. 45, Nov. 5, 2010; pp. 35123-35132.
Jutabha, Promsuk, et al., "Xenopus laevis oocytes expressing human P-glycoprotein: Probing trans- and cis-inhibitory effects on [3H]vinblastine and [3H]digoxin efflux"; Pharmacological Research, vol. 61 (2010) Elsevier Ltd.; 10-43-6618; doi: 10.1016/j.phrs.2009.07.002; pp. 76-84.
Kutzing, Melinda K., et al.; "Altered Uric Acid Levels and Disease States"; The Journal of Pharmacology and Experimental Therapeutics, vol. 324, No. 1 (129031/3280353); 2008 by The American Society for Pharmacology and Experimental Therapeutics, JPET 324:1-7, 2008; pp. 1-7.
Lee, Ming-Han H., et al., "A Benefit-Risk Assessment of Benzbromarone in the Treatment of Gout—Was its Withdrawal from the Market in the Best Interest of Patients?"; Drug Society, vol. 31, No. 8, 2008 (0114-5916/08/008-0643/$48.00/0; pp. 643-665.
Lemke, Thomas L., et al., Foye's Principles of Medicinal Chemistry, Lippincott Williams & Wilkins, Sixth Edition, Chapter 36, Nonsteroidal Anti-Inflammatory Drugs; pp. 998-1001.
Mount, MD, David B., et al., "Renal Urate Transport"; Rheumatic Disease Clinics of North America, vol. 32, (2006) Elsevier Inc. (doi: 10.1016/j.rdc.2006.02.006; 0889-857X/06); pp. 313-331.
Neogi, M.D., Ph.D.,Tuhina, "Gout"; The New England Journal of Medicine, vol. 364, No. 5, Feb. 3, 2011; pp. 143-452.
Ohtsu, Naoko, et al., "Development of the alternative method for renal drug excretion using Xenopus oocyte expression system combined with a high throughput method, Oocytexpress®"; AATEX 14, Special Issue, 2007; pp. 669-671.
Pombrio, James M., et al., "Mercapturic Acids (N-Acetylcysteine S-Conjugates) as Endogenous Substrates for the Renal Organic

(56) References Cited

OTHER PUBLICATIONS

Anion Transporter-1"; Molecular Pharmacology, vol. 60, No. 5 (1084/940425); © 2001 The American Society for Pharmacology and Experimental Therapeutics; pp. 1091-1099.

Saag, Kenneth G., et al., "Epidemiology, risk factor, and lifestyle modifications for gout"; Arthritis Research and Therapy, vol. 8(Suppl 1):S2 (doi: 10.1186/ar1907), published Apr. 12, 2006, online at http://arthritis-research.com/content/8/S1/S2 © 2006 BioMed Central Ltd; pp. 1-7.

Sekine, Takashi, et al., "Expression Cloning and Characterization of a Novel Multispecific Organic Anion Transporter"; The Journal of Biological Chemistry; vol. 272, No. 30, Jul. 25, 1977 Issue of the American Society for Biochemistry and Molecular Biology, Inc.; (1997); pp. 18526-18529.

Shin, Ho Jung, et al., Interactions of urate transporter URAT1 in human kidney with uricosuric drugs; Nephrology, vol. 16 (2011); pp. 156-162.

Roch-Ramel, Francoise, et al., "Renal Transport of Urate in Humans"; News Physiol. Sci., vol. 14, Apr. 1999; pp. 80-84.

Zubay, G. L, "Biochemistry", Fourth Edition, Chapter 26—Nucleotides; 1998; pp. 629-665.

International Search Report issued in PCT/US2011/055006 dated Apr. 10, 2012 (5 pages).

Michael F Wempe et al.; "Developing Potent Human Uric Acid Transporter 1 (hURAT1) Inhibitors"; Journal of Medicinal Chemistry, vol. 54, No. 8; pp. 2701-2713; Mar. 30, 2011 (13 pages).

Naoki Asao et al.; "Lewis Acid-Catalyzed [4 + 2] Benzannulation between Enynal Units and Enols or Enol Ethers: Novel Synthetic Tools for Polysubstituted Aromatic Compounds Including Indole and Benzofuran Derivatives"; Journal of Organic Chemistry, vol. 71, No. 14; pp. 5249-5253; 2006 (5 pages).

José Bartuenga et al.; "Synthesis of Indoles upon Sequential Reaction of 3-Alkynylpyrrole-2-carboxaldehydes with Iodonium Ions and Alkenes. Preparation of Related Benzofuran and Benzothiophene Derivatives"; Advanced Synthesis & Catalysis, vol. 347, No. 4; pp. 526-530; 2005 (5 pages).

Notice of Reasons for Rejection (Office Action) dated Aug. 4, 2015, by the Japan Patent Office in corresponding Japanese Patent Application No. JP 2013-532932, with English translation (14 pages).

Kawase, Yoshiyuki, et al., "The Fries Rearrangement of bz-Benzoyloxybensofuran Derivatives and the Synthesis of the Furo Derivatives of 4-Phenyl-2H-chromen-2-one"; Bulletin of the chemical Society of Japan, 1978, vol. 51, No. 6; pp. 1907-1908.

* cited by examiner

Chemical Structures for allopurinol (3), febuxostat (4), probenecid (5), sulfinpyrazone (6), benzbromarone (7), 6-hydroxybenzbromarone (8).

Transporters in renal tubular cells

Synthesis of benzbromarone methoxy-(2-ethylbenzofuran-(yl)(4-methoxyphenyl)methanones Benzbromarone 7 and metabolite 8 rat blood concentration data via oral capsule of 7 dosed at 16.4 ± 1.7 mg/kg; rats = 254 ± 12 g.

6-Hydroxy-benzbromarone 8 rat blood concentration data from an oral capsule of 8 dosed at
16.3 ± 1.2 mg/kg; rats = 255 ± 13 g.

6-Methoxy-benzbromarone 45 and metabolite 8 rat blood concentration data from an oral capsule of 45 dosed at 16.9 ± 0.9 mg/kg; rats = 250 ± 7 g.

5-Methoxy-benzbromarone 39 and metabolite 40 rat blood concentration data from an oral capsule dose of 39 dosed at 16.5 ± 0.8 mg/kg; rats = 260 ± 10 g.

5-Hydroxy-benzbromarone 40 rat blood concentration data from an oral capsule dose of 40 dosed at 15.2 ± 0.4 mg/kg; rats = 257 ± 9 g.

5-Fluoro-benzbromarone 70 rat blood concentration data from an oral capsule dose of 70 dosed at 17.2 ± 0.5 mg/kg; rats = 252 ± 9 g.

hURAT1 *in vitro* data

| Compound | % Inhibition @ 50 µM | IC$_{50}$ |
|---|---|---|
| Probenecid (5) | 35.7 ± 2.6 | 86.39 ± 0.07 µM |
| 7 | 99.9 ± 0.1 | 26 ± 3 nM |
| 8 | 99.8 ± 0.2 | 138 ± 88 nM |
| 12 | 13.3 ± 5.7 | ND |
| 13 | 90.8 ± 0.9 | 2.80 ± 0.18 µM |
| 14 | 24.3 ± 5.4 | ND |
| 15 | 6.1 ± 4.3 | ND |
| 16 | 5.2 ± 4.8 | ND |
| 17 | 6.2 ± 9.6 | ND |
| 18 | 1.5 ± 5.6 | ND |
| 19 | 17.2 ± 6.0 | ND |
| 20 | 7.4 ± 11.2 | ND |
| 21 | 92.7 ± 0.8 | 2.46 ± 0.90 µM |
| 22 | 12.9 ± 8.0 | ND |
| 23 | 96.5 ± 0.5 | 2.49 ± 0.14 µM |
| 24 | 88.2 ± 0.8 | 6.68 ± 0.09 µM |
| 25 | 28.7 ± 5.4 | ND |
| 26 | 51.5 ± 4.0 | ND |
| 27 | 60.0 ± 2.5 | 33.65 ± 0.13 µM |
| 28 | 9.3 ± 5.3 | ND |
| 29 | 41.0 ± 0.6 | ND |
| 30 | 92.7 ± 0.8 | 3.92 ± 0.17 µM |
| 31 | 48.3 ± 3.9 | ND |
| 32 | 92.1 ± 0.9 | 1.13 ± 0.11 µM |
| 33 | 62.4 ± 1.8 | 19.69 ± 0.20 µM |
| 34 | 12.4 ± 4.7 | ND |
| 35 | 41.0 ± 5.5 | ND |
| 36 | 18.2 ± 7.3 | ND |
| 37 | 0.8 ± 8.7 | ND |
| 38 | 93.8 ± 0.7 | 3.94 ± 0.15 µM |
| 39 | 99.9 ± 0.1 | 42 ± 9 nM |
| 40 | 99.9 ± 0.1 | 189 ± 90 nM |
| 41 | 99.6 ± 0.4 | 358 ± 130 nM |
| 42 | 99.9 ± 0.1 | 83 ± 10 nM |
| 43 | 99.0 ± 0.1 | 1.44 ± 0.14 µM |
| 44 | 99.8 ± 0.2 | 287 ± 118 nM |
| 45 | 99.9 ± 0.1 | 111 ± 14 nM |
| 46 | 98.1 ± 0.2 | 1.65 ± 0.12 µM |
| 47 | 99.9 ± 0.1 | 177 ± 80 nM |
| 48 | 76.5 ± 1.2 | 23.46 ± 0.27 µM |
| 49 | 99.8 ± 0.2 | 667 ± 88 nM |
| 50 | 99.3 ± 0.3 | 772 ± 215 nM |

ND = no data

FIG. 15

Data Summary: Urate transport % inhibition

| inhibitors | % Inhibition | IC$_{50}$ |
|---|---|---|
| 51 | 13.5 | ND |
| 52 | 10.4 | ND |
| 53 | 23.6 | ND |
| 54 | 29.4 | ND |
| 55 | 52.4 | ND |
| 56 | 22.2 | ND |
| 59 | 97.9 | 2.41 ± 0.09 μM |
| 60 | 98.8 | 874 ± 56 nM |
| 61 | 99.1 | 814 ± 160 nM |
| 62 | 99.4 | 1.49 ± 0.08 μM |
| 63 | 16.9 | ND |
| 64 | 39.4 | ND |
| 65 | 13.8 | ND |
| 68 | 27.2 | ND |
| 69 | 98.0 | 1.59 ± 0.11 μM |
| 70 | 100.6 | 6 ± 4 nM |
| 73 | 20.3 | ND |
| 74 | 94.0 | 3.75 ± 0.09 μM |
| 75 | 74.0 | 45.21 ± 0.39 μM |
| 76 | 95.6 | 2.05 ± 0.12 μM |
| 77 | 100.4 | 401 ± 116 nM |
| 79 | 99.7 | 387 ± 67 nM |
| 82 | 93.7 | 7.54 ± 0.06 μM |
| 84 | 0.6 | ND |
| 85 | 92.1 | 12.19 ± 0.11 μM |
| 87 | 91.0 | 19.32 ± 0.09 μM |
| 88 | 99.9 | 399 ± 56 nM |

ND = no data

FIG. 16 hURAT1, hURAT2, and hURATv1 *in vitro* inhibitor data summary

| inhibitors | URAT1 % Inhibition | URAT2 % Inhibition | URATv1 % Inhibition | % Sum | Preferred |
|---|---|---|---|---|---|
| 7 | 99.9 | 95.2 | 71.1 | 266 | Yes |
| 8 | 99.9 | 99.9 | 20.2 | 220 | Yes |
| 13 | 90.8 | -3.3 | 21.8 | 109 | No |
| 21 | 92.7 | 13.3 | 18.2 | 124 | No |
| 23 | 96.5 | 16.1 | 25.2 | 138 | No |
| 24 | 88.2 | -1.9 | 33.1 | 119 | No |
| 26 | 51.5 | -3.7 | 7.3 | 55 | No |
| 27 | 60.0 | -17.5 | 35.8 | 78 | No |
| 29 | 41.0 | -5.4 | 32.3 | 68 | No |
| 30 | 92.7 | 2.2 | 38.3 | 133 | No |
| 31 | 48.3 | 18.1 | 19.0 | 85 | No |
| 32 | 92.1 | 14.6 | 19.3 | 126 | No |
| 38 | 93.8 | 24.8 | 62.4 | 181 | Yes |
| 39 | 99.9 | 98.5 | 57.0 | 255 | Yes |
| 41 | 99.6 | 91.0 | 45.7 | 236 | Yes |
| 43 | 99.9 | 87.0 | 42.9 | 230 | Yes |
| 44 | 100 | 67.8 | 53.4 | 221 | Yes |
| 45 | 99.9 | 96.9 | 60.3 | 257 | Yes |
| 46 | 98.2 | 29.8 | 24.5 | 153 | No |
| 47 | 99.9 | 98.9 | 34.3 | 233 | Yes |
| 49 | 99.9 | 96.7 | -5.5 | 191 | Yes |
| 50 | 99.3 | 68.8 | 76.9 | 245 | Yes |
| 62 | 99.4 | 38.3 | -50.9 | 87 | No |
| 69 | 98.0 | 12.3 | 10.7 | 121 | No |
| 70 | 100.6 | 50.9 | 94.5 | 246 | Yes |
| 73 | 20.3 | -4.6 | -0.2 | 16 | No |
| 74 | 94.0 | 6.9 | 15.9 | 117 | No |
| 75 | 74.0 | 15.1 | -6.4 | 83 | No |
| 76 | 95.6 | 32.2 | -11.2 | 117 | No |
| 77 | 100.4 | 67.6 | 90.3 | 258 | Yes |
| 82 | 93.1 | 24.2 | -19.1 | 98 | No |
| 84 | 0.6 | 13.1 | -9.3 | 4 | No |
| 85 | 92.1 | 20.1 | 1.3 | 114 | No |
| 87 | 91.0 | 20.5 | -28.3 | 83 | No |
| 88 | 99.9 | 97.7 | 38.0 | 236 | Yes |
| 89 | 99.7 | 35.1 | 39.6 | 174 | Yes |

FIG. 17

DEVELOPING POTENT URATE TRANSPORTER INHIBITORS: COMPOUNDS DESIGNED FOR THEIR URICOSURIC ACTION

BACKGROUND

A vital organ, the kidneys serve several purposes including homeostatic functions such as regulating extracellular fluid volume, maintaining acid-base and electrolyte balance, and are essential regarding the secretion of metabolic waste. The kidneys play an important role in uric acid secretion/re-absorption. Kidney transporter protein abnormalities (i.e. altered function) are associated with various diseases, such as gout. In humans, purine nucleotides, nucleosides, and bases (i.e. adenine, inosine, and guanine) are metabolically degraded to urate (uric acid 1, FIG. 1) via xanthine.

Many organisms possess the enzyme uricase and metabolize 1 to the more water soluble allantoin 2, however this enzyme is absent in humans (Zubay, 1998; Neogi, 2011). A known antioxidant in the blood, elevated levels of uric acid (a condition known as hyperuricemia) can precipitate gout; a medical condition associated with repeated episodes of acute inflammatory arthritis caused by elevated urate serum level (Shin et al, 2011). Lifestyle and diet are also well known contributors to elevated serum urate (Sang et al, 2006). Renal function declines as we age to produce lower urate excretion. Furthermore, high uric acid levels in the body are believed to play a pivotal role in other diseases such as hypertension, insulin resistance, diabetes, chronic renal disease, diabetic renal disease, and cardiovascular disease (Sang et al, 2006; Feig et al, 2008; Anzai et al, 2010). Therefore, developing novel drugs that influence uric acid serum level are therapeutically important.

There are different drug strategies to control urate levels (FIG. 2). A few commercially available small molecule drugs are administered to lower serum urate in the United States. Allopurinol 3 is a xanthine oxidase inhibitor and the most commonly used urate-lowering drug in the US. Compound 3 occasionally causes Stevens Johnson syndrome and may be fatal (Lemke and Williams. 2008). Another drug, febuxostat 4 is as a non-purine xanthine oxidase inhibitor but known to afford cardiovascular complications. Probenecid 5, sulfinpyrazone 6 and benzbromarone 7 are uricosuric drugs; they increase uric acid renal excretion by inhibiting urate re-absorption via one or more transporter proteins (Shin et al, 2011).

Renal elimination plays a primary role in controlling uric acid serum level (Becker and Jolly, 2006; Anzai et al, 2007; Kutzing and Firestein, 2008). Urate is reabsorbed and secreted along the nephron. In humans, the apical surface (FIG. 3) contains human uric acid transporter 1 (hURAT1; SLC22A12), human organic anion transporter 10 (hOAT10; URAT2), and the natrium-dependent phosphate transporter 4, also called voltage-dependent human organic anion transporter 1 (NPT4, hOATv1; SLC17A3) (Shin et al, 2011; Enomoto et al, 2002; Roch-Ramel and Guisan, 1999; Mount et al, 2006). Consequently, these transporters interact with the urine.

The basolateral surface also contains transporters, but they are in contact with the blood and include: i) the facilitative glucose transporter 9, also known as the voltage-dependent uric acid transporter 1 (GLUT9, URATv1; SLC2A9) (Mount et al, 2006; Jutabha et al, 2010; Anzai et al, 2008; Caulfied et al, 2008) and human organic anion transporter proteins 1 (hOAT1; SLC22A6) and 3 (hOAT3; SLC22A8) known to have broad substrate specificity and transport, in addition to urate, they are known to transport NSAIDs, (3-lactams, and p-aminohippuric acid (Sekine et al, 1997).

Benzbromarone 7 effectively reduces serum urate levels and has been administered clinically in Japan and previously in Europe; however, 7 is not approved in the US. Metabolized by CYP2C9 (major) and CYP2C19 (minor), idiosyncratic hepatotoxic events associated with 7 are hypothesized to result from CYP biotransformation down-stream from initial metabolite 8 (McDonald and Bettie, 2007). In 2008, Lee and coworkers compared oral in vivo efficacy and concluded that 7 (100 mg/kg) produces a greater physiological effect (i.e. lowers urate level) than 4 (300 mg/day) or 5 (1000 mg/day) (Lee et al, 2008). Previous results from our laboratories illustrated 7 and 8 to have potent hURAT1 inhibitor properties (Enomoto et al, 2002; Shin et al, 2011). Therefore we sought to prepare a series of novel compounds and probe the interactions and structural requirement(s) related to transporter proteins involved in urate inhibition.

SUMMARY

A first embodiment according to the present invention involves a composition, comprising at least one compound represented by the general Formula I:

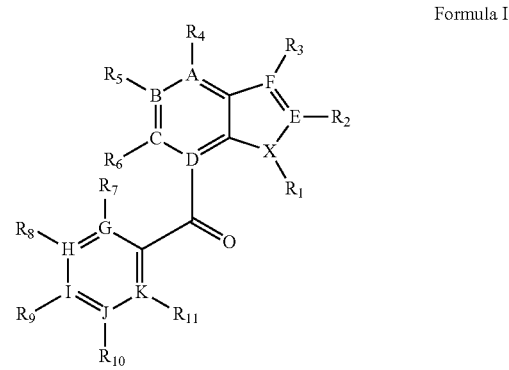

Formula I a pharmaceutically acceptable salt or ester thereof, a solvate thereof, a chelate thereof, a non-covalent complex thereof, a pro-drug thereof, a deuterated or radio-labeled analog thereof, and mixtures of any of the foregoing, wherein:

A-K are individually selected from carbon or nitrogen;

X=—O, —$NR_1$, or —S;

$R_{1-11}$ are individually selected from the group consisting of —H, $C_1$-$C_6$ alkyl, $C_6$-$C_{14}$ aryl, substituted $C_6$-$C_{14}$ aryl, $C_1$-$C_{14}$-alkoxy, halogen, hydroxyl, carboxy, cyano, $C_1$-$C_6$-alkanoyloxy, $C_1$-$C_6$-alkylthio-, $C_1$-$C_6$-alkylsulfonyl, trifluoromethyl, hydroxy, $C_2$-$C_6$-alkoxycarbonyl, $C_2$-$C_6$-alkanoylamino, —O—$R_{12}$, S—$R_{12}$, —$SO_2$—$R_{12}$, —$NHSO_2R_{12}$ and —$NHCO_2R_{12}$, wherein $R_{12}$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatoms are selected from the group consisting of sulfur, nitrogen, and oxygen;

A second embodiment according to the present invention involves a composition, comprising at least one compound represented by the general Formula II:

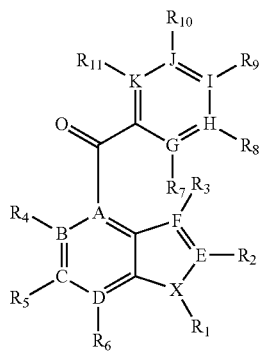

Formula II a pharmaceutically acceptable salt or ester thereof, a solvate thereof, a chelate thereof, a non-covalent complex thereof, a pro-drug thereof, a deuterated radio-labeled analog thereof, and mixtures of any of the foregoing, wherein:

A-K are individually selected from carbon or nitrogen;

X=—O, —NR$_1$, or —S;

R$_{1-11}$ are individually selected from the group consisting of —H, $C_1$-$C_6$ alkyl, $C_6$-$C_{14}$ aryl, substituted $C_6$-$C_{14}$ aryl, $C_1$-$C_{14}$-alkoxy, halogen, hydroxyl, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino, —O—R$_{12}$, S—R$_{12}$, —SO$_2$—R$_{12}$, —NHSO$_2$R$_{12}$ and —NHCO$_2$R$_{12}$, wherein R$_{12}$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatoms are selected from the group consisting of sulfur, nitrogen, and oxygen;

A third embodiment according to the present invention involves a composition, comprising at least one compound represented by the general Formula III:

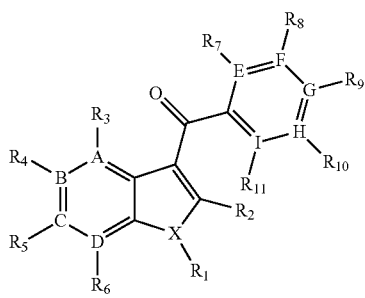

Formula III a pharmaceutically acceptable salt or ester thereof, a solvate thereof, a chelate thereof, a non-covalent complex thereof, a pro-drug thereof, a radio-labeled analog thereof, and mixtures of any of the foregoing, wherein:

A-I are individually selected from carbon or nitrogen;

X=—O, —NR$_1$, or —S;

R$_{1-11}$ are individually selected from the group consisting of —H, $C_1$-$C_6$ alkyl, $C_6$-$C_{14}$ aryl, substituted $C_6$-$C_{14}$ aryl, $C_1$-$C_{14}$-alkoxy, halogen, hydroxyl, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino, —O—R$_{12}$, S—R$_{12}$, —SO$_2$—R$_{12}$, —NHSO$_2$R$_{12}$ and —NHCO$_2$R$_{12}$, wherein R$_{12}$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatoms are selected from the group consisting of sulfur, nitrogen, and oxygen;

Additional embodiment(s) concern methods for treating a condition comprising administering an effective amount of a composition comprising a compound, pharmaceutical and/or dermatological carriers, wherein the compound is represented by at least one compound of Formulas I-III.

Further embodiment(s) concern methods to diagnosis and/or monitor a condition comprising administering an effective amount of a composition comprising a compound, pharmaceutical and/or dermatological carriers, wherein the compound is represented by at least one compound of Formula I-III.

BRIEF DESCRIPTION OF THE DRAWINGS

FIG. 15 is a table showing hURAT1 in vitro data.

FIG. 16 is a table showing data summary for urate transport % inhibition.

FIG. 17 is a table showing hURAT1, hURAT2, and hURATv1 in vitro inhibitor data summary.

DETAILED DESCRIPTION OF THE EMBODIMENTS

Figure 1:
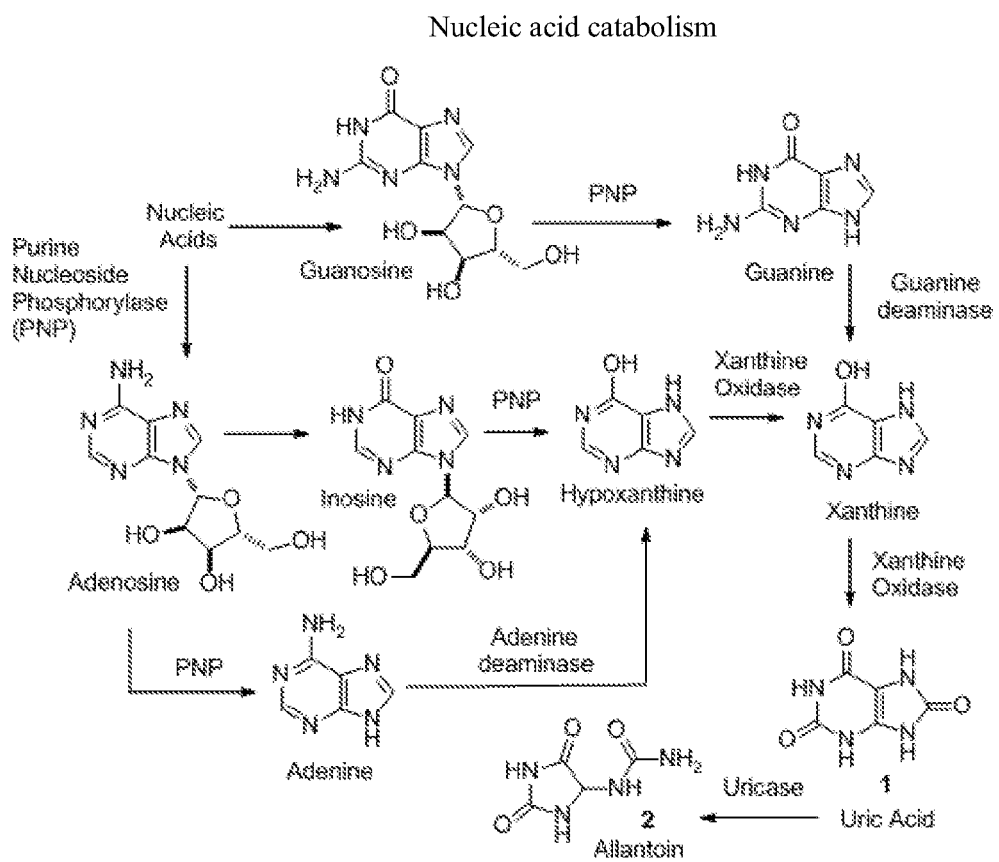
FIG. 1 is a schematic diagram of nucleic acid catabolism.
Figure 2:
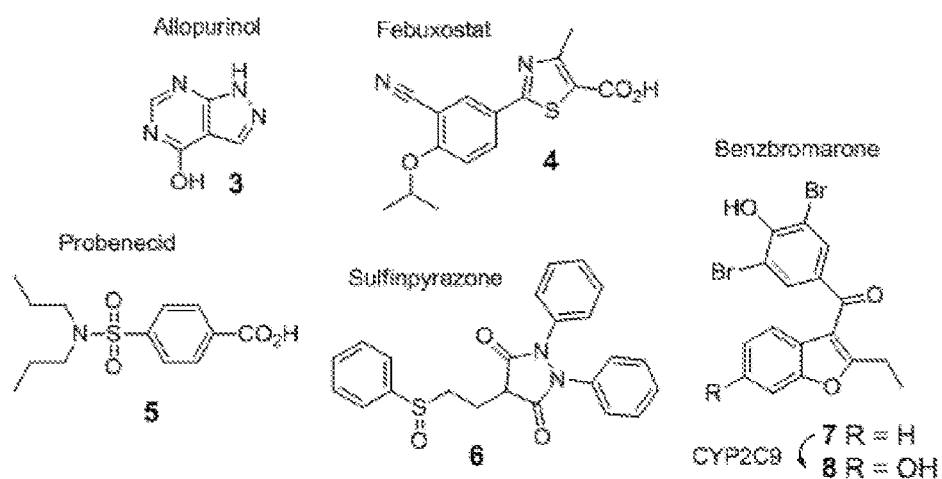
FIG. 2 shows chemical structures for allopurinol (3), febuxostat (4), probenecid (5), sulfinpyrazone (6), benzbromarone (7), and 6-hydroxybenzbromarone (8).
Figure 3:
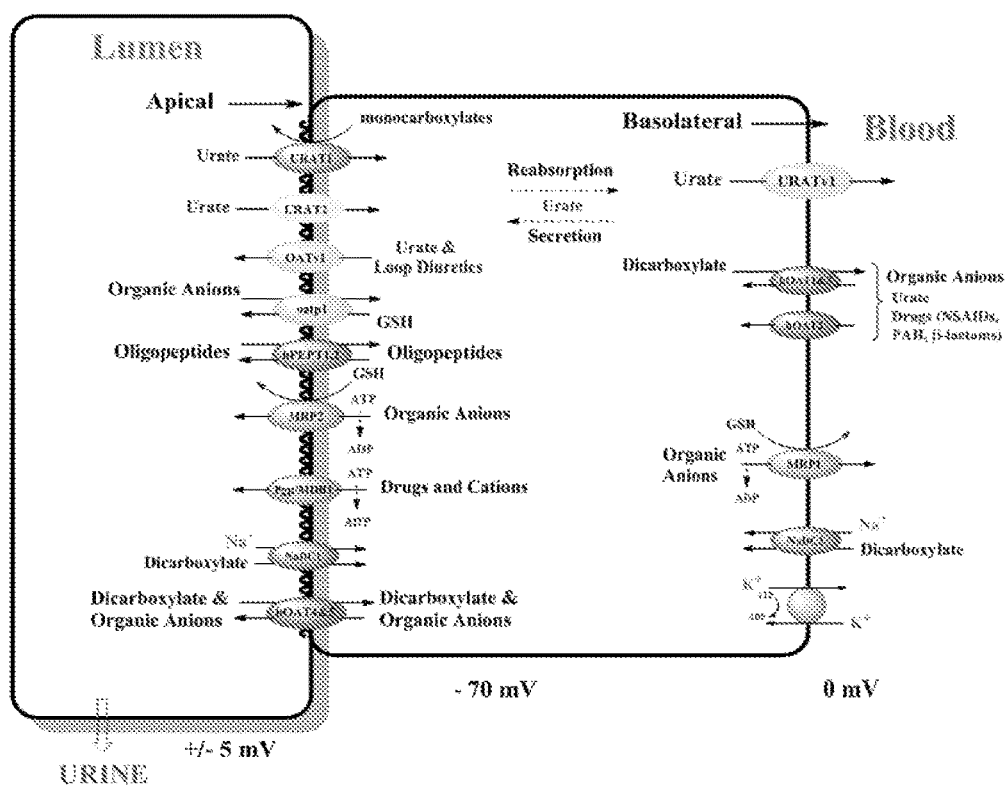
FIG. 3 shows transporters in renal tubular cells.

The present invention concerns a series of novel compounds and their compositions represented by at least one compound of Formula I-III:

Formula I

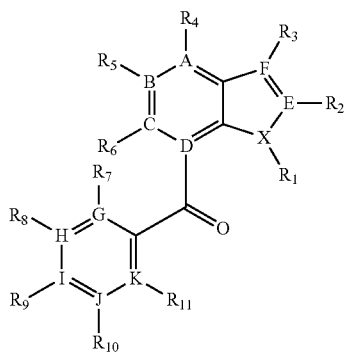

Formula II

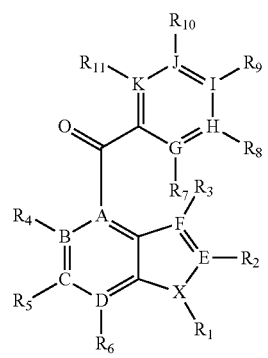

Formula III

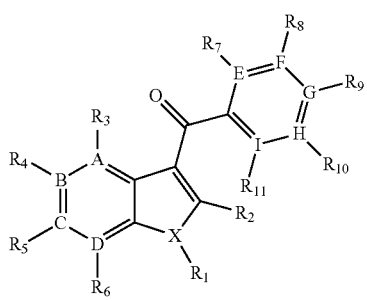

a pharmaceutically acceptable salt or ester thereof, a solvate thereof, a chelate thereof, a non-covalent complex thereof, a pro-drug thereof, a radio-labeled analog thereof, and mixtures of any of the foregoing, wherein:

A-K are individually selected from carbon or nitrogen;

X=—O, —$NR_1$, or —S;

$R_{1-11}$ are individually selected from the group consisting of —H, $C_1$-$C_6$ alkyl, $C_6$-$C_{14}$ aryl, substituted $C_6$-$C_{14}$ aryl, $C_1$-$C_{14}$-alkoxy, halogen, hydroxyl, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino, —O—$R_{12}$, S—Ru, —$SO_2$—$R_{12}$, —$NHSO_2R_{12}$ and —$NHCO_2R_{12}$, wherein $R_{12}$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatoms are selected from the group consisting of sulfur, nitrogen, and oxygen;

As used throughout this application, the term "pharmaceutically effective amount of a compound for pharmaceutical use" shall mean an amount of compound that exhibits the intended pharmaceutical or therapeutic or diagnostic effect when administered. Examples of methods of administration include, but are not limited to, oral administration (e.g., ingestion, buccal or sublingual administration), anal or rectal administration, topical application, aerosol application, inhalation, intraperitoneal administration, intravenous administration, transdermal administration, intradermal administration, subdermal administration, intramuscular administration, intrauterine administration, vaginal administration, administration into a body cavity, surgical administration (for example, at the location of an internal injury), administration into the lumen or parenchyma of an organ, and parenteral administration. The compositions can be administered in any form by any means. Examples of forms of administration include, but are not limited to, injections, solutions, creams, gels, implants, ointments, emulsions, suspensions, microspheres, powders, particles, microparticles, nanoparticles, liposomes, pastes, patches, capsules, suppositories, tablets, transdermal delivery devices, sprays, suppositories, aerosols, or other means familiar to one of ordinary skill in the art. In some embodiments, the compositions can be combined with other components. Examples include, but are not limited to, coatings, depots, matrices for time release and osmotic pump components.

The term "solvate" refers to the compound formed by the interaction of a solvent and a compound. Suitable solvates are pharmaceutically acceptable solvates, such as hydrates, including monohydrates and hemi-hydrates. "Pharmaceutically acceptable salt" refers to a salt of a compound that is pharmaceutically acceptable and that possesses the desired pharmacological activity of the parent compound. Such salts may include: (i) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

In some embodiments, the one or more compounds, or compositions of the present invention, are administered to persons or animals to provide substances in any dose range that will produce desired physiological or pharmacological results. Dosage will depend upon the substance or substances administered, the therapeutic endpoint desired, the diagnostic endpoint desired, the desired effective concentration at the site of action or in a body fluid, and the type of administration. Information regarding appropriate doses of substances are known to persons of ordinary skill in the art and may be found in references such as L. S. Goodman and A. Gilman, eds, The Pharmacological Basis of Therapeutics, Macmillan Publishing, New York, and Katzung, Basic & Clinical Pharmacology, Appleton & Lang, Norwalk, Conn. (6.sup.th Ed. 1995). In some embodiments, the compounds and compositions of the present invention may be administered to a subject. Suitable subjects include a cell, population of cells, tissue or organism. In certain embodiments, the subject is a mammal such as a human. The compounds may be administered in vitro or in vivo.

The invention includes methods in which one or more compounds are an admixture or otherwise combined with one or more compounds and may be in the presence or absence of commonly used excipients; for example, but not limited to: i) diluents and carriers such as starch, mannitol, lactose, dextrose, sucrose, sorbitol, mannitol, cellulose, and the like; ii) binders such as starch paste, gelatin, magnesium aluminum silicate, methylcellulose, alginates, gelatin, sodium carboxymethyl-cellulose, polyvinylpyrrolidone and the like; iii) lubricants such as stearic acid, talcum, silica, polyethylene glycol, polypropylene glycol and the like; iv) absorbents, colorants, sweeteners and the like; v) disintegrates, (e.g., calcium carbonate and sodium bicarbonate) such as effervescent mixtures and the like; vi) excipients (e.g. cyclodextrins and the like); vii) surface active agents (e.g., cetyl alcohol, glycerol monostearate), adsorptive carriers (e.g., kaolin and bentonite), emulsifiers and the like. Examples of carriers include, without limitation, any liquids, liquid crystals, solids or semi-solids, such as water or saline, gels, creams, salves, solvents, diluents, fluid ointment bases, ointments, pastes, implants, liposomes, micelles, giant micelles, and the like, which are suitable for use in the compositions.

Furthermore, said invention includes compositions prepared using conventional mixing, granulating, or coating methods and may contain 0.01 to 90% of the active ingredients. In some embodiments, the one or more compounds are for pharmaceutical use or for diagnostic use. Such methods can be used, for example, to prepare a bio-enhanced pharmaceutical composition in which the solubility of the compound(s) is (are) enhanced. In some embodiments, the resulting compositions contain a pharmaceutically effective amount of a compound for pharmaceutical or diagnostic use. The resulting compositions (formulations) may be presented in unit dosage form and may be prepared by methods known in the art of pharmacy. All methodology includes the act of bringing the active ingredient(s) into association with the carrier which constitutes one or more ingredients. Therefore, compositions (formulations) are prepared by blending active ingredient(s) with a liquid carrier or a finely divided solid carrier, and/or both, and then, if needed, shaping the product into a desired formulation.

Topical application to skin sites is accomplished in association with a carrier, and particularly one in which the active ingredient is soluble per se or is effectively solubilized (e.g., as an emulsion or microemulsion). Where employed, the carrier is inert in the sense of not bringing about a deactivation or oxidation of active or adjunct ingredient(s), and in the sense of not bringing about any adverse effect on the skin areas to which it is applied. For example, the compounds according to the present invention are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. While the carrier for dermatological compositions can consist of a relatively simple solvent or dispersant such as water, it is generally preferred that the carrier comprise a composition more conducive to topical application. In particular, a dermatological composition which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic, or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Such compositions are referred to herein as dermally, dermatologically, or pharmaceutically acceptable carriers. "Therapeutically effective amount" or "effective amount" refers to the amount of a compound that, when administered to a subject for treating or diagnosing or monitoring a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to monitoring, delaying or preventing the onset or reoccurrence of the disease or disorder or at least symptoms thereof in a subject which may be exposed to or predisposed to or may have previously suffered from a disease or disorder even though that subject does not yet experience or display symptoms of the disease or disorder.

Typical compositions of the invention contain compound from about 90 to about 80% by weight, from about 80 to about 70% by weight, from about 70 to about 60% by weight, from about 60 to about 50% by weight, from about 50 to about 40% by weight, from about 40 to about 30% by weight, from about 30 to 20% by weight, from about 20 to about 10% by weight, from about 10 to about 4% by weight, from about 4.0% to about 2.0% by weight, from about 2.0% to about 1.0% by weight, and even from about 1.0% to about 0.01% by weight. Lower concentrations may be employed for less pronounced conditions and higher concentrations may be employed with more acute conditions. The effective amount of compounds or compositions of the invention may range from about 0.1 to 100 milligrams (mg) per kilogram (kg) of subject weight. In certain embodiments, the compounds or compositions of the invention are administered at from about 0.0001 mg/kg to 0.1 mg/kg, or from 0.1 mg/kg to 2 mg/kg, or from about 2 mg/kg to 5 mg/kg; in other embodiments, from about 5 mg/kg to 10 mg/kg, from about 10 mg/kg to 20 mg/kg, from about 20 mg/kg to 30 mg/kg, from about 30 mg/kg to 40 mg/kg, from about 40 mg/kg to 50 mg/kg, from about 50 mg/kg to 75 mg/kg or from about 75 mg/kg to 100 mg/kg.

It should be understood that the ingredients particularly mentioned above are merely examples and that some embodiments of formulations comprising the compositions of the present invention include other suitable components and agents. The invention further includes packages, vessels, or any other type of container that contain a compound of the present invention.

General Synthesis Scheme and Examples

The invention can be further illustrated by the following synthetic methods, although it will be understood that these examples are included merely for purposes of illustration and are not intended to limit the scope of the invention in any way unless otherwise specifically indicated.

Materials and Methods

Benzaldehyde, chloroacetone, silica gel (70-230 mesh), diethylene glycol (DEG), hydrazine (55% aqueous solution), potassium hydroxide (KOH), anhydrous magnesium sulfate ($Mg_2SO_4$), anhydrous sodium sulfate ($Na_2SO_4$), carbon disulfide ($CS_2$), p-anisoyl chloride, m-anisoyl chloride, 3,5-dimethoxybenzoyl chloride, tin (IV) chloride, conc. hydrochloric acid (HCl), sodium bicarbonate ($NaHCO_3$), sodium chloride (NaCl), 2-hydroxy-5-methoxybenzaldehyde, 2-hydroxy-3-methoxybenzaldehyde (o-vanillin), 2-hydroxy-4-methoxybenzaldehyde, 2-hydroxybenzaldehyde, 1,2-dimethyl-1H-indole, 4-fluorobenzoyl chloride, 4-cyanobenzoyl chloride, 3-chloro-4-methoxybenzoic acid, 3-bromo-4-methoxy-benzoic acid, N-bromosuccinimide (NBS), bromine ($Br_2$), ammonium chloride ($NH_4Cl$), 3-iodo-4-methoxybenzoic acid, 3,5-dichloro-4-hydroxybenzoic acid, thionyl chloride ($SOCl_2$), 3,5-dimethyl-4-methoxy-benzoic acid, 3,5-di-tert-butyl-4-hydroxybenzoic acid, iodomethane, benzoyl chloride-$d_5$, sodium ethanethiolate (NaSEt), and formic acid were purchased from Sigma-Aldrich Chemical Company (St. Louis, Mo.). Acetone, hexanes (Hex), ethyl acetate (EtOAc), benzene, toluene, potassium carbonate ($K_2CO_3$), dimethylformamide (DMF), methylene chloride (DCM), sodium hydroxide (NaOH), HPLC grade methanol (MeOH), HPLC grade acetonitrile (ACN), isopropanol, acetic acid (AA), and HPLC grade water ($H_2O$) were purchased from Fisher Scientific (Pittsburgh, Pa.). Compounds 3-fluoro-2-hydroxybenzaldehyde, 3-fluoro-p-anisic acid, 2-butylbenzofuran and 5-fluoro-2-hydroxybenzaldehyde were purchased from TCI America (Chicago, Ill.). The NMR solvents $CDCl_3$, DMSO-$d_6$, and $D_2O$ were purchased from either Sigma-Aldrich or Cambridge Isotope Laboratories, Inc. (Andover, Mass.). Reactions were monitored via Silica gel IB2-F thin layer chromatography (TLC) plates, and were purchased from J. T. Baker (Phillipsburg, N.J.).

The $^1H$ and $^{13}C$ NMR spectra were recorded using a 400 MHz Bruker NMR, Avance III 400. The chemical shifts are reported in ppm. An Applied Biosystems Sciex 4000 (Applied Biosystems; Foster City, Calif.) was equipped with a Shimadzu HPLC (Shimadzu Scientific Instruments, Inc.; Columbia, Md.) and Leap auto-sampler (LEAP Technologies; Carrboro, N.C.) was used. Liquid chromatography employed an Agilent Technologies, Zorbax extended-C18 50×4.6 mm, 5 micron column at 40° C. with a flow-rate of 0.4 mL/min. The mobile phase consisted of A: 10 mM ($NH_4OAc$), 0.1% formic acid in $H_2O$, and B: 50:50 ACN:MeOH. The chromatography method used was 95% A for 1.0 mM; ramped to 95% B at 3.00 mM and held for 4.5 min, lastly, brought back to 95% A at 8.5 mM and held for 1.0 min (9.5 mM total run time). Unless specifically denoted for an individual compound, compounds were monitored via electro-spray ionization positive ion mode (ESI+) using the following conditions: i) an ion-spray voltage of 5500 V; ii) temperature, 450° C.; iii) curtain gas (CUR; set at 10) and Collisionally Activated Dissociation (CAD; set at 5) gas were nitrogen; iv) Ion Source gas one (GS1) and two (GS2) were set at either 20 or 25, and specifically denoted in the individual compound section; v) entrance potential was set at 10 V; yl) quadruple one (Q1) and (Q3) were set on Unit resolution; vii) dwell time was set at 200 msec; and viii) declustering potential (DP), collision energy (CE), and collision cell exit potential (CXP) are voltages (V). Samples (10 μL) were analyzed by LC/MS-MS. As judged by TLC, NMR and LC/MS-MS analysis, all purified compounds were >95% pure.

Chemical Synthesis:

2-Ethyl-benzofurans 1-(benzofuran-2-yl)ethanone (10A) $K_2CO_3$ (13.6 g) was added to a dry round bottom flask (RBF; 250 mL) containing a stir bar (SB). The contents were diluted with anhydrous acetone (140 mL) and stirred while benzaldehyde (10.0 g; 81.9 mmol) was added dropwise (2-3 min). Next, chloroacetone (8.75 g; 94.6 mmol) was added (2-3 min). A reflux condenser was attached and contents heated to reflux (6 h). The contents were cooled to ambient temperature and Buchner filtered; the solid was rinsed with acetone (2×50 mL). The filtrate was concentrated under reduced pressure and purified via $SiO_2$ chromatography (2:1; Hex:EtOAc) to afford a light yellow solid (12.3 g; 59.9 mmol; 91% yield). $^1H$-NMR (400 MHz) $CDCl_3$: 2-7.70 (d, 1H), 7.59-7.57 (d, 1H), 7.51-7.45 (m, 2H), 7.33-7.29 (t, 1H), 2.61 (s, 3H); $^{13}C$-NMR (100 MHz) $CDCl_3$: 188.7, 155.7, 152.7, 128.4, 127.1, 124.0, 123.4, 113.2, 112.5, 26.6. Using analogous procedures, the following analogs were prepared: 1-(5-methoxybenzofuran-2-yl)ethanone (10B): (85% yield). $^1H$-NMR (400 MHz) $CDCl_3$: 7.47-7.43 (m, 2H), 7.10-7.08 (m, 2H), 3.85 (s, 3H), 2.59 (s, 3H); $^{13}C$-NMR (100 MHz) $CDCl_3$: 188.6, 156.6, 153.3, 150.9, 127.6, 118.5, 113.5, 113.2, 103.9, 55.8, 26.4. 1-(6-methoxybenzofuran-2-yl) ethanone (10C): (83% yield). $^1H$-NMR (400 MHz) $CDCl_3$: 7.56-7.54 (d, 1H), 7.44 (s, 1H), 7.03 (s, 1H), 6.95-6.92 (d, 1H), 3.87 (s, 3H), 2.56 (s, 3H); $^{13}C$-NMR (100 MHz) $CDCl_3$: 187.9, 161.2, 157.3, 152.3, 123.7, 120.3, 114.4, 113.9, 95.6, 55.7, 26.2. 1-(7-methoxybenzofuran-2-yl)ethanone (10D): (91% yield). $^1H$-NMR (400 MHz) $CDCl_3$: 7.48 (s, 1H), 7.28-7.20 (m, 2H), 6.95-6.94 (d, 1H), 4.02 (s, 3H), 2.63 (s, 3H); $^{13}C$-NMR (100 MHz) $CDCl_3$: 188.8, 153.0, 146.1, 145.3, 128.7, 124.6, 115.1, 112.8, 109.4, 56.1, 26.7.

2-Ethylbenzofuran (11A) Ketone (12.1 g; 75.5 mmol) in a RBF/SB (500 mL) was mixed with DEG (290 mL) and heated (120-130° C.). The mixture was stirred and hydrazine (16.1 g; 55% aq solution) was added dropwise (15-20 min). The mixture was heated (180-190° C.; 10 min) and then decreased to 120-130° C. Next, KOH (13.2 g) was carefully added in portions and heated (120-130° C.; 6 h). The contents were diluted with ice water (220-230 mL) and extracted (DCM; 4×350 mL). The organic phase was dried over anhydrous $MgSO_4$, filtered, concentrated under reduced pressure, and purified via $SiO_2$ chromatography (4:1; Hex:EtOAc) to afford a light yellow oil (6.05 g; 41.3 mmol; 55% yield). $^1H$-NMR (400 MHz) $CDCl_3$: 7.51-7.47 (d, 1H), 7.42-7.40 (d, 1H), 7.50-7.22 (m, 2H), 6.38 (s, 1H), 2.83-2.77 (q, 2H), 1.34-1.32 (t, 3H); $^{13}C$-NMR (100 MHz) $CDCl_3$: 161.1, 154.8, 129.1, 123.2, 122.5, 120.3, 110.8, 101.1, 21.9, 12.0. Using analogous procedures, the following analogs were prepared: 2-ethyl-5-methoxybenzofuran (11B): (68% yield). $^1H$-NMR (400 MHz) $CDCl_3$: 7.35-7.32 (d, 1H), 6.97 (s, 1H), 6.82-6.80 (dd, 1H), 6.28 (s, 1H), 3.83 (s, 3H), 2.79-2.75 (q, 2H), 1.33-1.27 (t, 3H); $^{13}C$-NMR (100 MHz) $CDCl_3$: 160.2, 157.3, 155.6, 122.4, 120.3, 111.1, 100.7, 95.9, 55.8, 21.9, 12.1. 2-ethyl-6-methoxybenzofuran (11C): (90% yield). $^1$H-NMR (400 MHz) CDCl$_3$: 7.32-7.29 (d, 1H), 6.97 (s, 1H), 6.83-6.80 (dd, 1H), 6.32 (1H), 3.83 (s, 3H), 2.79-2.75 (q, 2H), 1.35-1.29 (t, 3H); $^{13}$C-NMR (100 MHz) CDCl$_3$: 162.0, 155.8, 149.7, 129.7, 111.4, 111.1, 103.3, 101.1, 56.0, 22.0, 12.0. 2-ethyl-7-methoxybenzofuran (11D): (91% yield). $^1$H-NMR (400 MHz) CDCl$_3$: 7.12-7.08 (m, 2H), 6.74-6.72 (d, 1H), 6.37 (s, 1H), 4.00 (s, 3H), 2.83-2.81 (q, 2H), 1.35-1.31 (t, 3H); $^{13}$C-NMR (100 MHz) CDCl$_3$: 161.3, 145.0, 143.8, 130.7, 123.2, 112.9, 105.4, 101.5, 56.0, 21.9, 12.1.

(2-Ethylbenzofuran-3-yl)(4-methoxyphenyl)methanone (12): Benzofuran (11A; 2.50 g; 17.1 mmol) in a RBF/SB (250 mL) was diluted with CS$_2$ (50 mL). The reaction vessel was capped with a sure-seal and a N$_2$ balloon attached. The vessel was cooled in an ice bath (30 min). Next, p-anisoyl chloride (1.3 mol equiv.) was added dropwise (3-4 min) followed by tin (IV) chloride (1.3 mol equiv.) added dropwise (5-7 min). The contents were stirred (3 h) and warmed to ambient temperature (3 h). Water (40 mL) was added and the mixture extracted with EtOAc (4×100 mL). The organic phase was washed with dilute HCl (0.5 N, 30 mL), followed by H$_2$O (30 mL), 1.0 M NaOH (30 mL), NaHCO$_3$ aq (30 mL) and saturated NaCl aq (30 mL). The organic phase was dried (MgSO$_4$), filtered, concentrated under reduced pressure, and purified via SiO$_2$ chromatography (10:1:0.25; Hex:EtOAc:MeOH) to afford 12 a light yellow solid (4.61 g; 16.4 mmol; 96% yield). $^1$H-NMR (400 MHz) CDCl$_3$: 7.86-7.83 (d, 2H), 7.48-7.46 (d, 1H), 7.40-7.38 (d, 1H), 7.29-7.25 (t, 1H), 7.21-7.17 (t, 1H), 6.99-6.94 (d, 2H), 3.89 (s, 3H), 2.94-2.88 (q, 2H), 1.35-1.29 (t, 3H); $^{13}$C-NMR (100 MHz) CDCl$_3$: 190.6, 165.5, 163.6, 153.7, 132.0, 131.8, 127.3, 124.3, 123.5, 121.4, 116.3, 113.8, 111.0, 55.6, 21.8, 12.5. LC/MS-MS: 281.1→135.1 m/z; GS1 and GS2 at 25, DP=66, CE=29, CXP=8, t$_R$=4.73 min.

(2-Ethylbenzofuran-3-yl)(4-hydroxyphenyl)methanone (13): In a RBF/SB (50 mL), benzofuran (12; 1.00 g; 3.57 mmol) was diluted with DMF (18 mL) and NaSEt (455 mg) was added. The mixture was heated (125-130° C.; 1.0 h). Next, the mixture was quenched (2 vol NH$_4$Cl aq) and extracted with EtOAc (4×75 mL) The organic phase was washed with H$_2$O, followed by NaCl aq. The organic phase was then dried (MgSO$_4$), filtered, concentrated under reduced pressure and purified via SiO$_2$ chromatography (4:1; Hex:EtOAc) to give 13 as a white solid (857 mg; 3.22 mmol; 90% yield). $^1$H-NMR (400 MHz) CDCl$_3$: 10.4 (bs, 1H; exchangeable in D$_2$O), 7.80-7.78 (d, 2H), 7.49-7.47 (d, 1H), 7.43-7.41 (d, 1H), 7.30-7.26 (t, 1H), 7.22-7.18 (t, 1H), 6.98-6.94 (d, 2H), 2.95-2.89 (q, 2H), 1.36-1.32 (t, 3H); $^{13}$C-NMR (100 MHz) CDCl$_3$: 192.1, 165.9, 161.5, 153.6, 132.2, 130.9, 129.0, 124.4, 123.5, 121.1, 116.1, 115.6, 111.0, 21.8, 12.2. LC/MS-MS: 267.0→121.2 m/z; GS1 and GS2 at 20, DP=46, CE=29, CXP=6, t$_R$=4.31 min.

(3,5-Dibromo-4-hydroxyphenyl)(2-ethylbenzofuran-3-yl)methanone (7): In a RBF/SB (50 mL), hydroxy-benzofuran (13; 318 mg; 1.19 mmol) was diluted with AA (20 mL) and then Br$_2$ (138 μL) was added. After 15 min, the mixture was quenched with H$_2$O (35 mL) and extracted with EtOAc (3×70 mL). The organic phase was washed NaCl aq (2×50 mL) and dried (MgSO$_4$), filtered, concentrated under reduced pressure, and purified via SiO$_2$ chromatography (3:1; Hex:EtOAc) to give 7 as a light red solid (176 mg; 0.469 mmol; 35% yield). $^1$H-NMR (400 MHz) DMSO-d$_6$: 10.2 (bs, 1H; exchangeable in D$_2$O), 7.91 (s, 2H), 7.66-7.64 (d, 1H), 7.43-7.41 (d, 1H), 7.36-7.33 (t, 1H), 7.29-7.27 (d, 1H), 2.83-2.77 (q, 2H), 1.28-1.24 (t, 3H); $^{13}$C-NMR (100 MHz) DMSO-d$_6$: 187.5, 165.8, 156.1, 153.5, 133.7, 132.3, 126.9, 125.2, 124.3, 121.2, 115.6, 112.2, 111.7, 21.84, 12.4. LC/MS-MS: 424.9→278.8 m/z; GS1 and GS2 at 20, DP=96, CE=37, CXP=16, t$_R$=4.65 min. Alternatively, NBS was used as a brominating agent. In a RBF/SB (50 mL) NBS (0.200 g, 1.13 mmol) mixed in DCM (9.0 mL) was diluted with DMF (0.33 mL) at −10° C. (ice-brine cooling bath) for 10 min. Next, 13 (0.150 g, 0.563 mmol) in DCM (1 mL) was added. The reaction mixture was allowed to warm to RT and stirred (17 h). The reaction mixture was quenched (water; 5 mL) and diluted with DCM (30 mL). The organic phase was washed with water (4 times; 10 mL each) and then brine. The organic phase was dried (Na$_2$SO$_4$), filtered and concentrated under reduced pressure. The crude material was purified twice by column chromatography on SiO$_2$ (Hex:EtOAc; 4:1) to afford 7 (192 mg, 0.460 mmol, 82%) as a white solid.

(2-Ethyl-5-methoxybenzofuran-3-yl)(4-methoxyphenyl) methanone (14), (2-ethyl-5-methoxybenzofuran-4-yl)(4-methoxyphenyl)methanone (15) (2-ethyl-5-methoxybenzofuran-7-yl)(4-methoxyphenyl)methanone (16): Benzofuran (11B; 6.10 g; 34.6 mmol) in a RBF/SB (250 mL) was diluted with CS$_2$ (100 mL). The reaction vessel was capped with a sure-seal and a N$_2$ balloon attached. The RBF was cooled in an ice bath (30 min) and p-anisoyl chloride (1.3 mol equiv.) was added dropwise (3-4 min); next, tin (IV) chloride (1.3 mol equiv.) was added dropwise (5-7 min) and the mixture was stirred (3 h). The contents were warmed to RT (3 h), diluted with H$_2$O (40 mL), and extracted with EtOAc (4×150 mL). The organic phase was washed with dilute HCl (0.5 N, 75 mL), followed by H$_2$O (75 mL), 1.0 M NaOH aq (75 mL), NaHCO$_3$ aq (75 mL) and NaCl aq (75 mL). The organic phase was dried (MgSO$_4$), filtered, concentrated under reduced pressure and purified via SiO$_2$ chromatography (10:1:0.25; Hex:EtOAc:MeOH) to afford three products (14:15:16 in a ratio of 2.6:1.0:6.6). 14: A light yellow oil (1.80 g; 5.80 mmol; 16.8% yield) $^1$H-NMR (400 MHz) CDCl$_3$: 7.86-7.82 (d, 2H), 7.36-7.34 (d, 1H), 6.97-6.93 (m, 3H), 6.88-6.85 (dd, 1H), 3.89 (s, 3H), 3.74 (s, 3H), 2.87-2.79 (q, 2H), 1.32-1.28 (t, 3H); $^{13}$C-NMR (100 MHz) CDCl$_3$: 190.7, 166.1, 163.5, 156.4, 148.7, 131.9, 131.7, 127.9, 116.5, 113.7, 113.0, 111.4, 104.0, 55.9, 55.6, 22.1, 12.4. LC/MS-MS: 311.1-135.1 m/z; GS1 and GS2 at 25, DP=46, CE=29, CXP=8, t$_R$=4.64 min. 15: A light yellow oil (702 mg; 2.26 mmol; 7% yield) $^1$H-NMR (400 MHz) CDCl$_3$: 7.84-7.81 (d, 2H), 7.44-7.41 (d, 1H), 6.92-6.86 (m, 3H), 6.20 (s, 1H), 3.86 (s, 3H), 3.73 (s, 3H), 2.76-2.70 (q, 2H), 1.28-1.23 (t, 3H); $^{13}$C-NMR (100 MHz) CDCl$_3$: 194.3, 163.7, 163.4, 153.1, 149.8, 132.3, 131.1, 129.4, 119.9, 113.6, 112.5, 108.1, 100.7, 57.1, 55.5, 22.0, 11.7. LC/MS-MS: 311.1→203.1 m/z; GS1 and GS2 at 25, DP=41, CE=21, CXP=12, t$_R$=4.48 min. 16: A white solid (4.61 g; 14.9 mmol; 43% yield) $^1$H-NMR (400 MHz) CDCl$_3$: 7.82-7.79 (d, 2H), 7.38 (s, 1H), 6.99 (s, 1H), 6.90-6.87 (d, 2H), 6.37 (s, 1H), 3.86 (s, 3H), 3.73 (s, 3H), 2.82-2.77 (q, 2H), 1.35-1.31 (t, 3H); $^{13}$C-NMR (100 MHz) CDCl$_3$: 194.9, 163.8, 163.5, 153.9, 148.8, 132.4, 131.7, 131.2, 125.2, 113.5, 111.6, 102.4, 101.5, 56.3, 55.5, 22.1, 11.9. LC/MS-MS: 311.1→203.1 m/z; GS1 and GS2 at 25, DP=51, CE=25, CXP=12, t$_R$=4.49 min. Investigating the influence of temperature on product ratio, the ratios of isolated 14:15:16 were 2.6:1.0:6.6 at 5° C. and 1.1:1.0:2.7 at room temperature (RT).

(2-Ethyl-6-methoxybenzofuran-3-yl)(4-methoxyphenyl) methanone (17) and (2-ethyl-6-methoxybenzofuran-4-yl)(4-methoxyphenyl)methanone (18): In a RBF/SB (250 mL), benzofuran (11C, 6.27 g; 35.6 mmol) was diluted with CS$_2$ (100 mL) and the vessel capped with a sure-seal and a N$_2$ balloon attached. The RBF was cooled in an ice bath (30 min) and p-anisoyl chloride (1.3 mol equiv.) was added dropwise (3-4 min); next, tin (IV) chloride (1.3 mol equiv.;

5-7 min) was added. The mixture was stirred (3.0 h) and warmed to RT (3.0 h). The contents were diluted (H$_2$O; 40 mL) and extracted with EtOAc (4×150 mL). The organic phase was washed with dilute HCl (0.5 N, 75 mL), followed by water (75 mL), 1.0 M NaOH (75 mL), NaHCO$_3$ aq (75 mL) and saturated NaCl aq (75 mL). The organic phase was dried (MgSO$_4$), filtered, concentrated under reduced pressure, and purified via SiO$_2$ chromatography (10:1; Hex:EtOAc) to afforded two products (17:18) in a 5.3:1.0 ratio. 17: A light yellow solid (7.92 g; 25.5 mmol; 72% yield). $^1$H-NMR (400 MHz) CDCl$_3$: 7.85-7.81 (d, 2H), 7.27-7.25 (d, 1H), 7.01 (s, 1H), 6.96-6.94 (d, 2H), 6.83-6.80 (d, 1H), 3.89 (s, 3H), 3.84 (s, 3H), 2.89-2.83 (q, 2H), 1.33-1.29 (t, 3H); $^{13}$C-NMR (100 MHz) CDCl$_3$: 190.5, 164.5, 163.5, 158.0, 154.7, 132.1, 131.7, 121.5, 120.6, 116.2, 113.7, 112.1, 95.9, 55.8, 55.5, 21.8, 12.5. LC/MS-MS: 311.1→135.1 m/z; GS1 and GS2 at 25, DP=56, CE=31, CXP=9, t$_R$=4.65 min. 18: A light yellow solid (1.50 g; 4.80 mmol; 14% yield) $^1$H-NMR (400 MHz) CDCl$_3$: 7.81-7.78 (d, 2H), 7.42 (s, 1H), 7.03 (s, 1H), 6.91-6.88 (d, 2H), 6.32 (s, 1H), 3.87 (s, 3H), 3.75 (s, 3H), 2.79-2.75 (q, 2H), 1.34-1.31 (t, 3H); $^{13}$C-NMR (100 MHz) CDCl$_3$: 195.3, 163.4, 161.1, 156.6, 155.2, 132.4, 131.3, 125.2, 121.8, 121.0, 113.5, 100.9, 94.5, 56.1, 55.5, 21.8, 12.0. LC/MS-MS: 311.1→203.1 m/z; GS1 and GS2 at 25, DP=56, CE=25, CXP=14, t$_R$=4.48 min. Investigating the influence of temperature on product ratio, the ratios of isolated 17:18 changed with 5.3:1.0 at 5° C. to 2.6:1.0 at RT.

(2-Ethyl-7-methoxybenzofuran-3-yl)(4-methoxyphenyl)methanone (19) and (2-ethyl-7-methoxybenzofuran-4-yl)(4-methoxyphenyl)methanone (20): In a RBF/SB (100 mL), benzofuran (11D; 3.96 g; 22.5 mmol) was diluted in CS$_2$ (35 mL). The RBF was capped with a sure-seal and a N$_2$ balloon attached. The vessel was cooled in an ice bath (30 min) and p-anisoyl chloride (1.3 mol equiv.) added dropwise (3-4 min); next, tin (IV) chloride (1.3 mol equiv.; 5-7 min) was added. The mixture was stirred (3 h) and warmed to RT (3 h). The contents were diluted (H$_2$O; 40 mL) and extracted with EtOAc (4×100 mL). The organic phase was washed with HCl aq (0.5 N, 40 mL), followed by H$_2$O (40 mL), NaHCO$_3$ aq (40 mL) and NaCl aq (40 mL). The organic phase was dried (MgSO$_4$), filtered, concentrated under reduced pressure, and purified via SiO$_2$ chromatography (10:1; Hex:EtOAc) to afford two products 19:20 1.0:9.7 ratio. 19: A light yellow oil (559 mg; 1.8 mmol; 8% yield) $^1$H-NMR (400 MHz) CDCl$_3$: 7.81-7.78 (d, 2H), 7.51-7.49 (d, 1H), 7.00-6.95 (d, 2H), 6.86 (s, 1H), 6.75-6.72 (d, 1H), 4.07 (s, 3H), 3.87 (s, 3H), 2.85-2.82 (q, 2H), 1.37-1.32 (t, 3H); $^{13}$C-NMR (100 MHz) CDCl$_3$: 194.5, 163.3, 162.8, 148.0, 143.8, 132.2, 131.6, 131.5, 128.5, 123.1, 113.5, 104.3, 102.7, 56.3, 55.5, 21.9, 11.9. LC/MS-MS: 311.0→203.1 m/z; GS1 and GS2 at 25, DP=51, CE=27, CXP=14, t$_R$=4.47 min. 20: A light yellow solid (5.43 g; 17.5 mmol; 78% yield) $^1$H-NMR (400 MHz) CDCl$_3$: 7.83-7.81 (d, 2H), 7.18-7.17 (d, 2H), 6.92-6.90 (d, 2H), 6.43 (s, 1H), 4.04 (s, 3H), 3.87 (s, 3H), 2.87-2.81 (q, 2H), 1.38-1.33 (t, 3H); $^{13}$C-NMR (100 MHz) CDCl$_3$: 194.9, 163.4, 162.8, 145.0, 142.8, 133.8, 132.4, 131.7, 126.0, 124.0, 113.9, 113.4, 101.6, 60.9, 55.5, 21.7, 11.8. LC/MS-MS: 311.1→135.0 m/z; GS1 and GS2 at 25, DP=56, CE=31, CXP=8, t$_R$=4.54 min. Investigating the influence of temperature on product ratio, the ratios of isolated 19:20 changed with reaction temperature from 1.0:9.7 at 5° C. to 1.0:9.0 at RT.

(2-Ethyl-5-methoxybenzofuran-3-yl)(4-hydroxyphenyl)methanone (21): In a RBF/SB (50 mL), benzofuran (15; 1.01 g; 3.25 mmol) was diluted with DMF (15 mL). To the reaction mixture, NaSEt (405 mg) was added and heated (115-120° C.; 0.25 h). The reaction was quenched with the addition of 2 volumes of NH$_4$Cl aq and extracted with EtOAc (4×70 mL). The organic phase was washed with H$_2$O, NaCl aq, dried (MgSO$_4$), filtered, concentrated under reduced pressure, and purified via SiO$_2$ chromatography (4:1; Hex:EtOAc) to afford 21 as a yellow solid (706 mg; 2.38 mmol; 73% yield). $^1$H-NMR (400 MHz) CDCl$_3$: 10.5 (bs, 1H), 7.80-7.77 (d, 2H), 7.37-7.35 (d, 6.95-6.93 (m, 3H), 6.89-6.86 (dd, 1H), 3.73 (s, 3H), 2.89-2.83 (q, 2H), 1.32-1.29 (t, 3H); $^{13}$C-NMR (100 MHz) CDCl$_3$: 191.8, 166.6, 161.1, 156.3, 148.6, 132.1, 131.2, 127.7, 116.3, 115.5, 113.0, 111.4, 104.0, 55.9, 22.0, 12.2. LC/MS-MS: 297.0→121.2 m/z; GS1 and GS2 at 25, DP=41, CE=−31, CXP=6, t$_R$=4.30 min.

(2-Ethyl-5-hydroxybenzofuran-3-yl)(4-methoxyphenyl)methanone (22): In a RBF/SB (50 mL), AlCl$_3$ (0.403 g, 3.03 mmol) and ethanethiol (HSEt; 0.829 mL) were cooled in an ice bath (20 min). Compound 14 (0.20 g, 0.644 mmol) was dissolved in DCM (4.3 mL), added and stirred (1.0 h). Next, the reaction mixture was quenched with 1.0 N HCl, and extracted with DCM (4×75 mL). The organic phase was dried (Na$_2$SO$_4$), filtered, concentrated under reduced pressure, and purified via SiO$_2$ chromatography (Hex:EtOAc; 4:1) to give 22 (0.148 g, 0.499 mmol, 77% yield) as a white solid. $^1$H-NMR (400 MHz) CDCl$_3$: 7.82-7.79 (d, 2H), 7.32-7.30 (d, 1H), 7.22-7.21 (s, 1H), 6.98-6.95 (d, 2H), 6.85-6.82 (d, 1H), 3.88 (s, 31H), 2.79-2.73 (q, 2H), 1.30-1.26 (t, 3H); $^{13}$C-NMR (100 MHz); CDCl$_3$: 191.8, 166.6, 163.5, 153.0, 148.5, 131.8, 131.6, 127.9, 116.3, 113.8, 113.1, 111.3, 106.5, 55.5, 22.1, 12.2. LC/MS-MS: 297.0→135.0 m/z; GS1 and GS2 at 25, CAD=5, DP=66, CE=31, CXP=8, t$_R$=4.25 min.

(2-Ethyl-5-hydroxybenzofuran-3-yl)(4-hydroxyphenyl)methanone (23): In a RBF/SB (50 mL), AlCl$_3$ (0.114 g, 0.857 mmol) and HSEt (0.234 mL) were added. Compound 21 (0.054 g, 0.182 mmol) in DCM (1.3 mL) was added (0° C.) and stirred (1.0 h). The reaction mixture was quenched with H$_2$O/HCl and extracted (DCM; 3×75 mL). The organic phase was washed with NaCl aq, dried (Na$_2$SO$_4$), filtered, concentrated under reduced pressure and purified via SiO$_2$ chromatography (Hex:EtOAc; 4:1) to give 23 (10.3 mg, 0.046 mmol, 25% yield) as a yellow solid. $^1$H-NMR (400 MHz) DMSO-d$_6$: 10.4 (s, 1H), 9.2 (s, 1H), 7.66-7.64 (d, 2H), 7.40-7.37 (d, 1H), 6.88-6.86 (d, 2H), 6.72-6.69 (m, 2H), 2.78-2.72 (q, 2H), 1.22-1.19 (t, 3H); $^{13}$C-NMR (100 MHz) DMSO-d$_6$: 189.9, 165.2, 162.5, 154.3, 147.6, 132.0, 130.3, 128.0, 116.2, 115.7, 113.4, 111.8, 105.9, 21.7, 12.6. LC/MS-MS: 283.1→121.2 m/z; GS1 and GS2 at 25, DP=66, CE=29, CXP=6, t$_R$=3.97 min.

(2-Ethyl-5-methoxybenzofuran-4-yl)(4-hydroxyphenyl)methanone (24): In a RBF/SB (50 mL), 15 (701 mg; 2.26 mmol) was dissolved with DMF (15 mL). NaSEt (285 mg) was added and the mixture was heated (115-120° C.; 0.5 h). Next, the reaction mixture was quenched (2 vol NH$_4$Cl aq) and extracted with EtOAc (4×75 mL). The organic phase was washed with H$_2$O, NaCl aq, dried (MgSO$_4$), filtered, concentrated under reduced pressure, and purified by SiO$_2$ chromatography (4:1; Hex:EtOAc) to afford 24 as a light yellow solid (631 mg; 2.13 mmol; 94% yield). $^1$H-NMR (400 MHz) DMSO-d$_6$: 10.4 (bs, 1H; exchangeable in D$_2$O), 7.59-7.57 (d, 3H), 7.05-7.03 (d, 1H), 6.83-6.81 (d, 2H), 6.19 (s, 1H), 3.67 (s, 3H), 2.75-2.69 (q, 2H), 1.21-1.17 (t, 3H); $^{13}$C-NMR (100 MHz) DMSO-d$_6$: 193.3, 163.4, 162.9, 152.7, 149.4, 132.4, 129.2, 128.5, 120.0, 115.8, 112.7, 108.8, 100.7, 57.0, 21.6, 12.0. LC/MS-MS: 297.0→203.0 m/z; GS1 and GS2 at 20, DP=66, CE=23, CXP=14, t$_R$=4.17 min.

(2-Ethyl-5-hydroxybenzofuran-4-yl)(4-methoxyphenyl)methanone (25) and (2-ethyl-5-hydroxybenzofuran-4-yl)(4-hydroxyphenyl)methanone (26): In a RBF/SB (25 mL), 15 (0.200 g, 0.644 mmol) was dissolved with DMF (4.5 mL). NaSEt (0.270 g, 3.22 mmol) was added and the mixture was heated (110±5° C.; 19 h). The mixture was quenched with NH$_4$Cl aq (2 vol.) and extracted with EtOAc (3×75 mL). The organic phase was washed with NaCl aq, dried (Na$_2$SO$_4$), filtered, concentrated under reduced pressure, and purified via SiO$_2$ chromatography (Hex:EtOAc; 4:1) to give: i) 24 (111.5 mg, 60% yield) as a light yellow solid, ii) 25 (4.8 mg, 0.0161 mmol, 2.5% yield) as a yellow solid, $^1$H-NMR (400 MHz) CDCl$_3$: 11.5 (s, 1H), 7.69-7.66 (d, 2H), 7.52-7.49 (d, 1H), 6.99-6.95 (d, 2H), 6.91-6.89 (d, 1H), 5.60 (s, 1H), 3.91 (s, 3H), 2.68-2.53 (q, 2H), 1.21-1.17 (t, 3H); $^{13}$C-NMR (100 MHz) CDCl$_3$: 199.1, 163.0, 162.3, 159.4, 148.4, 132.2, 131.4, 129.5, 118.3, 113.6, 113.2, 111.8, 102.9, 55.5, 21.8, 11.8. LC/MS-MS: 297.0→189.0 m/z; GS1 and GS2 at 25, CAD=5, DP=71, CE=29, CXP=12, $t_R$=4.80 min and, iii) 26 (8.5 mg, 0.0301 mmol, 5% yield) as a yellow foam. $^1$H-NMR (400 MHz) CDCl$_3$: 11.5 (bs, 1H), 7.65-7.61 (d, 2H), 7.52-7.50 (d, 1H), 6.93-6.89 (m, 3H), 5.60 (s, 1H), 5.24 (bs, 1H), 2.68-2.63 (q, 2H), 1.21-1.17 (t, 3H); $^{13}$C-NMR (100 MHz) CDCl$_3$: 199.1, 162.4, 159.4, 159.3, 148.5, 132.4, 131.6, 129.5, 118.4, 115.2, 113.2, 111.7, 102.8, 21.8, 11.8. LC/MS-MS: 283.1→189.0 m/z; GS1 and GS2 at 25, CAD=5, DP=66, CE=29, CXP=12, $t_R$=4.26 min.

(2-Ethyl-5-methoxybenzofuran-7-yl)(4-hydroxyphenyl)methanone (27): In a RBF/SB (50 mL), 16 (2.17 g; 6.99 mmol) dissolved in DMF (26 mL) was added and stirred. NaSEt (884 mg) was added and heated (100-105° C.; 3.0 h). The reaction mixture was quenched (2 vol NH$_4$Cl aq) and extracted with EtOAc (4×125 mL). The organic phase was washed with H$_2$O, NaCl aq, dried (MgSO$_4$), filtered, concentrated under reduced pressure, and purified via SiO$_2$ chromatography (2:1; Hex:EtOAc) to afford 27 as a light yellow sticky solid (908 mg; 3.06 mmol; 44% yield). $^1$H-NMR (400 MHz) CDCl$_3$: 10.3 (bs, 1H), 7.78-7.75 (d, 2H), 7.39 (s, 1H), 7.02 (s, 1H), 6.87-6.83 (d, 2H), 6.38 (s, 1H), 3.74 (s, 3H), 2.82-2.77 (q, 2H), 1.30-1.26 (t, 3H); $^{13}$C-NMR (100 MHz) CDCl$_3$: 192.0, 165.0, 161.4, 157.8, 154.5, 132.1, 130.9, 121.3, 120.3, 116.0, 115.5, 112.2, 95.7, 55.7, 21.8, 12.3. LC/MS-MS: 297.0→203.1 m/z; GS1 and GS2 at 25, DP=36, CE=27, CXP=14, $t_R$=4.20 min.

(2-Ethyl-5-hydroxybenzofuran-7-yl)(4-methoxyphenyl)methanone (28): In a RBF/SB (25 mL), 16 (0.200 g, 0.644 mmol) was diluted with DMF (4.5 mL) and NaSEt (0.108 g, 1.28 mmol) was added. The mixture was heated (110±5° C., 1.0 h) and then quenched with NH$_4$Cl aq, (2 vol) and extracted with EtOAc (3×75 mL). The organic phase was dried (Na$_2$SO$_4$), filtered, concentrated under reduced pressure and purified via SiO$_2$ chromatography (Hex:EtOAc; 4:1) to give: i) 27 (97.0 mg, 0.327 mmol, 51% yield) as a white solid, and ii) 28 (8.1 mg, 0.027 mmol, 4% yield) as a yellow solid. $^1$H-NMR (400 MHz) CDCl$_3$: 11.9 (s, 1H), 7.74-7.72 (d, 2H), 7.63 (s, 1H), 7.07 (s, 1), 7.02-7.00 (d, 2H), 6.36 (s, 1H), 3.91 (s, 3H), 2.81-2.76 (q, 2H), 1.35-1.31 (t, 3H); $^{13}$C-NMR (100 MHz); CDCl$_3$: 199.9, 167.1, 162.6, 158.9, 147.6, 136.6, 131.6, 130.8, 115.2, 114.3, 113.6, 107.1, 101.6, 55.5, 22.1, 11.5. LC/MS-MS: 297.0→135.0 m/z; GS1 and GS2 at 25, DP=106, CE=33, CXP=8, $t_R$=4.82 min.

(2-Ethyl-5-hydroxybenzofuran-7-yl)(4-hydroxyphenyl)methanone (29): In a RBF/SB (25 mL), 16 (0.200 g, 0.644 mmol) was added and diluted with DMF (4.5 mL). NaSEt (0.270 g, 3.22 mmol) was added and the contents were stirred and heated (110±5° C.; 16 h). Next, the reaction mixture was quenched with NH$_4$Cl aq, and extracted with EtOAc (3×75 mL). The organic phase was washed with NaCl aq, dried (Na$_2$SO$_4$), filtered, concentrated under reduced pressure, and purified via SiO$_2$ chromatography (Hex:EtOAc; 4:1) to give: i) 27 (82.0 mg, 0.276 mmol, 43% yield) as an off-white solid, and ii) 29 (21.3 mg, 0.075 mmol, 12% yield) as a yellow solid. $^1$H-NMR (400 MHz) CDCl$_3$: 11.9 (bs, 2H), 7.69-7.67 (d, 2H), 7.62 (s, 1H), 7.07 (s, 1H), 6.95-6.93 (d, 2H), 6.36 (s, 1H), 2.80-2.78 (q, 2H), 1.35-1.32 (t, 3H); $^{13}$C-NMR (100 MHz) CDCl$_3$: 200.0, 167.2, 159.1, 158.8, 147.6, 136.8, 131.9, 131.0, 115.2, 115.1, 114.4, 107.2, 101.7, 22.1, 11.5. LC/MS-MS: 283.1→121.2 m/z; GS1 and GS2 at 25, DP=61, CE=33, CXP=6, $t_R$=4.37 min.

(2-Ethyl-6-methoxybenzofuran-3-yl)(4-hydroxyphenyl)methanone (30): In a RBF/SB (100 mL), benzofuran (17; 2.00 g; 6.44 mmol) was diluted with DMF (25 mL). The mixture was stirred while NaSEt (820 mg) was added and the contents were warmed (105-110° C.; 1.0 h). The mixture was quenched (2 vol saturated NH$_4$Cl aq) and extracted with EtOAc (4×150 mL). The organic phase was washed with H$_2$O, followed by NaCl aq, and then dried (MgSO$_4$). The material was filtered, concentrated under reduced pressure and purified via SiO$_2$ chromatography (4:1; Hex:EtOAc) to afford 30 as a yellow solid (1.54 g; 5.20 mmol; 81% yield). $^1$H-NMR (400 MHz) CDCl$_3$: 10.3 (bs, 1H), 7.79-7.78 (d, 2H), 7.28-7.26 (d, 1H), 7.02-7.01 (d, 1H), 6.93-6.91 (d, 2H), 6.84-6.82 (dd, 1H), 3.85 (s, 3H), 2.90-2.84 (q, 2H), 1.33-1.29 (t, 3H); $^{13}$C-NMR (100 MHz) CDCl$_3$: 191.8, 165.0, 161.0, 157.9, 154.6, 132.1, 131.2, 121.4, 120.3, 116.0, 115.5, 112.2, 95.8, 55.7, 21.8, 12.4. LC/MS-MS: 297.0→121.2 m/z; GS1 and GS2 at 25, DP=46, CE=27, CXP=6, $t_R$=4.28 min.

(2-Ethyl-6-hydroxybenzofuran-3-yl)(4-methoxyphenyl)methanone (31) and (2-ethyl-6-hydroxybenzofuran-3-yl)(4-hydroxyphenyl)methanone (32): A RBF/SB containing AlCl$_3$ (0.403 g, 3.03 mmol) was cooled with an ice/NaCl bath (10 min) and then HSEt (0.829 mL) was added and mixed. Compound 17 (0.200 g, 0.644 mmol) in DCM (4.3 mL) was added and stirred (1.0 h). Afterwards, the reaction was quenched (1.0 N HCl; 5 mL) and extracted (DCM). The organic phase was washed with NaCl aq, dried (Na$_2$SO$_4$), filtered, concentrated under reduced pressure, and then purified via SiO$_2$ chromatography (Hex:EtOAc; 4:1) to give: i) 31 (107.8 mg, 0.364 mmol, 56% yield) as a yellow foam. $^1$H-NMR (400 MHz) DMSO-d$_6$: 7.86-7.84 (d, 2H), 7.21-7.19 (d, 1H), 7.00 (s, 1H), 6.96-6.94 (d, 2H), 6.79-6.76 (m, 2H), 3.88 (s, 3H), 2.88-2.82 (q, 2H), 1.32-1.28 (t, 3H); $^{13}$C-NMR (100 MHz) DMSO-d$_6$: 191.5, 164.8, 163.6, 154.5, 154.1, 131.8, 131.7, 121.4, 120.2, 116.0, 113.7, 112.6, 98.1, 55.5, 21.7, 12.4. LC/MS-MS: 297.0→135.1 m/z; GS1 and GS2 at 25, CAD=6, DP=66, CE=31, CXP=8, $t_R$=4.24 min; and, ii) 32 (14.7 mg, 0.052 mmol, 8% yield) as a light yellow solid. $^1$H-NMR (400 MHz) DMSO-d$_6$: 10.4 (bs, 1H), 9.6 (bs, 1H), 7.67-7.65 (d, 2H), 7.14-7.12 (d, 1H), 6.94-6.93 (d, 1H), 6.88-6.86 (d, 2H), 6.73-6.71 (d, 1H), 2.75-2.69 (q, 2H), 1.21-1.18 (t, 3H); $^{13}$C-NMR (100 MHz) DMSO-d$_6$: 189.9, 162.8, 162.5, 156.0, 154.6, 132.0, 130.3, 121.3, 119.1, 116.1, 115.7, 113.1, 97.9, 21.6, 12.8. LC/MS-MS: 283.0→121.2 m/z; GS1 and GS2 at 25, CAD=5, DP=41, CE=29, CXP=6, $t_R$=4.45 min.

(2-Ethyl-6-methoxybenzofuran-4-yl)(4-hydroxyphenyl)methanone (33): In a RBF/SB, 18 (700 mg; 2.26 mmol) was diluted with DMF (11.0 mL). To the mixture NaSEt (367 mg) was added and the contents were warmed (105-110° C.; 3.0 h). Afterwards, the reaction was quenched (2 vol NH$_4$Cl aq) and extracted with EtOAc (4×70 mL). The organic phase was washed with H$_2$O, NaCl aq, dried (MgSO$_4$), filtered, concentrated under reduced pressure, and purified via SiO$_2$ chromatography (4:1; Hex:EtOAc) to afford 33 as a yellow solid (308 mg; 1.04 mmol; 46% yield). $^1$H-NMR (400 MHz) DMSO-d$_6$: 10.4 (bs, 1H; exchangeable in D$_2$O), 7.59-7.57 (d, 2H), 7.38 (s, 1H), 7.33 (s, 1H), 6.84-6.82 (d, 2H), 6.53 (s, 1H), 3.70 (s, 3H), 2.84-2.77 (q, 2H), 1.28-1.25 (t, 3H); $^{13}$C-NMR (100 MHz) DMSO-d$_6$: 194.3, 162.6, 160.9, 156.1, 154.9, 132.5, 129.5, 125.8, 121.7, 120.3, 115.6, 101.5, 95.7, 56.5, 21.6, 12.2. $^1$H-NMR (400 MHz) CDCl$_3$: 7.79-7.77 (d, 2H), 7.28-7.26 (d, 1H), 7.21 (bs, 1H; exchangeable in D$_2$O), 7.02-7.01 (d, 1H), 6.93-6.91 (d, 2H), 6.84-6.81 (dd, 1H), 3.85 (s, 3H), 2.90-2.84 (q, 2H), 1.33-1.29 (t, 3H); $^{13}$C-NMR (100 MHz) CDCl$_3$: 191.5, 165.0, 160.8, 157.9, 154.6, 132.1, 131.5, 121.4, 120.4, 116.0, 115.4, 112.2, 95.8, 55.8, 21.8, 12.4. LC/MS-MS: 297.0→121.2 m/z; GS1 and GS2 at 20, DP=41, CE=29, CXP=6, t$_R$=4.27 min.

(2-Ethyl-6-hydroxybenzofuran-4-yl)(4-methoxyphenyl) methanone (34) and (2-ethyl-6-hydroxybenzofuran-4-yl)(4-hydroxyphenyl)methanone (35): In a RBF/SB (15 mL), 18 (0.200 g, 0.644 mmol) was diluted with DMF (3.0 mL). To the mixture NaSEt (0.108 g, 1.29 mmol) was added and the contents were heated (110±5° C.; 4.0 h). Additional NaSEt (0.108 g, 1.29 mmol) was added and heated (14 h). Next, the reaction was quenched with NH$_4$Cl aq and extracted with EtOAc (3×40 mL). The organic phase was washed with NaCl aq (2 vol), dried (Na$_2$SO$_4$), filtered, concentrated under reduced pressure, and purified via SiO$_2$ chromatography (Hex:EtOAc; 4:1) to give: i) 33 (98.0 mg, 0.330 mmol, 51% yield) as a white solid, ii) 34 (21.7 mg, 0.0732 mmol, 11% yield) as a yellow solid. $^1$H-NMR (400 MHz) CDCl$_3$: 12.2 (bs, 2H), 7.73-7.69 (m, 3H), 7.04 (s, 1H), 7.02-6.99 (d, 2H), 6.25, (s, 1H), 3.91 (s, 3H), 2.77-2.75 (q, 2H), 1.33-1.30 (t, 3H); $^{13}$C-NMR (100 MHz) CDCl$_3$: 200.2, 162.7, 161.9, 161.0, 159.2, 131.7, 131.0, 125.4, 121.5, 116.1, 113.6, 100.8, 99.5, 55.5, 21.7, 11.7. LC/MS-MS: 297.0→135.1 m/z; GS1 and GS2 at 25, DP=61, CE=29, CXP=8, t$_R$=4.90 min; and, iii) 35 (5.7 mg, 0.020 mmol, 3% yield) as a yellow solid. $^1$H-NMR (400 MHz) CDCl$_3$: 12.1 (bs, 2H), 7.70 (s, 1H), 7.69-7.65 (d, 2H), 7.05 (s, 1H), 6.96-6.93 (d, 2H), 6.26 (s, 1H), 2.79-2.73 (q, 2H), 1.33-1.30 (t, 3H); $^{13}$C-NMR (100 MHz) CDCl$_3$: 200.2, 161.9, 161.0, 159.3, 158.9, 132.0, 131.3, 125.4, 121.5, 116.1, 115.2, 100.8, 99.5, 21.7, 11.7. LC/MS-MS: 283.1→121 m/z; GS1 and GS2 at 25, DP=46, CE=31, CXP=6, t$_R$=4.44 min.

(2-Ethyl-7-hydroxybenzofuran-3-yl)(4-methoxyphenyl) methanone (36): In a RBF/SB, 19 (0.100 g, 0.322 mmol) was diluted with DMF (3.0 mL) and NaSEt (0.081 g, 0.966 mmol) was added and heated (105-115° C.; 21 h). The reaction was quenched with NH$_4$Cl aq (2 vol) and extracted with EtOAc (3×75 mL). The organic phase was washed with NaCl aq, dried (Na$_2$SO$_4$), filtered, concentrated under reduced pressure, and purified via SiO$_2$ chromatography (Hex:EtOAc; 4:1) to give 36 (22 mg, 0.074 mmol, 23% yield) as a light yellow solid. $^1$H-NMR (400 MHz) CDCl$_3$: 12.9 (s, 1H), 7.74-7.71 (d, 2H), 7.46-7.43 (d, 2H), 7.01-6.99 (d, 2H), 6.97-6.94 (d, 1H), 6.42 (s, 1H), 3.90 (s, 3H), 2.91-2.85 (q, 2H), 1.39-1.36 (t, 3H); $^{13}$C-NMR (100 MHz) CDCl$_3$: 200.3, 165.7, 162.6, 149.5, 142.7, 136.5, 131.7, 131.0, 127.5, 114.7, 113.6, 110.1, 102.2, 55.5, 22.1, 11.8. LC/MS-MS: 296.8→135.1 m/z; GS1 and GS2 at 25, CAD=4, DP=56, CE=39, CXP=10, t$_R$=4.76 min.

(2-Ethyl-7-hydroxybenzofuran-4-yl)(4-methoxyphenyl) methanone (37): In a RBF/SB (50 mL), 20 (548 mg; 1.77 mmol) was diluted with DMF (8.0 mL) NaSEt (224 mg) was added and warmed (80-85° C.; 20 min). The reaction mixture was quenched with 1.2 vol NH$_4$Cl aq and extracted with EtOAc (3×50 mL). The organic phase was washed with NaCl aq (40 mL) and dried (MgSO$_4$), filtered, concentrated under reduced pressure, and purified via SiO$_2$ chromatography (3:1; Hex:EtOAc) to give 37 as an off-white solid (451 mg; 1.52 mmol; 86% yield). $^1$H-NMR (400 MHz) DMSO-d$_6$: 10.9 (s, 1H; exchangeable in D$_2$O), 7.70-7.67 (d, 2H), 7.36-7.34 (d, 1H), 7.08-7.06 (d, 2H), 6.82 (s, 1H), 6.76-6.74 (d, 1H), 3.85 (s, 3H), 2.85-2.80 (q, 2H), 1.32-1.26 (t, 3H); $^{13}$C-NMR (100 MHz) DMSO-d$_6$: 193.4, 162.9, 162.5, 146.6, 143.1, 131.9, 131.6, 131.5, 129.1, 121.0, 114.0, 109.3, 102.8, 55.8, 21.5, 12.1. LC/MS-MS: 297.0→135.1 m/z; GS1 and GS2 at 25, DP=41, CE=29, CXP=8, t$_R$=4.19 min.

(2-Ethyl-7-hydroxybenzofuran-4-yl)(4-hydroxyphenyl) methanone (38): In a RBF/SB (100 mL), 20 (1.38 g; 4.46 mmol) was dissolved with DMF (20 mL). NaSEt (1.13 g) was added and warmed (105-110° C.; 4.5 h). The mixture was then quenched with 2 vol NH$_4$Cl aq and extracted with EtOAc (4×100 mL). The organic phase was dried (MgSO$_4$), filtered, concentrated under reduced pressure and purified via SiO$_2$ chromatography (2:1; Hex:EtOAc) to give 38 as an off-white solid (1.17 g; 4.14 mmol; 93% yield). $^1$H-NMR (400 MHz) DMSO-d$_6$: 10.9 (bs, 1H-1; exchangeable in D$_2$O), 10.3 (bs, 1H; exchangeable in D$_2$O), 7.61-7.59 (d, 2H, 7.35-7.30 (d, 1H), 6.89-6.86 (d, 2H), 6.79 (s, 1H), 6.75-6.73 (d, 1H), 2.86-2.79 (q, 2H), 1.29-1.25 (t, 3H); $^{13}$C-NMR (100 MHz) DMSO-d$_6$: 193.5, 162.9, 161.6, 146.6, 143.3, 132.5, 131.7, 130.2, 129.0, 121.4, 115.5, 109.4, 103.0, 21.7, 12.3. LC/MS-MS: 283.1→121.2 m/z; GS1 and GS2 at 25, DP=51, CE=29, CXP=6, t$_R$=3.89 min.

(3,5-Dibromo-4-hydroxyphenyl)(2-ethyl-5-methoxybenzofuran-3-yl)methanone (39): In a RBF/SB, NBS (0.180 g, 1.05 mmol) in DCM (8.0 mL) was added. Next, DMF (0.3 mL) was added and the mixture was cooled (ice-brine cooling bath; 10 min). Compound 21 (0.150 g, 0.506 mmol) in DCM (1.0 mL) was added. The mixture was then warmed to RT and stirred (17 h). The mixture was quenched with H$_2$O (10 mL), diluted with DCM (20 mL) and the organic phase was washed four times with H$_2$O, NaCl aq, and then dried (Na$_2$SO$_4$), filtered, concentrated under reduced pressure, and purified via SiO$_2$ chromatography (Hex:EtOAc; 4:1) to give 39 (0.050 g, 0.110 mmol, 22% yield) as a light orange solid. $^1$H-NMR (400 MHz) CDCl$_3$: 8.00 (s, 2H), 7.39-7.36 (d, 1H), 6.93-6.89 (m, 2H), 6.43 (bs, 1H), 3.77 (s, 31-1), 2.89-2.83 (q, 2H), 1.36-1.32 (t, 3H); $^{13}$C-NMR (100 MHz) CDCl$_3$: 187.7, 167.2, 156.7, 153.1, 148.7, 133.7, 133.5, 127.1, 115.6, 113.6, 111.6, 110.0, 103.5, 55.9, 22.2, 12.2. LC/MS-MS: 454.9→278.8 m/z; GS1 and GS2 at 25, CAD=4, DP=71, CE=37, CXP=18, t$_R$=4.59 min.

(3,5-Dibromo-4-hydroxyphenyl)(2-ethyl-5-hydroxybenzofuran-3-yl)methanone (40): AlCl$_3$ (0.041 g, 0.310 mmol) was added dropwise at −10° C. to ethanethiol (0.084 mL). This solution was added to a solution of 39 (39.0 mg, 0.066 mmol) in DCM (1.0 mL) at 0° C. The reaction mixture was stirred at this temperature for 1.0 h and then quenched by the addition of water and 1.0 N HCl. The aqueous phase was extracted with DCM (3×30 mL) and the combined organic layers were washed with brine, dried (Na$_2$SO$_4$), filtered and concentrated in vacuo. The crude material was purified by column chromatography on SiO$_2$ (hexanes:EtOAc, 4:1) to give 40 as a white solid (11.0 mg, 0.025 mmol, 38% yield). $^1$H-NMR (400 MHz) CDCl$_3$: 9.26 (s, 1H; exchangeable D$_2$O), 7.88 (s, 2H), 7.42-7.40 (d, 1H), 6.74-6.73 (bd, 2H; 1 exchangeable in D$_2$O), 2.78-2.72 (q, 2H), 1.25-1.21 (t, 3H); $^{13}$C-NMR (100 MHz) CDCl$_3$: 187.7, 166.5, 154.5, 147.6, 133.6, 127.6, 115.6, 113.7, 112.1, 112.0, 110.0, 109.0, 105.8, 21.9, 12.5. LC/MS-MS: 440.9→278.9 m/z; GS1 and GS2 at 25, CAD=4, DP=121, CE=39, CXP=16, t$_R$=4.31 min.

(3,5-Dibromo-4-hydroxyphenyl)(2-ethyl-5-methoxybenzofuran-4-yl)methanone (41): In a RBS/SB, NBS (0.168 g, 0.945 mmol) in DCM (7.4 mL) was added. Next, DMF (0.28 mL) was added and the mixture was cooled in an ice bath (10 min). Compound 24 (0.140 g, 0.472 mmol) in DCM (1.0 mL) was added and warmed to RT (17 h). The reaction mixture was quenched with $H_2O$ and washed with NaCl aq. The organic phase was dried ($Na_2SO_4$), filtered, concentrated under reduced pressure, and purified via $SiO_2$ chromatography (Hex:EtOAc; 4:1) to give 41 (0.110 g, 0.242 mmol, 51% yield) as a white solid. $^1$H-NMR (400 MHz) $CDCl_3$: 7.94 (s, 2H), 7.49-7.47 (d, 1H), 6.89-6.87 (d, 1H), 6.30 (s, 1H), 3.73 (s, 3H), 2.79-2.74 (q, 2H), 1.31-1.28 (t, 3H); $^{13}$C-NMR (100 MHz) $CDCl_3$: 191.8, 164.0, 153.5, 153.0, 149.8, 133.8, 133.1, 129.8, 117.9, 113.6, 109.7, 107.7, 100.7, 56.7, 21.9, 11.6. LC/MS-MS: 454.9→203.2 m/z; GS1 and GS2 at 25, CAD=4, DP=26, CE=33, CXP=14, $t_R$=4.42 min.

(3,5-Dibromo-4-hydroxyphenyl)(2-ethyl-5-hydroxybenzofuran-4-yl)methanone (42): $AlCl_3$ (0.065 g, 0.486 mmol) was added dropwise at −10° C. to ethanethiol (0.133 mL). This solution was added to a solution of 41 (47.0 mg, 0.103 mmol) in DCM (1.0 mL) at 0° C. The reaction mixture was stirred at this temperature for 1.0 h and then quenched by the addition of water and 1.0 N HCl. The aqueous phase was extracted with DCM (3×30 mL) and the combined organic layers were washed with brine, dried ($Na_2SO_4$), filtered and concentrated in vacuo. The crude material was purified by column chromatography on $SiO_2$ (hexanes:EtOAc, 4:1) to give 42 as a yellow solid (15.2 mg, 0.0345 mmol, 33% yield). $^1$H-NMR (400 MHz) $CDCl_3$: 11.4 (s, 1H), 7.84 (s, 2H), 7.57-7.54 (d, 1H), 6.92-6.89 (d, 1H), 5.64 (s, 1H), 2.72-2.67 (q, 2H), 1.24-1.21 (t, 3H); $^{13}$C-NMR (100 MHz) $CDCl_3$: 195.9, 163.2, 159.9, 152.7, 148.5 133.9, 133.3, 129.2, 119.3, 113.4, 110.8, 109.8, 102.4, 21.8, 12.0. LC/MS-MS: 441.0→189.0 m/z; GS1 and GS2 at 25, CAD=4, DP=76, CE=39, CXP 12, $t_R$=4.57 min.

(3,5-Dibromo-4-hydroxyphenyl)(2-ethyl-5-methoxybenzofuran-7-yl)methanone (43): In a RBS/SB, NBS (0.180 g, 1.05 mmol) in DCM (8.0 mL) was added. Next, DMF (0.3 mL) was added and the mixture was cooled in an ice bath (10 min). Compound 27 (0.150 g, 0.506 mmol) in DCM (1.0 mL) was added and warmed to RT (17 h). The mixture was diluted with $H_2O$, diluted with DCM (20 mL) and the organic phase was washed four times with $H_2O$ and then NaCl aq. The organic phase was dried ($Na_2SO_4$), filtered, concentrated under reduced pressure and purified via $SiO_2$ chromatography (Hex:EtOAc; 4:1) to give 43 (145 mg, 0.319 mmol, 63% yield) as a white solid. $^1$H-NMR (400 MHz) $CDCl_3$: 7.92 (s, 2H), 7.43 (s, 1H), 7.03 (s, 1H), 6.40 (s, 1H), 3.74 (s, 3H), 2.84-2.78 (q, 2H), 1.36-1.33 (t, 3H); $^{13}$C-NMR (100 MHz) $CDCl_3$: 192.4, 164.5, 153.9, 152.8, 148.8, 133.9, 133.2, 132.7, 123.4, 111.9, 109.6, 102.4, 101.5, 56.1, 22.0, 11.7. LC/MS-MS: 454.9→203.2 m/z; GS1 and GS2 at 25, CAD=4, DP=86, CE=35, CXP=12, $t_R$=4.47 min.

(3,5-Dibromo-4-hydroxyphenyl)(2-ethyl-5-hydroxybenzofuran-7-yl)methanone (44): $AlCl_3$ (0.117 g, 0.880 mmol) and ethanethiol (0.241 mL) were mixed in a RBF/SB and cooled with an ice bath. Next, compound 43 (0.085 g, 0.187 mmol) in DCM (1.3 mL) was added and stirred (1.0 h). The mixture was quenched with $H_2O$/1.0 N HCl (1 vol) and extracted with DCM (3×30 mL). The organic phase was dried ($Na_2SO_4$), filtered, concentrated under reduced pressure and purified via $SiO_2$ chromatography (Hex:EtOAc; 4:1) to give 44 (53.9 mg, 0.122 mmol, 65% yield) as a yellow solid. $^1$H-NMR (400 MHz) DMSO-$d_6$: 10.9 (bs, 1H), 10.2 (s, 1H), 7.80 (s, 2H), 7.47 (s, 1H), 7.02 (s, 1H), 6.57 (s, 1H), 2.80-2.74 (q, 2H), 1.27-1.23 (t, 3H); $^{13}$C-NMR (100 MHz) DMSO-$d_6$: 193.9, 165.4, 155.1, 153.7, 148.0, 134.3, 134.0, 132.2, 120.2, 112.3, 111.8, 106.8, 102.1, 21.8, 12.0. LC/MS-MS: 441.0→189.0 m/z; GS1 and GS2 at 25, CAD=4, DP=60, CE=37, CXP=18, $t_R$=4.81 min.

(3,5-Dibromo-4-hydroxyphenyl)(2-ethyl-6-methoxybenzofuran-3-yl)methanone (45): In a RBF/SB (50 mL), NBS (0.180 g, 1.05 mmol) in DCM (8.0 mL) was added and followed by the addition of DMF (0.3 mL). The mixture was cooled in an ice/NaCl bath (10 min), and then benzofuran (30; 0.150 g, 0.506 mmol) in DCM (1.0 mL) was added. The mixture was warmed to RT (20 h) and then quenched with water (5 mL) and diluted with additional DCM (10 mL). The material was washed with $H_2O$ (10 mL) and then with NaCl aq (10 mL). The organic phase was dried ($Na_2SO_4$), filtered, concentrated under reduced pressure and purified via $SiO_2$ chromatography (Hex:EtOAc; 4:1) to give 45 (0.148 g, 0.326 mmol, 64% yield) as a light yellow solid. $^1$H-NMR (400 MHz) DMSO-$d_6$: 11.0 (s, 1H), 7.90 (s, 2H), 7.29-7.27 (m, 2H), 6.91-6.88 (d, 1H), 3.80 (s, 3H), 2.78-2.73 (q, 2H), 1.26-1.25 (t, 3H); $^{13}$C-NMR (100 MHz) DMSO-$d_6$: 187.6, 164.9, 158.2, 154.6, 133.6, 132.2, 121.4, 119.8, 115.4, 113.0, 112.0, 96.6, 56.2, 21.8, 12.5. LC/MS-MS: 454.9→278.8 m/z; GS1 and GS2 at 25, CAD=5, DP=76, CE=35, CXP=18, $t_R$=4.58 min.

6-Hydroxy-Benzbromarone (8); (3,5-dibromo-4-hydroxyphenyl)(2-ethyl-6-hydroxy-benzofuran-3-yl)methanone: In a RBF/SB cooled with an ice/NaCl bath, ethanethiol (HSEt; 1.29 mL) was added followed by $AlCl_3$ (0.414 g, 3.11 mmol). Compound 45 (0.300 g, 0.661 mmol) in DCM (10 mL) was added and stirred (1.5 h). Afterwards, the reaction mixture was quenched with 1.0 N HCl (5 mL) and extracted with DCM (3×40 mL). The organic phase was washed with NaCl aq, and then dried ($Na_2SO_4$), filtered, concentrated under reduced pressure, and purified via $SiO_2$ chromatography (Hex:EtOAc; 4:1) to give 8 (226 mg, 0.514 mmol, 78% yield) as a light brown foam. $^1$H-NMR (400 MHz) DMSO-$d_6$: 10.9 (bs, 1H), 9.7 (s, 1H), 7.88 (s, 2H), 7.19-7.17 (d, 1H), 6.95 (s, 1H), 6.75-6.72 (d, 2H), 2.74-2.69 (q, 2H), 1.23-1.19 (t, 3H); $^{13}$C-NMR (100 MHz); DMSO-$d_6$: 187.7, 164.4, 156.2, 155.4, 154.7, 133.6, 133.0, 121.4, 118.6, 115.5, 113.4, 112.0, 98.0, 21.8, 12.6. LC/MS-MS: 441.0→278.9 m/z; GS1 and GS2 at 25, CAD=4, DP=101, CE=35, CXP=18, $t_R$=4.20 min.

(5-Bromo-2-ethyl-6-methoxybenzofuran-3-yl)(3,5-dibromo-4-hydroxyphenyl)methanone (46): In a RBF/SB, NBS (0.270 g, 1.52 mmol) in DCM (3.9 mL) was diluted with DMF (0.3 mL) and cooled in an ice bath (10 min). Compound 30 (0.150 g, 0.506 mmol) dissolved in DCM (1.0 mL) was added and the reaction mixture was warmed up to RT (17 h). The mixture was quenched with $H_2O$ (1 vol) and diluted with DCM (30 ml). The organic phase was washed four times with $H_2O$, and then NaCl aq. The organic phase was dried ($Na_2SO_4$), filtered, concentrated under reduced pressure and purified via $SiO_2$ chromatography (Hex:EtOAc; 4:1) to give 46 (0.146 g, 0.274 mmol 54% yield) as an off-white solid. $^1$H-NMR (400 MHz) DMSO-$d_6$: 11.1 (bs, 1H), 7.91 (s, 2H), 7.60 (s, 1H), 7.51 (s, 1H), 3.90 (s, 3H), 2.76-2.71 (q, 2H), 1.25-1.24 (t, 3H); $^{13}$C-NMR (0.100 MHz) DMSO-$d_6$: 187.2, 165.7, 155.6, 153.8, 153.7, 133.7, 132.6, 124.3, 121.0, 114.9, 112.0, 107.5, 97.0, 57.3, 22.0, 12.4. LC/MS-MS: 532.9→453.9 m/z (M-Br); GS1 and GS2 at 25, CAD=5, DP=70, CE=31, CXP=30, $t_R$=4.70 min.

(6-Bromo-2-ethyl-7-hydroxybenzofuran-4-yl)(3,5-dibromo-4-hydroxyphenyl)methanone (47): In a RBF/SB, NBS (0.189 g, 1.06 mmol) diluted with DCM (9.0 mL) was mixed with DMF (0.31 mL) and the mixture cooled in an ice bath (10 min). Compound 38 (0.150 g, 0.531 mmol) in DCM (1.0 mL) was added and warmed to RT (17 hr). The reaction mixture was quenched with H$_2$O and diluted with DCM (30 mL). The organic phase was washed four times with H$_2$O, NaCl aq, and then dried (Na$_2$SO$_4$), filtered, concentrated under reduced pressure, and purified twice via SiO$_2$ chromatography (Hex:EtOAc; 4:1) to give 47 (125 mg, 0.241 mmol, 45% yield) as a white solid. $^1$H-NMR (400 MHz) CDCl$_3$: 7.91 (s, 2H), 7.62 (s, 1H), 6.77 (s, 1H), 6.20 (bs, 2H), 2.88-2.82 (q, 2H), 1.38-1.34 (t, 3H); $^{13}$C-NMR (100 MHz) CDCl$_3$: 190.4, 164.7, 152.8, 142.5, 141.7, 133.8, 132.9, 131.7, 130.1, 122.1, 109.9, 103.1, 102.7, 21.9, 11.7. LC/MS-MS: 520.9 (M+2, isotope mass→278.8 m/z; GS1 and GS2 at 25, CAD=4, DP=101, CE=37, CXP=18, $t_R$=4.36 min. LC/MS-MS: 454.9→135.1 m/z; GS1 and GS2 at 25, CAD=4, DP=61, CE=37, CXP=8, $t_R$=4.56 min.

(4,6-Dibromo-2-ethyl-5-hydroxybenzofuran-3-yl)(4-methoxyphenyl)methanone (48): In a RBF/SB, NBS (0.036 g, 0.203 mmol) diluted with DCM (1.0 mL) was mixed with DMF (0.06 mL) and the mixture cooled in an ice bath (10 min). Compound 22 (0.030 g, 0.101 mmol) in DCM (0.8 mL) was added and warmed to RT (18 hr). The reaction mixture was quenched with H$_2$O and diluted with DCM (30 mL). The organic phase was washed four times with H$_2$O, NaCl aq, and then dried (Na$_2$SO$_4$), filtered, concentrated under reduced pressure, and purified twice via SiO$_2$ chromatography (Hex:EtOAc; 4:1) to give 48 (7.9 mg, 0.0174 mmol, 17% yield) as an orange oil. $^1$H-NMR (400 MHz) CDCl$_3$: 7.85-7.83 (d, 2H), 7.65 (s, 6.95-6.92 (d, 2H), 5.77 (s, 1H), 3.88 (s, 3H), 2.72-2.66 (q, 2H), 1.27-1.23 (t, 3H); $^{13}$C-NMR (100 MHz) CDCl$_3$: 189.9, 164.1, 162.5, 147.9, 146.1, 132.0, 128.0, 116.6, 114.3, 114.1, 114.0, 105.8, 99.6, 55.5, 21.2, 12.2.

(5,7-Dibromo-2-ethyl-6-hydroxybenzofuran-3-yl)(4-methoxyphenyl)methanone (49): In a RBF/SB, NBS (0.060 g, 0.337 mmol) diluted in DCM (2.0 mL) was mixed with DMF (0.1 mL) and the mixture was cooled in an ice bath (10 min). Compound 31 (0.050 g, 0.169 mmol) in DCM (1.0 mL) was added and the mixture was warmed to RT (17 h). Next, the mixture was quenched with water and diluted with DCM (30 mL). The organic phase was washed four times with H$_2$O, NaCl aq, and then dried (Na$_2$SO$_4$), filtered, concentrated under reduced pressure, and purified via SiO$_2$ chromatography (Hex:EtOAc; 4:1) to give 49 (27.0 mg, 0.0594 mmol, 35% yield) as a yellow oil. $^1$H-NMR (400 MHz) CDCl$_3$: 7.82-7.80 (d, 2H), 7.57 (s, 1H), 6.99-6.97 (d, 2H), 5.93 (bs, 1H), 3.91 (s, 3H), 2.88-2.82 (q, 2H), 1.35-1.31 (t, 3H); $^{13}$C-NMR (100 MHz) CDCl$_3$: 189.5, 165.4, 163.8, 151.1, 146.9, 131.6, 131.3, 122.8, 122.1, 116.2, 113.9, 106.1, 91.8, 55.6, 21.9, 12.3. LC/MS-MS: 454.9→135.1 m/z; GS1 and GS2 at 25, CAD=4, DP=71, CE=37, CXP=8, $t_R$=4.56 min.

(6-Bromo-2-ethyl-7-hydroxybenzofuran-4-yl)(4-methoxyphenyl)methanone (50): In a RBF/SB, compound 37 (203 mg; 0.685 mmol) was diluted with AA (12 mL) and stirred. Next, water (250 μL) followed by Br$_2$ (74 μL) were added. The mixture was stirred (5 min) and quenched with H$_2$O (5 mL) and the mixture was extracted with EtOAc (3×50 mL). The organic phase was dried (MgSO$_4$), filtered, concentrated under reduced pressure, and purified via SiO$_2$ chromatography (3:1; Hex:EtOAc) to afford 50 as a light red solid (176 mg; 0.469 mmol; 69% yield). $^1$H-NMR (400 MHz) CDCl$_3$: 7.81-7.78 (d, 2H), 7.64 (s, 1H), 6.99-6.96 (d, 2H), 6.78 (s, 1H), 6.00 (bs, 1H), 3.90 (s, 3H), 2.86-2.80 (q, 2H), 2.10 (s, 1H), 1.35-1.29 (t, 3H); $^{13}$C-NMR (100 MHz) CDCl$_3$: 193.6, 164.1, 163.2, 142.7, 141.5, 132.4, 131.6, 130.8, 130.4, 123.2, 113.9, 103.0, 102.9, 55.6, 21.9, 11.8. LC/MS-MS: 375.0→135.0 m/z; GS1 and GS2 at 25, DP=66, CE=27, CXP=8, $t_R$=4.42 min.

(2-Ethylbenzofuran-3-yl)(phenyl)methanone (51): In a RBF/SB, benzofuran (0.200 g, 1.37 mmol) was weighed out. The material was diluted in CS$_2$ (4.0 mL), capped and a N$_2$ balloon attached. The contents were stirred and cooled in an ice bath (30 min). Next benzoyl chloride (0.21 mL, 1.78 mmol) was added drop-wise; next tin (IV) chloride (0.21 mL, 1.78 mmol) was added drop-wise. The contents were stirred (3 h) and then allowed to slowly warm to RT (21 h). The reaction mixture was diluted with water and extracted with EtOAc (4×20 mL). The combined organic layer was washed with HCl (0.5 N, 3 mL), water, NaHCO$_3$, and brine. The organic phase was dried (Na$_2$SO$_4$), filtered, concentrated under reduced pressure, and purified via SiO$_2$ chromatography (100% Hex to 5% EtOAc in Hex) to give 51 (220 mg, 0.879 mmol, 64% yield). $^1$H-NMR (400 MHz) CDCl$_3$: 7.84-7.82 (d, 2H), 7.63-7.59 (t, 1H), 7.51-7.47 (m, 3H), 7.39-7.37 (d, 1H), 7.31-7.26 (t, 1H), 7.21-7.17 (t, 1H), 2.94-2.88 (q, 2H), 1.36-1.32 (t, 3H); $^{13}$C-NMR (100 MHz) CDCl$_3$: 192.0, 166.5, 153.7, 139.4, 132.6, 129.1, 128.4, 127.0, 124.3, 123.5, 121.4, 116.1, 110.9, 21.8, 12.3. LC/MS-MS: 251.1→105.0 m/z; GS1 and GS2 at 25, DP=56, CE=29, CXP=6, $t_R$=4.99 min.

(2-Ethylbenzofuran-3-yl)(4-fluorophenyl)methanone (52): In a RBF/SB, benzofuran (0.200 g, 1.37 mmol) was weighed out. The material was diluted in CS$_2$ (4.0 mL), capped and a N$_2$ balloon was attached. The contents were stirred and cooled in an ice bath (30 min). Next 4-fluorobenzoyl chloride (0.21 mL, 1.78 mmol) was added drop-wise; next tin (IV) chloride (0.21 mL, 1.78 mmol) was added drop-wise. The contents were stirred (3 h) and then allowed to slowly warm to RT (3 d). The reaction mixture was diluted with water and extracted with EtOAc (4×20 mL). The combined organic layer was washed with HCl (0.5 N, 3 mL), water, NaHCO3 and brine. The organic layer was dried (Na$_2$SO$_4$), filtered and concentrated under reduced pressure. The crude material was purified by column chromatography on SiO$_2$ (100% Hex to 5% EtOAc in Hex) to give 52 (160 mg, 0.60 mmol, 43%) as a orange oil. $^1$H-NMR (400 MHz) CDCl$_3$: 7.88-7.84 (t, 2H), 7.49-7.47 (d, 1H), 7.33-7.25 (m, 2H), 7.21-7.13 (m, 3H), 2.94-2.89 (q, 2H), 1.35-1.32 (t, 3H); $^{13}$C-NMR (100 MHz) CDCl$_3$: 190.3, 166.8, 166.4, 164.3, 153.7, 135.6, 131.8, 126.8, 124.4, 123.6, 121.2, 115.8, 111.1, 21.8, 12.3. LC/MS-MS: 269.0→123.1 m/z; GS1 and GS2 at 25, DP=61, CE=29, CXP=6, $t_R$=4.85 min.

4-(2-Ethylbenzofuran-3-carbonyl)benzonitrile (53): In a RBF/SB, benzofuran (0.170 g, 1.16 mmol) was weighed out. The material was diluted in CS$_2$ (3.5 mL), capped and a N$_2$ balloon was attached. The contents were stirred and cooled in an ice bath (30 min). Next 4-cyanobenzoyl chloride (0.250 g, 1.51 mmol) was added; next tin (IV) chloride (0.19 mL, 1.51 mmol) was added drop-wise. The contents were stirred (3 h) and then allowed to slowly warm to RT (3 d). The reaction mixture was diluted with water and extracted with EtOAc (4×20 mL). The combined organic layer was washed with HCl (0.5 N, 3 mL), water, NaHCO$_3$ and brine. The organic layer was dried (Na$_2$SO$_4$), filtered and concentrated under reduced pressure. The crude material was purified by column chromatography on SiO$_2$ (100% Hex to 5% EtOAc in Hex) to give 53 (16.6 mg, 0.060 mmol, 5% yield) as a yellow oil. $^1$H-NMR (400 MHz) CDCl$_3$: 7.92-7.89 (d, 2H), 7.81-7.79 (d, 2H), 7.52-7.50 (d, 1H), 7.33-7.29 (t, 1H), 7.25-7.20 (m, 2H), 2.96-2.90 (q, 2H), 1.37-1.33 (t, 3H); $^{13}$C-NMR (100 MHz) CDCl$_3$: 190.2, 167.8, 153.7, 142.9, 132.4, 129.4, 126.2, 124.8, 123.9, 121.0, 118.0, 115.9, 115.4, 111.3, 22.0, 12.2. LC/MS-MS: 276.0→123.0 m/z; GS1 and GS2 at 25, DP=71, CE=27, CXP=8, $t_R$=4.57 min.

(2-Ethylbenzofuran-3-yl)(3-fluoro-4-methoxyphenyl)methanone (54): In a RBF/SB, benzofuran (0.200 g, 1.37 mmol) was weighed out. The material was diluted in $CS_2$ (4.0 mL), capped and a nitrogen balloon was attached. The contents were stirred and cooled in an ice bath (30 min). Next 3-fluoro-4-methoxybenzoyl chloride (0.335 g mL, 1.78 mmol) was added; next tin (IV) chloride (0.22 mL, 1.78 mmol) was added drop-wise. The contents were stirred (3 h) and then allowed to slowly warm to room temperature (16 h). The reaction mixture was diluted with water and extracted with EtOAc (4×20 mL). The combined organic layer was washed with HCl (0.5 N, 3 mL), water, $NaHCO_3$ and brine. The organic layer was dried ($Na_2SO_4$), filtered and concentrated under reduced pressure. The crude material was purified by column chromatography on $SiO_2$ (100% Hex to 5% EtOAc in Hex) to give 54 (218 mg, 0.731 mmol, 54% yield) as a yellow oil. $^1$H-NMR (400 MHz) $CDCl_3$: 7.65-7.63 (d, 2H), 7.49-7.47 (d, 1H), 7.40-7.37 (d, 1H), 7.31-7.26 (t, 1H), 7.22-7.19 (t, 1H), 7.03-6.99 (t, 1H), 3.98 (s, 3H), 2.95-2.89 (q, 2H), 1.37-1.33 (t, 3H); $^{13}$C-NMR (100 MHz) $CDCl_3$: 189.5, 165.8, 153.6, 153.2, 151.8, 150.7, 132.1, 126.7, 124.4, 123.5, 121.1, 116.8, 115.8, 112.3, 111.0, 56.3, 21.8, 12.3. LC/MS-MS: 298.7→153.1 m/z; GS1 and GS2 at 25, DP=41, CE=29, CXP=10, $t_R$=4.77 min.

(3-Chloro-4-methoxyphenyl)(2-ethylbenzofuran-3-yl)methanone (55): In a RBF/SB, benzofuran (0.165 g, 1.13 mmol) was weighed out. The material was diluted in $CS_2$ (4.0 mL), capped and a $N_2$ balloon was attached. The contents were stirred and cooled in an ice bath (30 min). Next, 3-chloro-4-methoxybenzoyl chloride (0.280 g mL, 1.36 mmol) was added; next tin (IV) chloride (0.18 mL, 1.47 mmol) was added drop-wise. The contents were stirred (3 h) and then allowed to slowly warm to RT (16 h). The reaction mixture was diluted with water and extracted with EtOAc (4×20 mL). The combined organic layer was washed with HCl (0.5 N, 3 mL), water, $NaHCO_3$ and brine. The organic layer was dried ($Na_2SO_4$), filtered and concentrated under reduced pressure. The crude material was purified by column chromatography on $SiO_2$ (100% Hex to 5% EtOAc in Hex) to give 55 (0.140 g, 0.445 mmol, 40% yield) as a light yellow oil. $^1$H-NMR (400 MHz) $CDCl_3$: 7.92 (s, 1H), 7.78-7.75 (d, 1H), 7.50-7.48 (d, 1H), 7.41-7.39 (d, 1H), 7.31-7.27 (t, 1H), 7.23-7.19 (t, 1H), 6.70-6.98 (d, 1H), 3.99 (s, 3H), 2.94-2.88 (q, 2H), 1.37-1.33 (t, 3H); $^{13}$C-NMR (100 MHz) $CDCl_3$: 189.3, 165.9, 158.6, 153.6, 132.5, 131.5, 129.8, 126.9, 124.4, 123.5, 122.8, 121.1, 115.8, 111.2, 111.0, 56.4, 21.8, 12.3. LC/MS-MS: 315.0→169.1 m/z; GS1 and GS2 at 25, DP=56, CE=31, CXP=10, $t_R$=4.99 min.

(3-Bromo-4-methoxyphenyl)(2-ethylbenzofuran-3-yl)methanone (56): In a RBF/SB, benzofuran (0.200 g, 1.37 mmol) was weighed out. The material was diluted in $CS_2$ (4.0 mL), capped and a nitrogen balloon was attached. The contents were stirred and cooled in an ice bath (30 min). Next, 3-bromo-4-methoxybenzoyl chloride (0.444 g mL, 1.78 mmol) was added; next tin (IV) chloride (0.22 mL, 1.78 mmol) was added drop-wise. The contents were stirred (3 h) and then allowed to slowly warm to RT (16 h). The reaction mixture was diluted with water and extracted with EtOAc (4×20 mL). The combined organic layer was washed with HCl (0.5 N, 3 mL), water, $NaHCO_3$ and brine. The organic layer was dried ($Na_2SO_4$), filtered and concentrated under reduced pressure. The crude material was purified by column chromatography on $SiO_2$ (100% Hex to 5% EtOAc in Hex) to give 56 (0.195 g, 0.542 mmol, 40%) as a yellow oil. $^1$H-NMR (400 MHz) $CDCl_3$: 8.10 (s, 1H), 7.83-7.80 (d, 1H), 7.50-7.48 (d, 1H), 7.42-7.40 (d, 1H), 7.29-7.27 (t, 1H), 7.23-7.21 (t, 1H), 6.97-6.94 (d, 1H), 3.99 (s, 3H), 2.94-2.88 (q, 2H), 1.37-1.33 (t, 3H); $^{13}$C-NMR (100 MHz) $CDCl_3$: 189.2, 165.9, 159.5, 153.7, 134.7, 132.9, 130.6, 126.9, 124.4, 123.6, 121.2, 115.8, 111.8, 111.1, 111.0, 56.5, 21.9, 12.3. LC/MS-MS: 361.0→214.8 m/z; GS1 and GS2 at 25, DP=71, CE=31, CXP=14, $t_R$=5.20 min.

3-Iodo-4-methoxybenzoyl chloride (57): 3-iodo-4-methoxybenzoic acid (1.00 g, 7.19 mmol) was dissolved in $SOCl_2$ (12.0 mL) and stirred at 80° C. (22 h). Next, $SOCl_2$ was removed in vacuo and azeotroped twice with benzene to give 57 (0.700 g, 2.36 mmol, 32%) as a white solid. $^1$H-NMR (400 MHz) $CDCl_3$: 8.50 (s, 1H), 8.12-8.10 (d, 1H), 6.88-6.86 (d, 1H), 3.99 (s, 3H); $^{13}$C-NMR (100 MHz) $CDCl_3$: 165.1, 162.8, 141.9, 133.2, 126.3, 109.4, 85.2, 56.2.

(2-Ethylbenzofuran-3-yl)(3-iodo-4-methoxyphenyl)methanone (58): Benzofuran 11A (200 mg, 1.37 mmol) was weighed into a dry RBF (25 mL) containing a SB. The material was diluted in $CS_2$ (4.0 mL), capped and a $N_2$ balloon attached. The contents were stirred and cooled in an ice bath (30 min). Next, 57 (0.475 g, 1.78 mmol) was added followed by dropwise addition of tin (IV) chloride (0.22 mL). The contents were stirred (3 h) at 0° C. and slowly warmed to RT and stirred (16 h). The reaction mixture was diluted with $H_2O$ and extracted with EtOAc (4×20 mL). The combined organic layer was washed with HCl (0.5 N), $H_2O$, sat. $NaHCO_3$, and brine. The organic layer was dried ($Na_2SO_4$), filtered and concentrated in vacuo. The crude material was purified by column chromatography on $SiO_2$ (100% Hex to 5% EtOAc in Hex) to give 58 (310 mg, 0.763 mmol, 56%) as a white solid. $^1$H-NMR (400 MHz) $CDCl_3$: 8.31 (s, 1H), 7.86-7.84 (d, 1H), 7.50-7.48 (d, 1H), 7.43-7.41 (d, 1H), 7.31-7.27 (m, 1H), 7.23-7.20 (m, 1H), 6.88-6.86 (d, 1H), 3.98 (s, 3H), 2.93-2.87 (q, 2H), 1.37-1.33 (t, 3H); $^{13}$C-NMR (100 MHz) $CDCl_3$: 189.0, 165.8, 161.6, 153.6, 140.9, 133.5, 131.6, 126.9, 124.4, 123.5, 121.1, 115.8, 111.0, 110.0, 85.7, 56.6, 21.8, 12.3.

(2-Ethylbenzofuran-3-yl)(3-fluoro-4-hydroxyphenyl)methanone (59): In a RBF/SB, 54 (0.09 g, 0.302 mmol) was weighed out. The material was diluted with DMF (5.0 mL), NaSEt (0.127 g, 1.51 mmol) was added and warmed (105-110° C.; 16 h). The mixture was then quenched with 2 vol $NH_4Cl$ aq and extracted with EtOAc (4×20 mL). The organic phase was dried ($Na_2SO_4$), filtered, concentrated under reduced pressure and purified via $SiO_2$ chromatography (4:1; Hex:EtOAc) to give 59 as a brown oil (46 mg, 0.162 mmol, 54% yield). $^1$H-NMR (400 MHz) $CDCl_3$: 7.68-7.64 (d, 1H0, 7.60-7.57 (d, 1H), 7.50-7.48 (d, 1H), 7.40-7.38 (d, 1H), 7.31-7.26 (t, 1H), 7.23-7.19 (t, 1H), 7.10-7.06 (t, 1H), 6.45 (bs, 1H), 2.95-2.90 (q, 2H), 1.37-1.33 (t, 3H); $^{13}$C-NMR (100 MHz) $CDCl_3$: 189.9, 166.1, 153.6, 152.0, 149.6, 148.4, 132.1, 127.3, 126.8, 124.4, 123.6, 121.1, 117.1, 115.8, 111.0, 21.8, 12.3. LC/MS-MS: 285.0→139.0 m/z; GS1 and GS2 at 25, DP=61, CE=29, CXP=8, $t_R$=4.49 min.

(3-Chloro-4-hydroxyphenyl)(2-ethylbenzofuran-3-yl)methanone (60): In a RBF/SB, 55 (0.05 g, 0.159 mmol) was weighed out. The material was diluted with DMF (3.0 mL), NaSEt (0.066 g, 0.794 mmol) was added and warmed (105-110° C.; 16 h). The mixture was then quenched with 2 vol $NH_4Cl$ aq and extracted with EtOAc (4×20 mL). The organic phase was dried ($Na_2SO_4$), filtered, concentrated under reduced pressure and purified via $SiO_2$ chromatography (4:1; Hex:EtOAc) to give 60 (21.1 mg, 0.070 mmol, 44% yield) as brown oil. $^1$H-NMR (400 MHz) $CDCl_3$: 7.90

(s, 1H), 7.71-7.69 (d, 1H), 7.50-7.48 (d, 1H), 7.40-7.38 (d, 1H), 7.31-7.26 (t, 1H), 7.21-7.19 (t, 1H), 7.11-7.09 (d, 1H), 6.11 (bs, 1H), 2.95-2.89 (q, 2H), 1.37-1.33 (t, 3H); $^{13}$C-NMR (100 MHz) CDCl$_3$: 189.3, 166.0, 155.3, 153.7, 132.9, 130.7, 130.4, 126.8, 124.4, 123.6, 121.1, 120.3, 116.0, 115.8, 111.1, 21.8, 12.3. LC/MS-MS: 300.9→155.0 m/z; GS1 and GS2 at 25, DP=66, CE=29, CXP=8, $t_R$=4.59 min.

(3-Bromo-4-hydroxyphenyl)(2-ethylbenzofuran-3-yl) methanone (61): In a RBF/SB, 56 (0.05 g, 0.139 mmol) was weighed out. The material was diluted with DMF (2.5 mL), NaSEt (0.058 g, 0.696 mmol) was added and warmed (105-110° C.; 16 h). The mixture was then quenched with 2 vol NH$_4$Cl aq and extracted with EtOAc (4×20 mL) The organic phase was dried (Na$_2$SO$_4$), filtered, concentrated under reduced pressure and purified via SiO$_2$ chromatography (3:1; Hex:EtOAc) to give 61 (23.2 mg, 0.079 mmol, 57% yield) as a light yellow oil. $^1$H-NMR (400 MHz) CDCl$_3$: 8.06-8.05 (d, 1H), 7.76-7.74 (dd, 1H), 7.50-7.48 (d, 1H), 7.41-7.39 (d, 1H), 7.31-7.29 (t, 1H), 7.23-7.19 (t, 1H), 7.10-7.08 (d, 1H), 6.21 (bs, 1H), 2.94-2.89 (q, 2H), 1.37-1.33 (t, 3H); $^{13}$C-NMR (100 MHz) CDCl$_3$: 189.2, 166.0, 156.3, 153.7, 133.8, 133.2, 131.1, 126.8, 124.5, 123.6, 121.1, 115.9, 115.8, 111.1, 110.5, 21.8, 12.3. LC/MS-MS: 344.9→198.8 m/z; GS1 and GS2 at 25, DP=61, CE=33, CXP=12, $t_R$=4.59 min.

(2-Ethylbenzofuran-3-yl)(4-hydroxy-3-iodophenyl) methanone (62): In a RBF (35 mL) containing a SB, 58 (0.200 g, 0.492 mmol) was diluted with DMF (8.0 mL) and NaSEt (0.207 g, 2.46 mmol) was added. The reaction mixture was heated to 110° C. and stirred (16 h). The reaction was quenched by the addition of sat. NH$_4$Cl, and then extracted with EtOAc (4×20 mL). The combined organic layers were washed with brine, dried (Na$_2$SO$_4$), filtered and concentrated in vacuo. The crude material was purified by column chromatography on SiO$_2$ (Hex:EtOAc; 4:1) to give impure product and purified a $2^{nd}$ time by column chromatography on SiO$_2$ (25% EtOAc in Hex) to give 62 (40.0 mg, 0.102 mmol, 2%) as a white solid. $^1$H-NMR (400 MHz) CDCl$_3$: 8.23 (s, 1H), 7.78-7.75 (d, 1H), 7.50-7.48 (d, 1H), 7.42-7.40 (d, 1H), 7.31-7.27 (m, 1H), 7.23-7.20 (m, 1H), 7.06-7.04 (d, 1H), 6.17 (s, 1H), 2.94-2.88 (q, 2H), 1.37-1.33 (t, 3H); $^{13}$C-NMR (100 MHz) CDCl$_3$: 189.1, 166.0, 158.8, 153.6, 140.2, 133.6, 132.0, 126.8, 124.4, 123.6, 121.1, 115.7, 111.0, 85.5, 21.9, 12.3. LC/MS-MS: 393.0→246.9 m/z; GS1 and GS2 at 30, DP=86, CE=35, CXP=16, $t_R$=4.56 min.

(2-Ethylbenzofuran-3-yl)(3-methoxyphenyl)methanone (63): In a RBF/SB, benzofuran (0.200 g, 0.137 mmol) was weighed out. The material was diluted in CS$_2$ (4.0 mL), capped and a nitrogen balloon was attached. The contents were stirred and cooled in an ice bath (30 min). Next, 3-methoxybenzoyl chloride (0.25 mL, 1.78 mmol) was added; next tin (IV) chloride (0.21 mL, 1.78 mmol) was added drop-wise. The contents were stirred (3 h) and then allowed to slowly warm to RT (3 d). The reaction mixture was diluted with water and extracted with EtOAe (4×20 mL). The combined organic layer was washed with HCl (0.5 N, 3 mL), water, NaHCO$_3$ and brine. The organic layer was dried (Na$_2$SO$_4$), filtered and concentrated under reduced pressure. The crude material was purified by column chromatography on SiO$_2$ (100% Hex to 5% EtOAc in Hex) to give 63 (0.240 g, 0.865 mmol, 62%) as a yellow oil. $^1$H-NMR (400 MHz) CDCl$_3$: 7.49-7.47 (d, 1H), 7.43-7.41 (d, 1H), 7.38-7.35 (m, 3H), 7.30-7.26 (t, 1H), 7.22-7.18 (t, 1H), 7.15-7.12 (m, 1H), 3.85 (s, 3H), 2.93-2.88 (q, 2H), 1.35-1.32 (t, 3H); $^{13}$C-NMR (100 MHz) CDCl$_3$: 191.7, 166.5, 159.8, 153.7, 140.8, 129.5, 127.0, 124.4, 123.5, 121.9, 121.5, 119.2, 116.1, 113.2, 110.9, 55.5, 21.9, 12.3. LC/MS-MS: 281.0→135.1 m/z; GS1 and GS2 at 25, DP=56, CE=29, CXP=6, $t_R$=4.96 min.

(3,5-Dimethoxyphenyl)(2-ethylbenzofuran-3-yl)methanone (64) and (3,5-dimethoxyphenyl)(2-ethylbenzofuran-6-yl)methanone (65): In a RBF/SB, benzofuran (0.200 g, 0.137 mmol) was weighed out. The material was diluted in CS$_2$ (4.0 mL), capped and a nitrogen balloon was attached. The contents were stirred and cooled in an ice bath (30 min). Next, 3,5-dimethoxybenzoyl chloride (0.357 g, 1.78 mmol) was added; next tin (IV) chloride (0.21 mL, 1.78 mmol) was added drop-wise. The contents were stirred (3 h) and then allowed to slowly warm to RT and then warmed to 40° C. (24 h). The reaction mixture was diluted with water and extracted with EtOAc (4×20 mL). The combined organic layer was washed with HCl (0.5 N, 3 mL), water, NaHCO$_3$ and brine. The organic layer was dried (Na$_2$SO$_4$), filtered and concentrated under reduced pressure. The crude material was purified by column chromatography on SiO$_2$ (100% Hex to 10% EtOAc in Hex) to give 64 (3.4 mg, 0.011 mmol, 8% yield) as a yellow oil. $^1$H-NMR (400 MHz) CDCl$_3$: 7.49-7.47 (d, 2H), 7.29-7.28 (d, 1H), 7.23-7.19 (t, 1H), 6.96-6.95 (d, 2H), 6.69-6.68 (t, 1H), 3.81 (s, 6H), 2.93-2.88 (q, 2H), 1.35-1.32 (t, 3H); $^{13}$C-NMR (100 MHz) CDCl$_3$: 191.6, 166.5, 160.8, 153.7, 141.4, 126.9, 124.4, 123.5, 121.5, 116.1, 110.9, 106.7, 105.2, 55.6, 22.0, 12.3. LC/MS-MS: 311.0→173.2 m/z; GS1 and GS2 at 25, DP=56, CE=29, CXP=10, $t_R$=4.94 min; and 65 (7.9 mg, 19%, 0.025 mmol) as a clear oil. $^1$H-NMR (400 MHz) CDCl$_3$: 7.80 (s, 1H), 7.74-7.72 (d, 1H), 7.55-7.53 (d, 1H), 6.93-6.92 (d, 2H), 6.68-6.66 (t, 1H), 6.46 (s, 1H), 3.82 (s, 6H), 2.85-2.83 (q, 2H), 1.38-1.36 (t, 3H); $^{13}$C-NMR (100 MHz) CDCl$_3$: 196.1, 164.8, 160.5, 154.0, 140.4, 140.3, 133.4, 132.6, 125.0, 113.1, 107.8, 104.4, 101.5, 55.6, 22.0, 11.7. LC/MS-MS: 311.0→165.1 m/z; GS1 and GS2 at 25, DP=71, CE=27, CXP=10, $t_R$=4.96 min.

1-(5-Fluorobenzofuran-2-yl)ethanone (66): K$_2$CO$_3$ (6.17 g, 44.6 mmol) was added to a dry round bottom flask (RBF; 250 mL) containing a stir bar (SB). The contents were diluted with anhydrous acetone (100 mL) and stirred while 5-fluoro-2-hydroxybenzaldehyde (5.0 g; 35.7 mmol) was added dropwise (2-3 min). Next, chloroacetone (3.56 mL; 42.8 mmol) was added (2-3 min). A reflux condenser was attached and contents heated to reflux (19 h). The contents were cooled to ambient temperature and Büchner filtered; the solid was rinsed with acetone (2×50 mL). The filtrate was concentrated under reduced pressure and purified via SiO$_2$ chromatography (6:1; Hex:EtOAc) to afford 66 as a white solid (4.8 g; 26.9 mmol; 75% yield). $^1$H-NMR (400 MHz) CDCl$_3$: 7.53-7.50 (dd, 1H), 7.45 (s, 1H), 7.35-7.33 (d, 1H), 7.27-7.17 (t, 1H), 2.60 (s, 3H); $^{13}$C-NMR (100 MHz) CDCl$_3$: 188.5, 160.7, 158.3, 154.1, 151.9, 127.8, 116.4, 113.5, 112.6, 108.3, 26.5.

2-Ethyl-5-fluorobenzofuran (67): Ketone 66 (5.00 g; 28.1 mmol) in a RBF/SB (500 mL) was mixed with DEG (110 mL) and heated (120-130° C.). The mixture was stirred and hydrazine (6.0 mL; 55% aq solution, 119 mmol) was added dropwise (15-20 min). The mixture was heated (180-190° C.; 10 min) and then decreased to 120-130° C. Next, KOH (4.88 g, 87.0 mmol) was carefully added in portions and heated (120-130° C.; 16 h). The contents were diluted with ice water (120-130 mL) and extracted (DCM; 4×150 mL). The organic phase was dried over anhydrous MgSO$_4$, filtered, concentrated under reduced pressure, and purified via SiO$_2$ chromatography (10:1; Hex:EtOAc) to afford 67 as a clear oil (2.80 g; 15.8 mmol; 56% yield). $^1$H-NMR (400 MHz) CDCl$_3$: 7.35-7.31 (d, 1H), 7.16-7.14 (d, 1H), 6.96-

6.91 (t, 1H), 6.35 (s, 1H), 2.83-2.77 (q, 2H), 1.37-1.33 (t, 3H); $^{13}$C-NMR (100 MHz) CDCl$_3$: 162.9, 160.3, 157.9, 129.8, 111.1, 110.6, 105.7, 101.3, 21.9, 11.7.

(2-Ethyl-5-fluorobenzofuran-3-yl)(4-methoxyphenyl)methanone (68): In a RBF/SB, 67 (2.00 g, 12.2 mmol) was weighed out. The material was diluted in CS$_2$ (35.0 mL), capped and a N$_2$ balloon was attached. The contents were stirred and cooled in an ice bath (30 min). Next, 4-methoxybenzoyl chloride (2.70 g, 15.84 mmol) was added; next tin (IV) chloride (1.96 mL, 15.8 mmol) was added drop-wise. The contents were stirred (3 h) and then allowed to slowly warm to RT (16 h). The reaction mixture was diluted with water and extracted with EtOAc (4×80 mL). The combined organic layer was washed with HCl (0.5 N), water, NaHCO$_3$ and brine. The organic layer was dried (Na$_2$SO$_4$), filtered and concentrated under reduced pressure. The crude material was purified by column chromatography on SiO$_2$ (100% Hex to 5% EtOAc in Hex, and then 3:1 Hex:EtOAc) to give 68 (1.60 g, 5.36 mmol, 44% yield) as a white solid. $^1$H-NMR (400 MHz) CDCl$_3$: 7.84-7.81 (d, 2H), 7.41-7.38 (d, 1H), 7.09-7.06 (d, 1H), 7.01-6.96 (m, 3H), 3.90 (s, 3H), 2.93-2.87 (q, 2H), 1.35-1.31 (t, 3H); $^{13}$C-NMR (100 MHz) CDCl$_3$: 190.0, 167.1, 163.6, 160.7, 158.3, 149.8, 131.6, 128.2, 116.5, 113.8, 112.0, 111.7, 107.0, 55.5, 21.9, 12.2. LC/MS-MS: 299.0→135.0 m/z; GS1 and GS2 at 30, DP=11, CE=31, CXP=8, $t_R$=4.69 min.

(2-Ethyl-5-fluorobenzofuran-3-yl)(4-hydroxyphenyl)methanone (69): In a RBF/SB, 68 (1.00 g, 3.35 mmol) was weighed out. The material was diluted with DMF (60 mL), NaSEt (1.41 g, 16.8 mmol) was added and warmed (105-110° C.; 16 h). The mixture was then quenched with 2 vol NH$_4$Cl aq and extracted with EtOAc (4×80 mL). The organic phase was dried (Na$_2$SO$_4$), filtered, concentrated under reduced pressure and purified via SiO$_2$ chromatography (4:1; Hex:EtOAc) to give 69 (550 mg, 1.93 mmol, 58% yield) as a white solid. $^1$H-NMR (400 MHz) CDCl$_3$: 7.79-7.77 (d, 2H), 7.42-7.38 (dd, 1H), 7.08-7.06 (d, 1H), 7.02-6.95 (t, 1H), 6.95-6.92 (d, 2H), 6.57 (bs, 1H), 2.93-2.88 (q, 2H), 1.35-1.31 (t, 3H); $^{13}$C-NMR (100 MHz) CDCl$_3$: 190.7, 167.4, 160.6, 158.3, 149.8, 132.0, 131.4, 115.5, 112.1, 111.9, 111.6, 107.2, 107.0, 21.9, 12.2. LC/MS-MS: 285.0→121.2 m/z; GS1 and GS2 at 30, DP=4, CE=29, CXP=6, $t_R$=4.31 min.

(3,5-Dibromo-4-hydroxyphenyl)(2-ethyl-5-fluorobenzofuran-3-yl)methanone (70): In a RBF/SB, NBS (0.250 g, 1.41 mmol) diluted with DCM (12.0 mL) was mixed with DMF (0.4 mL) and the mixture cooled in an ice bath (10 min). Compound 69 (200 mg, 0.704 mmol) in DCM (1.0 mL) was added and warmed to RT (17 hr). The reaction mixture was quenched with H$_2$O and diluted with DCM (30 mL). The organic phase was washed four times with H$_2$O, NaCl aq, and then dried (Na$_2$SO$_4$), filtered, concentrated under reduced pressure, and purified twice via SiO$_2$ chromatography (Hex:EtOAc; 4:1) to give 70 (176 mg, 0.398 mmol, 57% yield) as a yellow solid. $^1$H-NMR (400 MHz) CDCl$_3$: 7.97 (s, 2H), 7.43-7.40 (dd, 1H), 7.19-7.11 (d, 1H), 7.04-7.01 (t, 1H), 6.53 (bs, 1H), 2.88-2.84 (q, 2H), 1.36-1.33 (t, 3H); $^{13}$C-NMR (100 MHz) CDCl$_3$: 187.4, 167.9, 160.9, 158.5, 153.3, 149.9, 133.3, 127.5, 115.6, 112.5, 112.3, 111.8, 110.1, 107.0, 106.8. LC/MS-MS: 442.9→278.8 m/z; GS1 and GS2 at 30, DP=21, CE=35, CXP=18, $t_R$=4.59 mM.

1-(7-Fluorobenzofuran-2-yl)ethanone (71): K$_2$CO$_3$ (1.24 g, 8.94 mmol) was added to a dry round bottom flask (RBF; 50 mL) containing a stir bar (SB). The contents were diluted with anhydrous acetone (20 mL) and stirred while 3-fluoro-2-hydroxybenzaldehyde (1.0 g, 7.13 mmol) was added dropwise (2-3 min). Next, chloroacetone (0.69 mL; 8.56 mmol) was added (2-3 min). A reflux condenser was attached and contents heated to reflux (16 h). The contents were cooled to ambient temperature and Buchner filtered; the solid was rinsed with acetone (2×15 mL). The filtrate was concentrated under reduced pressure and purified via SiO$_2$ chromatography (9:1; Hex:EtOAc) to afford 71 as a white solid (0.91 g; 5.11 mmol; 72% yield). $^1$H-NMR (400 MHz) CDCl$_3$: 7.53-7.52 (d, 1H), 7.49-7.47 (d, 11~1), 7.27-7.19 (m, 2H), 2.65 (s, 3H); $^{13}$C-NMR (100 MHz) CDCl$_3$: 188.6, 153.7, 149.6, 147.1, 143.0, 130.5, 124.4, 188.8, 113.8, 112.3, 26.6.

2-Ethyl-7-fluorobenzofuran (72): Ketone 71 (0.90 g; 5.05 mmol) in a RBF/SB (100 mL) was mixed with DEG (20 mL) and heated (120-130° C.). The mixture was stirred and hydrazine (1.08 mL; 55% aq solution, 21.2 mmol) was added dropwise (15-20 min). The mixture was heated (180-190° C.; 10 min) and then decreased to 120-130° C. Next, KOH (0.85 g, 15.2 mmol) was carefully added in portions and heated (120-130° C.; 16 h). The contents were diluted with ice water (40-50 mL) and extracted (DCM; 4×100 mL). The organic phase was dried over anhydrous MgSO$_4$, filtered, concentrated under reduced pressure, and purified via SiO$_2$ chromatography (10:1; Hex:EtOAc) to afford 72 as a clear oil (0.45 g; 2.74 mmol; 54% yield). $^1$H-NMR (400 MHz) CDCl$_3$: 7.26-7.23 (d, 1H), 7.17-7.07 (t, 1H), 6.97-6.92 (t, 1H), 6.42 (s, 1H), 2.86-2.80 (q, 2H), 1.37-1.34 (t, 3H); $^{13}$C-NMR (100 MHz) CDCl$_3$: 162.1, 149.0, 146.5, 132.6, 122.9, 115.8, 109.5, 101.5, 21.7, 11.8.

(2-Ethyl-7-fluorobenzofuran-3-yl)(4-methoxyphenyl)methanone (73): In a RBF/SB, 72 (450 mg, 2.74 mmol) was weighed out. The material was diluted in CS$_2$ (8.0 mL), capped and a N$_2$ balloon was attached. The contents were stirred and cooled in an ice bath (30 min). Next, 4-methoxybenzoyl chloride (607 mg, 3.56 mmol) was added; next tin (IV) chloride (0.44 mL, 3.56 mmol) was added drop-wise. The contents were stirred (3 h) and then allowed to slowly warm to RT (16 h). The reaction mixture was diluted with water and extracted with EtOAc (4×40 mL). The combined organic layer was washed with HCl (0.5 N), water, NaHCO$_3$ and brine. The organic layer was dried (Na$_2$SO$_4$), filtered and concentrated under reduced pressure. The crude material was purified by column chromatography on SiO$_2$ (100% Hex to 5% EtOAc in Hex, and then 3:1 Hex:EtOAc) to give 73 (275 mg, 0.922 mmol, 34% yield) as a light yellow oil. $^1$H-NMR (400 MHz) CDCl$_3$: 7.82-7.85 (d, 2H), 7.13-7.17 (d, 1H), 7.09-7.12 (m, 1H), 7.01-7.03 (d, 1H), 6.95-6.97 (d, 2H), 3.89 (s, 3H), 2.89-2.95 (q, 2H), 1.33-1.37 (t, 3H); $^{13}$C-NMR (100 MHz) CDCl$_3$: 189.9, 166.0, 163.7, 148.9, 146.4, 140.7, 132.3, 131.5, 130.7, 124.0, 116.8, 113.6, 110.5, 55.5, 21.7, 12.3. LC/MS-MS: 299.0→135.0 m/z; GS1 and GS2 at 30, DP=6, CE=31, CXP=8, $t_R$=4.74 min.

(2-Ethyl-7-(ethylthio)benzofuran-3-yl)(4-hydroxyphenyl)methanone (74): In a RBF/SB, 73 (200 mg, 0.67 mmol) was weighed out. The material was diluted with DMF (12 mL), NaSEt (282 mg, 3.35 mmol) was added and warmed (105-110° C.; 16 h). The mixture was then quenched with 2 vol NH$_4$Cl aq and extracted with EtOAc (4×20 mL). The organic phase was dried (Na$_2$SO$_4$), filtered, concentrated under reduced pressure and purified via SiO$_2$ chromatography (4:1; Hex:EtOAc) to give 74 (50.0 mg, 0.150 mmol, 23% yield) as a yellow oil. $^1$H-NMR (400 MHz) CDCl$_3$: 7.78-7.80 (d, 2H), 7.26-7.28 (d, 2H), 7.12-7.15 (t, 1H), 6.91-6.93 (d, 2H), 6.58 (bs, 1H), 3.06-3.12 (q, 21-1), 2.90-2.96 (q, 2H), 1.32-1.37 (m, 6H); $^{13}$C-NMR (100 MHz) CDCb: 191.3, 165.7, 161.0, 152.5, 132.2, 131.2, 127.3, 125.9, 124.0, 119.6, 119.0, 116.5, 115.5, 27.3, 21.8, 14.7, 12.5. LC/MS-MS: 327.0→121.0 m/z; GS1 and GS2 at 30, DP=26, CE=31, CXP=6, $t_R$=4.55 min.

(1,2-Dimethyl-1H-indol-3-yl)(4-methoxyphenyl)methanone (75): In a RBF/SB, 1,2-dimethyl-1H-indole (0.400 g, 2.75 mmol) was weighed out. The material was diluted in $CS_2$ (8.0 mL), capped and a nitrogen balloon was attached. The contents were stirred and cooled in an ice bath (30 min). Next, 4-methoxybenzoyl chloride (0.53 mL, 3.58 mmol) was added; next tin (IV) chloride (0.42 mL, 3.54 mmol) was added drop-wise. The contents were stirred (3 h) and then allowed to slowly warm to RT (16 h). The reaction mixture was diluted with water and extracted with EtOAc (4×30 mL). The combined organic layer was washed with HCl (0.5 N), water, $NaHCO_3$ and brine. The organic layer was dried ($Na_2SO_4$), filtered and concentrated under reduced pressure. The crude material was purified by column chromatography on $SiO_2$ (100% Hex to 5% EtOAc in Hex) to give 75 (215 mg, 0.770 mmol, 28% yield) as a light brown solid. $^1$H-NMR (400 MHz) $CDCl_3$: 7.78-7.80 (d, 2H), 7.38-7.36 (d, 1H), 7.33-7.31 (d, 1H), 7.23-7.19 (t, 1H), 7.10-7.06 (t, 1H), 6.95-6.93 (d, 2H), 3.89 (s, 3H), 3.74 (s, 3H), 2.60 (s, 3H); $^{13}$C-NMR (100 MHz) $CDCl_3$: 191.7, 162.5, 143.8, 136.5, 133.8, 131.6, 127.1, 121.8, 121.1, 120.9, 113.8, 113.4, 109.1, 55.4, 29.6, 12.4. LC/MS-MS: 280.0→135.0 m/z; GS1 and GS2 at 30, DP=21, CE=29, CXP=8, $t_R$=4.25 min.

(1,2-Dimethyl-1H-indol-3-yl)(4-hydroxyphenyl)methanone (76): In a RBF/SB, 72 (50.0 mg, 0.179 mmol) was weighed out. The material was diluted with DMF (4.0 mL), NaSEt (75 mg, 0.895 mmol) was added and warmed (105-110° C.; 16 h). The mixture was then quenched with 2 vol $NH_4Cl$ aq and extracted with EtOAc (4×20 mL). The organic phase was dried ($Na_2SO_4$), filtered, concentrated under reduced pressure and purified via $SiO_2$ chromatography (4:1; Hex:EtOAc) to give 76 (40 mg, 1.50 mmol, 84% yield) as a white solid. $^1$H-NMR (400 MHz) $CDCl_3$: 7.75-7.73 (d, 2H), 7.37-7.32 (t, 2H), 7.23-7.19 (t, 1H), 7.10-7.06 (t, 1H), 6.89-6.87 (d, 2H), 5.57 (bs, 1H), 3.75 (s, 3H), 2.61 (s, 3H); $^{13}$C-NMR (100 MHz) $CDCl_3$: 191.8, 158.9, 144.0, 136.5, 133.9, 131.9, 127.1, 121.9, 121.2, 120.9, 115.0, 113.7, 109.1, 29.7, 12.4. LC/MS-MS: 266.0→121.1 m/z; GS1 and GS2 at 30, DP=21, CE=31, CXP=6, $t_R$=3.96 min.

(3,5-Dibromo-4-hydroxyphenyl)(1,2-dimethyl-1H-indol-3-yl)methanone (77): In a RBF/SB, NBS (26.0 mg, 0.150 mmol) in DCM (1.0 mL) was diluted with DMF (0.02 mL) and cooled in an ice bath (10 min). Compound 76 (20M mg, 0.075 mmol) dissolved in DCM (1.0 mL) was added and the reaction mixture was warmed up to RT (17 h). The mixture was quenched with $H_2O$ (1 vol) and diluted with DCM (10 ml). The organic phase was washed four times with $H_2O$, and then NaCl aq. The organic phase was dried ($Na_2SO_4$), filtered, concentrated under reduced pressure and purified via $SiO_2$ chromatography (Hex:EtOAc; 4:1) to give 77 (17.0 mg, 0.040 mmol 54% yield) as a white solid. $^1$H-NMR (400 MHz) DMSO-$d_6$: 10.7 (bs, 1H), 7.78 (s, 2H), 7.53-7.55 (d, 1H), 7.31-7.32 (d, 1H), 7.18-7.22 (t, 1H), 7.07-7.11 (t, 1H), 3.77 (s, 3H), 2.50 (s, 3H); $^{13}$C-NMR (100 MHz) DMSO-$d_6$: 187.9, 154.2, 145.6, 136.8, 135.2, 133.4, 126.8, 122.4, 121.8, 120.1, 112.2, 111.8, 110.7, 30.3, 12.9. LC/MS-MS: 423.9→278.8 m/z; GS1 and GS2 at 30, DP=21, CE=37, CXP=18, $t_R$=4.26 min.

3,5-Dichloro-4-hydroxybenzoyl chloride (78): 3,5-dichloro-4-hydroxybenzoic acid (800 mg, 3.86 mmol) was dissolved in $SOCl_2$ (10.0 mL) and the reaction mixture stirred at RT (16 h) and then heated to reflux (5 h). Next, $SOCl_2$ was removed in vacuo and azeotroped twice with toluene to give a mixture of product and starting material. The crude compound was dissolved in $SOCl_2$ (8.0 mL) and refluxed (16 h). The $SOCl_2$ was removed in vacuo and azeotroped twice with toluene to give 78 (0.540 g, 2.40 mmol, 62%) as a brown solid. $^1$H-NMR (400 MHz) $CDCl_3$: 8.07 (s, 2H), 6.59 (bs, 1H); $^{13}$C-NMR (100 MHz) $CDCl_3$: 165.5, 153.7, 131.5 126.4, 121.8.

(3,5-Dichloro-4-hydroxyphenyl)(2-ethylbenzofuran-3-yl)methanone (79): Benzofuran 11A (200 mg, 1.37 mmol) was weighed out into a dry RBF (25 mL) containing a SB. The material was diluted in $CS_2$ (4.0 mL), capped and a $N_2$ balloon attached. The contents were stirred and cooled in an ice bath (30 min). Next, 78 (0.401 g, 1.78 mmol) was added followed by dropwise addition of tin (IV) chloride (0.22 mL). The contents were stirred (3 h) at 0° C. and slowly warmed to RT and stirred (16 h). The reaction mixture was diluted with $H_2O$ and extracted with EtOAc (4×20 mL). The combined organic layer was washed with HCl (0.5 N), $H_2O$, sat. $NaHCO_3$, and brine. The organic layer was dried ($Na_2SO_4$), filtered and concentrated in vacuo. The crude material was purified three times by column chromatography on $SiO_2$ (100% Hexanes to 5% EtOAc in Hexanes) to give 79 (30.0 mg, 0.089 mmol, 7%) as an off-white solid. $^1$H-NMR (400 MHz) $CDCl_3$: 8.31 (s, 1H), 7.88 (s, 2H), 7.53-7.51 (d, 1H), 7.42-7.40 (d, 1H), 7.35-7.31 (m, 1H), 2.98-2.92 (q, 2H), 1.40-1.36 (t, 3H). LC/MS-MS: 339.1→146.2 m/z; GS1 and GS2 at 30, DP=71, CE=35, CXP=8, $t_R$=4.64 min.

4-Methoxy-3,5-dimethylbenzoyl chloride (80): 3,5-dimethyl-4-methoxy-benzoic acid (0.500 g, 2.77 mmol) was dissolved in $SOCl_2$ (10.0 mL) and the stirred at RT (16 h) and then heated to reflux (15 h). Next, $SOCl_2$ was removed in vacuo and azeotroped twice with benzene to give 80 (0.530 g, 2.67 mmol, 96%) as a white solid. $^1$H-NMR (400 MHz) $CDCl_3$: 7.80 (s, 2H), 3.79 (s, 3H), 2.34 (s, 6H).

(2-Ethylbenzofuran-3-yl)(4-methoxy-3,5-dimethylphenyl)methanone (81): Benzofuran 11A (300 mg, 2.05 mmol) was weighed into a dry RBF (25 mL) containing a SB. The material was diluted in $CS_2$ (6.0 mL), capped and a $N_2$ balloon attached. The contents were stirred and cooled in an ice bath (30 min). Next, 80 (0.530 g, 2.67 mmol) was slowly added followed by dropwise addition of tin (IV) chloride (0.33 mL). The contents were stirred (3 h) at 0° C. and then slowly warmed to RT and stirred (16 h). The reaction mixture was diluted with $H_2O$ and extracted with EtOAc (4×20 mL). The combined organic layer was washed with HCl (0.5 N), $H_2O$, sat. $NaHCO_3$, and brine. The organic layer was dried ($Na_2SO_4$), filtered and concentrated in vacuo. The crude material was purified by column chromatography on $SiO_2$ (100% hexanes to 5% EtOAc in hexanes) to give 81 (248 mg, 0.804 mmol, 39%) as a clear oil. $^1$H-NMR (400 MHz) $CDCl_3$: 7.53 (s, 2H), 7.49-7.45 (t, 2H), 7.30-7.26 (m, 1H), 7.22-7.19 (t, 1H), 3.80 (s, 3H), 2.91-2.85 (q, 2H), 2.32 (s, 6H), 1.35-1.31 (t, 3H); $^{13}$C-NMR (100 MHz) $CDCl_3$: 191.3, 165.6, 161.0, 153.6, 134.8, 131.1, 130.2, 127.2, 124.2, 123.4, 121.3, 116.2, 110.9, 59.7, 21.8, 16.1, 12.3.

(2-Ethylbenzofuran-3-yl)(4-hydroxy-3,5-dimethylphenyl)methanone (82): In a RBF (35 mL) containing a SB, 81 (200 mg, 0.649 mmol) was diluted with DMF (10.0 mL) and NaSEt (0.218 g, 2.59 mmol) was added. The reaction mixture was heated to 110° C. and stirred (16 h). The reaction was quenched by the addition of sat. $NH_4Cl$, and extracted with EtOAc. The combined organic layers were washed with brine, dried ($Na_2SO_4$), filtered and concentrated in vacuo. The crude material was purified by column chromatography on $SiO_2$ (hexanes:EtOAc; 4:1) to give 82 (30.0 mg, 0.102 mmol, 16%) as a light yellow oil. $^1$H-NMR (400 MHz) CDCl$_3$: 7.55 (s, 2H), 7.49-7.46 (m, 2H), 7.30-7.26 (m, 1H), 7.22-7.18 (t, 1H), 5.77 (s, 1H), 2.91-2.86 (q, 2H), 2.26 (s, 6H), 1.35-1.32 (t, 3H); $^{13}$C-NMR (100 MHz) CDCl$_3$: 191.2, 165.1, 157.0, 153.6, 131.2, 130.6, 127.3, 124.2, 123.3, 123.2, 121.3, 116.3, 110.9, 21.8, 15.9, 12.5. LC/MS-MS: 294.8→173.2 m/z; GS1 and GS2 at 30, DP=16, CE=29, CXP=18, t$_R$=4.49 min.

3,5-Di-tert-butyl-4-hydroxybenzoyl chloride (83): 3,5-di-tert-butyl-4-hydroxybenzoic acid (0.500 g, 2.00 mmol) was dissolved in SOCl$_2$ (7.0 mL) and heated to reflux (18 h). Next, the contents were stirred at RT (16 h) and then heated to 80° C. for (4 h). The SOCl$_2$ was then removed in vacuo and azeotroped twice with toluene to give 83 (500 mg, 1.86 mmol, 93%) as a white solid. $^1$H-NMR (400 MHz) CDCl$_3$: 7.99 (s, 2H), 5.97 (s, 1H), 1.47 (s, 18H).

(3,5-Di-tert-butyl-4-hydroxyphenyl)(2-ethylbenzofuran-3-yl)methanone (84): Benzofuran 11A (200 mg, 1.37 mmol) was weighed out into a dry RBF (25 mL) containing a SB. The material was diluted in CS$_2$ (4.0 mL), capped and a N$_2$ balloon attached. The contents were stirred and cooled in an ice bath (30 min). Next, 83 (0.478 g, 1.78 mmol) was added followed by the dropwise addition of tin (IV) chloride (0.22 mL). The contents were stirred (3 h) at 0° C. and slowly warmed to RT and stirred (16 h). The reaction mixture was diluted with H$_2$O and extracted with EtOAc (4×20 mL). The combined organic layer was washed with HCl (0.5 N), H$_2$O, sat. NaHCO$_3$, and brine. The organic layer was dried (Na$_2$SO$_4$), filtered and concentrated in vacuo. The crude material was purified by column chromatography on SiO$_2$ (90% Hex and 10% EtOAc) to give 84 (250 mg, 0.660 mmol, 48%) as a yellow oil. $^1$H-NMR (400 MHz) CDCl$_3$: 7.77 (s, 2H), 7.49-7.43 (dd, 2H), 7.29-7.26 (m, 1H), 7.21-7.17 (t, 1H), 5.74 (s, 1H), 2.96-2.91 (q, 2H), 1.43 (s, 18H), 1.37-1.33 (t, 3H); $^{13}$C-NMR (100 MHz) CDCl$_3$: 191.1, 165.4, 158.4, 153.6, 135.7, 130.4, 127.4, 127.2, 124.1, 123.1, 121.5, 116.3, 110.9, 34.4, 30.2, 21.8, 12.4. LC/MS-MS: 379.2→1731 m/z; GS1 and GS2 at 30, DP=46, CE=39, CXP=10, t$_R$=5.65 min.

(3,5-Dibromo-4-methoxyphenyl)(2-ethylbenzofuran-3-yl)methanone (85): In a RBF (25 mL) containing a SB, 7 (0.100 g, 0.236 mmol) was diluted with THF (2.0 mL) and potassium carbonate (37.0 mg, 0.259 mmol) was added. The reaction mixture was stirred (10 min) and iodo-methane (16.0 µL, 0.259 mmol) was added and stirred at 40° C. (16 h). The reaction was diluted with H$_2$O and extracted with EtOAc (3×10 mL) The combined organic layers were washed with brine, dried (Na$_2$SO$_4$), filtered and concentrated in vacuo. The crude material was purified by column chromatography on SiO$_2$ (Hex:EtOAc; 6:1) to give 85 (22.0 mg, 0.050 mmol, 22%). $^1$H-NMR (400 MHz) CDCl$_3$: 7.99 (s, 2H), 7.51-7.49 (d, 1H), 7.43-7.41 (d, 1H), 7.33-7.30 (t, 1H), 7.26-7.25 (m, 1H), 3.98 (s, 3H), 2.93-2.88 (q, 2H), 1.38-1.34 (t, 3H); $^{13}$C-NMR (100 MHz) CDCl$_3$: 188.0, 166.9, 157.7, 153.7, 137.2, 133.6, 126.4, 124.7, 123.9, 121.0, 118.5, 115.3, 111.1, 60.8, 22.0, 12.2. LC/MS-MS: 439.0→292.7 m/z; GS1 and GS2 at 30, DP=91, CE=35, CXP=18, t$_R$=5.68 min.

(2-Butylbenzofuran-3-yl)(4-methoxyphenyl)methanone (86): 2-butylbenzofuran (400 mg, 0.405 mL, 2.30 mmol) was weighed out into a dry RBF (25 mL) containing a SB. The material was diluted in CS$_2$ (6.0 mL) and a N$_2$ balloon attached. The mixture was stirred and cooled in an ice bath (30 min). Next, 4-methoxybenzoyl chloride (0.404 mL, 2.98 mmol) was added followed by dropwise addition of tin (IV) chloride (0.370 mL, 2.98 mmol). The contents were stirred (3 h) at 0° C. and slowly warmed to RT and stirred (3 d). The reaction mixture was diluted with H$_2$O and extracted with EtOAc (4×12 mL). The combined organic layer was washed with HCl (0.5 N), H$_2$O, sat. NaHCO$_3$, and brine. The organic layer was dried (Na$_2$SO$_4$), filtered and concentrated in vacuo. The crude material was purified by column chromatography on SiO$_2$ (100% hexanes to 5% ethyl acetate in hexanes) to give 86 (0.455 g, 1.48 mmol, 64%) as a clear oil. $^1$H-NMR (400 MHz) CDCl$_3$: 7.87-7.85 (d, 2H), 7.49-7.47 (d, 1H), 7.38-7.36 (d, 1H), 7.28-7.25 (m, 1H), 7.20-7.16 (m, 1H), 6.97-6.95 (d, 2H), 3.88 (s, 3H), 2.95-2.91 (t, 2H) 1.79-1.75 (m, 2H), 1.40-1.34 (m, 2H), 0.92-0.88 (t, 3H); $^{13}$C-NMR (100 MHz) CDCl$_3$: 190.5, 164.6, 163.4, 153.6, 131.9, 131.7, 127.2, 124.1, 123.3, 121.2, 116.8, 113.7, 111.9, 55.5, 30.2, 27.8, 22.4, 13.7.

(2-Butylbenzofuran-3-yl)(4-hydroxyphenyl)methanone (87): In a RBF (100 mL) containing a SB, 86 (400 mg, 1.30 mmol) was diluted with DMF (18.0 mL) and NaSEt (0.426 g, 5.19 mmol) was added. The reaction mixture was heated to 110° C. and stirred (16 h). The reaction was quenched by the addition of sat. NH$_4$Cl, and was extracted with EtOAc (4×25 mL). The combined organic layers were washed with brine, dried (Na$_2$SO$_4$), filtered and concentrated in vacuo. The crude material was purified by column chromatography on SiO$_2$ (Hex:EtOAc; 4:1) to afford 87 (0.210 mg, 0.713 mmol, 55%) as a light yellow oil. $^1$H-NMR (400 MHz) CDCl$_3$: 7.81-7.78 (d, 2 II), 7.48-7.46 (d, 1H), 7.37-7.36 (d, 1H), 7.29-7.25 (m, 1H), 7.20-7.16 (m, 1H), 6.94-6.90 (d, 2H), 6.56 (bs, 1H), 2.93-2.89 (t, 2H) 1.79-1.71 (m, 2H), 1.38-1.32 (m, 2H), 0.90-0.86 (t, 3H); $^{13}$C-NMR (100 MHz) CDCl$_3$: 191.2, 165.0, 160.4, 153.6, 132.1, 131.6, 127.1, 124.2, 123.4, 121.2, 116.7, 115.4, 111.0, 30.1, 27.9, 22.3, 13.7. LC/MS-MS: 295.0→121.2 m/z; GS1 and GS2 at 30, DP=56, CE=31, CXP=6, t$_R$=4.51 min.

(2-Butylbenzofuran-3-yl)(3,5-dibromo-4-hydroxyphenyl)methanone (88): In a RBF (15 mL) containing a SB, NBS (48.0 mg, 0.272 mmol) in DCM (2.0 mL) was treated with DMF (40 µL) at −10° C. (ice-brine cooling bath) for 10 min. Then a solution of 87 (0.040 g, 0.136 mmol) in DCM (2.0 mL) was added. The reaction mixture slowly warmed to RT and stirred (17 h). To reaction was quenched with H$_2$O and the organic layer washed with water (4×0.5 mL) and brine. The organic layer was dried (Na$_2$SO$_4$), filtered and concentrated under reduced pressure. The crude material was purified twice by column chromatography on SiO$_2$ (hexanes:EtOAc; 4:1) to afford 88 (27.0 mg, 0.060 mmol, 44%) as a light yellow oil. $^1$H-NMR (400 MHz) CDCl$_3$: 7.98 (s, 2H), 7.50-7.48 (d, 1H), 7.40-7.38 (d, 1H), 7.32-7.29 (m, 1H), 7.26-7.21 (m, 1H), 6.36 (bs, 1H), 2.91-2.87 (t, 2H) 1.82-1.74 (m, 2H), 1.42-1.33 (m, 2H), 0.94-0.88 (t, 3H); $^{13}$C-NMR (100 MH z) CDCl$_3$: 187.0, 165.0, 152.9, 152.3, 132.9, 132.7, 125.8, 123.8, 123.0, 120.2, 115.1, 110.4, 109.2, 29.3, 27.3, 21.7, 12.9. LC/MS-MS: 452.9→278.9 m/z; GS1 and GS2 at 30, DP=101, CE=37, CXP=16, t$_R$=7.82 min.

(2-Ethylbenzofuran-3-yl)(2,3,4,5,6-pentadeuteriophenyl)methanone (89): Benzofuran 11A (0.386 g, 2.64 mmol) was weighed out into a dry RBF (25 mL) containing a SB. The material was diluted in CS$_2$ (8.0 mL), capped and a N$_2$ balloon was attached. The contents were stirred and cooled in an ice bath (30 min). Next benzoyl chloride-d$_5$ (0.399 mL, 3.43 mmol) was added slowly; next tin (IV) chloride (0.40 mL) was added drop-wise. The contents were stirred (3.0 h) at 0° C. and then allowed to slowly warm to RT and stirred (3 d). The reaction mixture was diluted with water and extracted with ethyl acetate (4×20 mL). The combined organic layer was washed with HCl (0.5 N, 3.0 mL), water, sat. NaHCO$_3$, and brine. The organic layer was dried (Na$_2$SO$_4$), filtered and concentrated in vacuo. The compound was purified twice by column chromatography on SiO$_2$ (Hex:EtOAc; 4:1) to give 89 (270 mg, 1.06 mmol, 40%) as a yellow oil which solidified upon sitting. $^1$H-NMR (400 MHz) CDCl$_3$: 7.50-7.48 (d, 1H), 7.39-7.37 (d, 1H), 7.29-7.26 (m, 1H), 7.21-7.17 (m, 1H), 2.94-2.88 (q, 2H), 1.36-1.32 (t, 3H); $^{13}$C-NMR (100 MHz) CDCl$_3$: 192.0, 166.5, 153.7, 139.3, 132.2 (t, CD), 128.7 (t, 2CD), 128.0 (t, 2CD), 127.0, 124.4, 123.5, 121.4, 116.1, 111.0, 21.9, 12.3. LC/MS-MS: 256.2→109.9 m/z; GS1 and GS2 at 30, DP=36, CE=27, CXP=6, t$_R$=4.78 min.

Part One: Compound Synthesis

Figure 4:
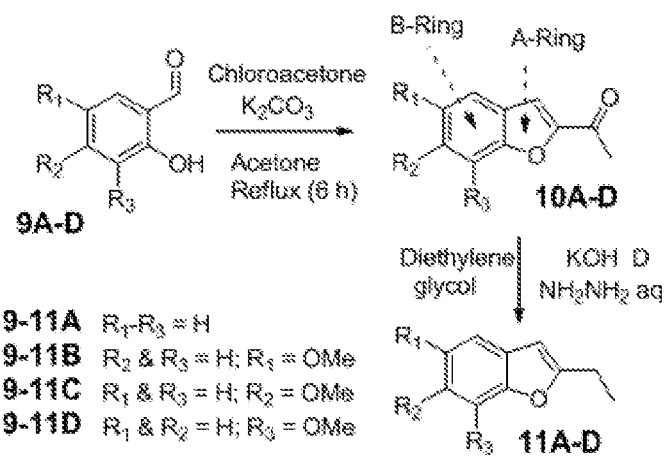
FIG. 4 is a schematic diagram showing synthesis of 2-ethylbenzofurans.

Summarized in FIG. 4, chemical synthesis utilized 2-hydroxy-benzaldehydes 9A-9D. Benzaldehydes were coupled with ehloroacetone under basic conditions to afford 2-(2-oxopropoxy)benzaldehydes with subsequent base catalyzed intramolecular aldol condensation to give the corresponding 1-(benzofuran-2-yl)ethanone, 10A-D.

Figure 5:
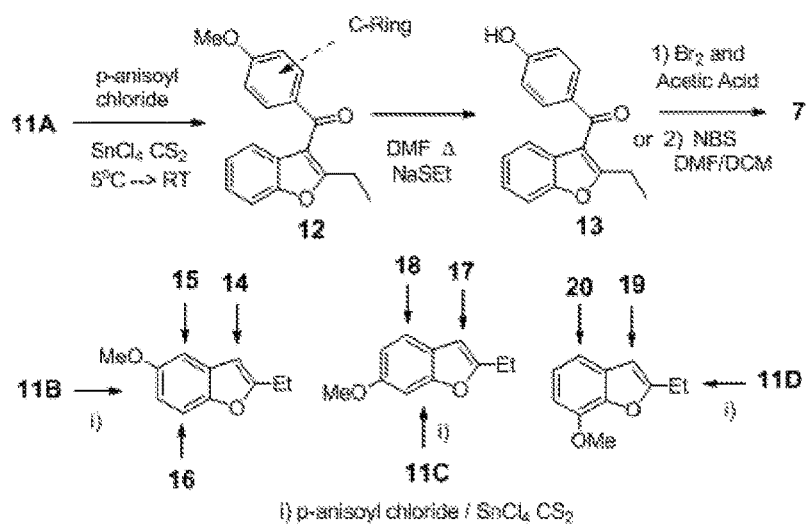
FIG. 5 is a schematic diagram showing synthesis of benzbromarone methoxy-(2-ethylbenzofuran-(yl) (4-methoxyphenyl)methanones.

The bicyclic structure thus formed is referred to as A-Ring and B-Ring, respectively (FIG. 4). The ketones were reduced to afford 2-ethylbenzofurans 11A-D. Compound 11A was reacted with p-anisoyl chloride (4-methoxybenzoyl chloride) under acid conditions to produce (2-ethylbenzofuran-3-yl)(4-methoxyphenyl)methanone 12 (FIG. 5). Herein, we refer to the additional ring thus added as the C-Ring. The para-methoxy group on the C-ring was de-methylated under basic conditions (NaSEt/DMF) to afford phenol 13, and then dibrominated to give benzbromarone 7.

Figure 6:
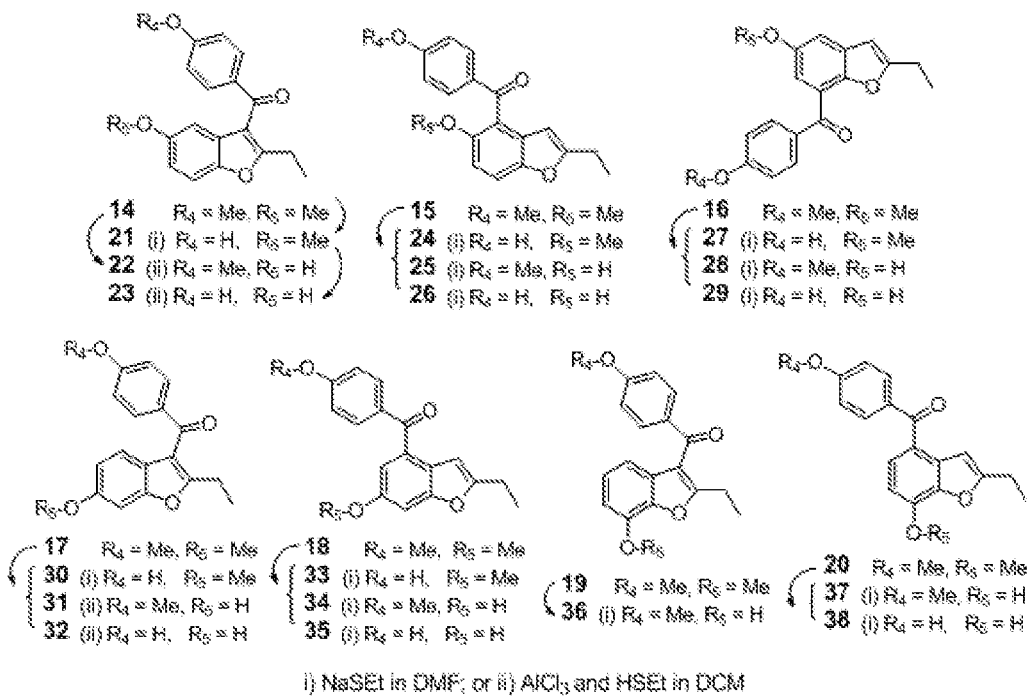
FIG. 6 shows formation of mono- and diphenolic compounds (21-38).

Analogous reactions, but with electronically donating methoxy groups on the B-Ring (i.e. 11B-11D; FIG. 5), produced regioisomers. The 5-methoxy analog 11B gave three products 14-16 (the –3, –4, and –7 substituted analogs, respectively), while 6-methoxy 11C gave two products 17 and 18 (the –3 and –4 substituted analogs, respectively), and 7-methoxy 11D generated two products, 19 and 20 (the –3 and –4 substituted analogs, respectively). Compounds 14-20 were converted to their corresponding mono- or di-phenolic analogs (21-38; FIG. 6) using either i) basic via NaSEt in DMF; or via ii) acidic using AlCl$_3$ and HSEt in DCM.

Figure 7:
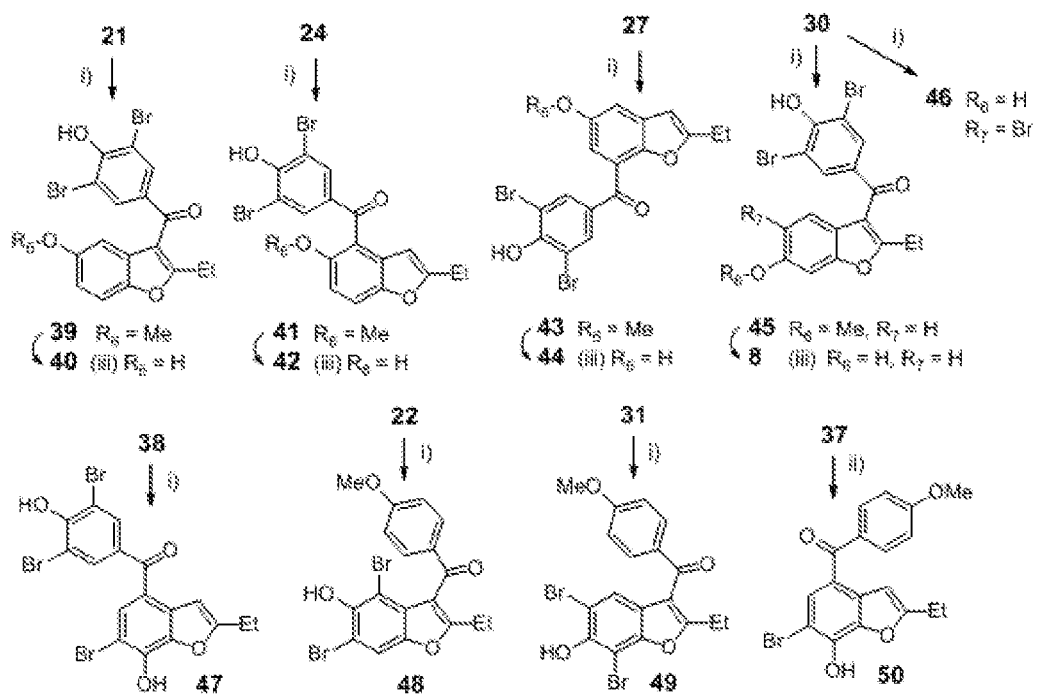
FIG. 7 shows formation of mono-, di-, and tri-brominated compounds (39-50).

Summarized in FIG. 7, analogs of 7 with C-Ring dibromo-phenolic compounds and subsequent deprotection (AlCl$_3$/HSEt) of the second methoxy group to the corresponding diphenolic compounds were prepared. For the 5-methoxy series, compound 21 was halogenated to 39 and converted to diphenol 40. Two other 5-methoxy isomers, (2-ethyl-5-methoxybenzofuran-4-yl)(4-hydroxyphenyl) methanone 24 and (2-ethyl-5-methoxybenzofuran-7-yl)(4-hydroxyphenyl)methanone 27 were converted to di-bromo and diphenolic analogs, 41 to 42 and 43 to 44, respectively.

Compound 30 was dibrominated to 45, and deprotected to afford 8, an authentic sample of 7's major metabolite. Using three mol equivalents of NBS, compound 30 gave compound 46. Another tribrominated compound was 47. Examples of B-Ring brominated analogs include halogenation of 5-hydroxy 22 and 6-hydroxy 31 to give 48 and 49, respectively; whereas 7-hydroxy analog 37 produced mono-brominated 50.

Figure 8:
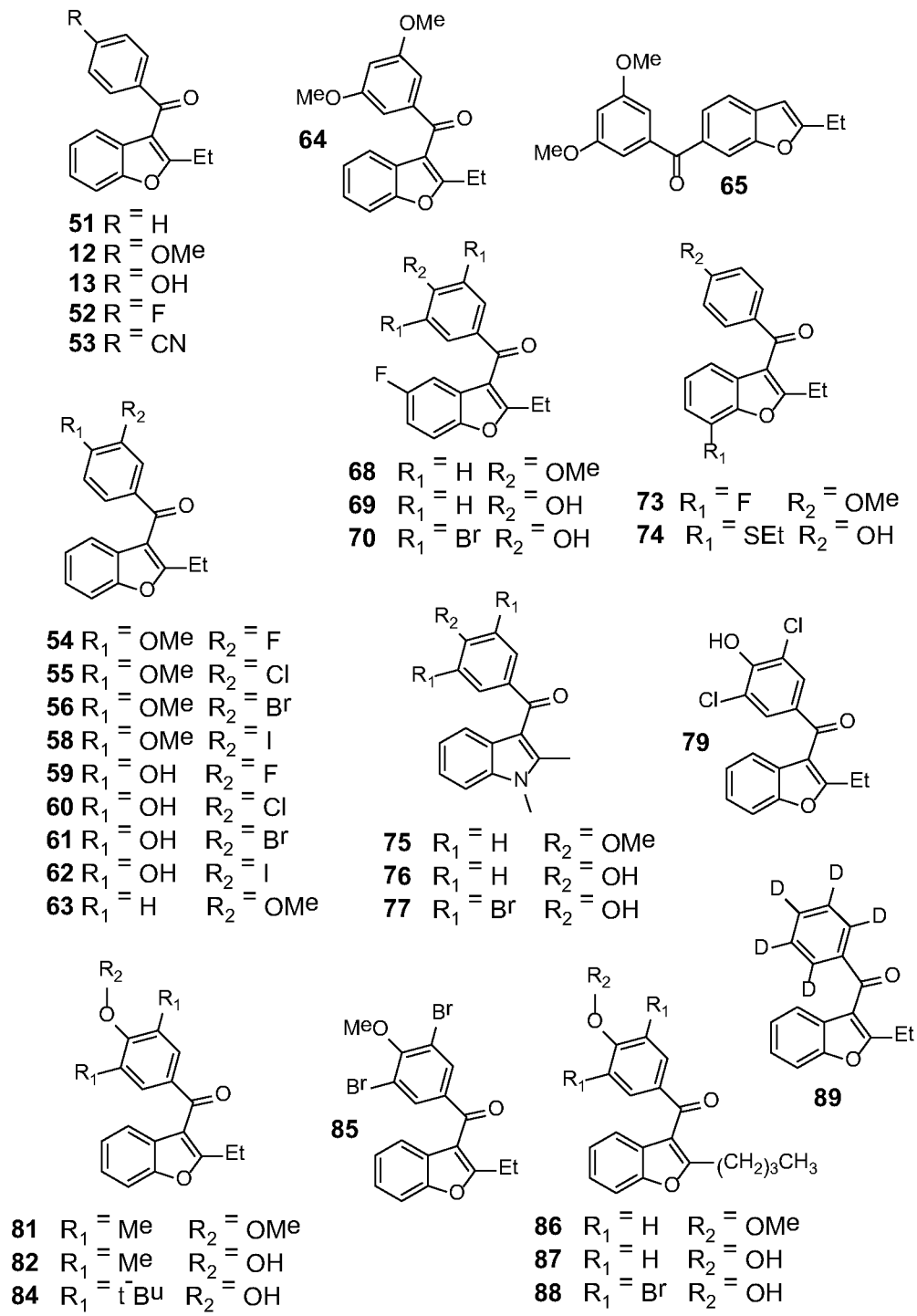
FIG. 8 shows additional compounds to probe SAR.
Figure 9:
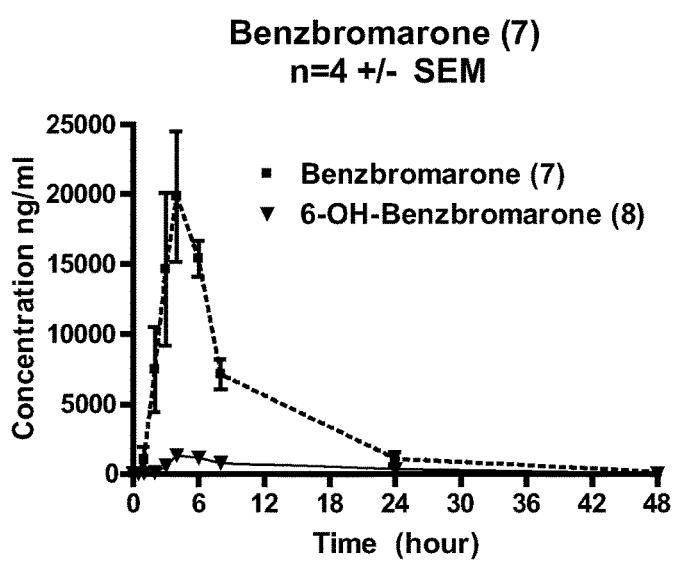
FIG. 9 shows benzbromarone 7 and metabolite 8 rat blood concentration data via oral capsule of 7 dosed at 16.4±1.7 mg/kg; rats=254±12 g.
Figure 10:
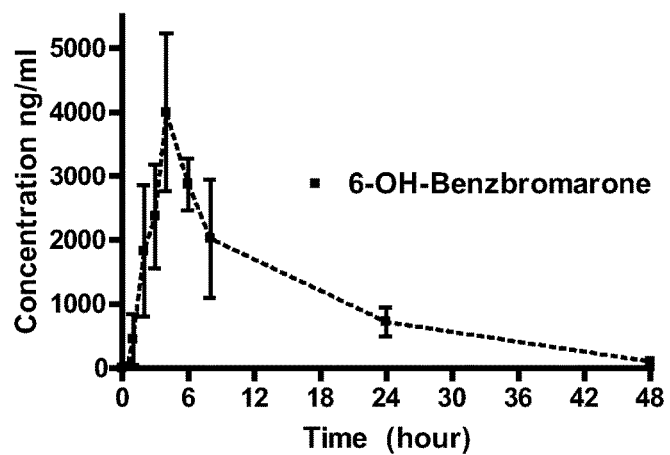
FIG. 10 shows 6-hydroxy-benzbromarone 8 rat blood concentration data from an oral capsule of 8 dosed at 16.3±1.2 mg/kg; rats=255±13 g.
Figure 11:
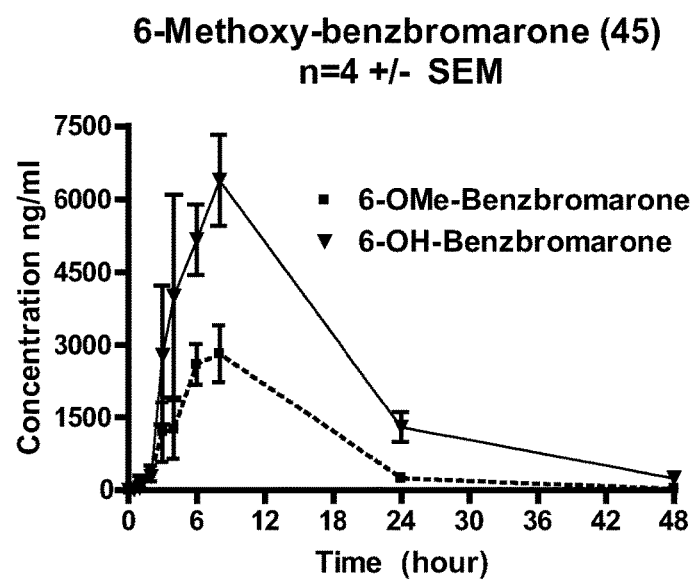
FIG. 11 shows 6-methoxy-benzbromarone 45 and metabolite 8 rat blood concentration data from an oral capsule of 45 dosed at 16.9±0.9 mg/kg; rats=250±7 g.
Figure 12:
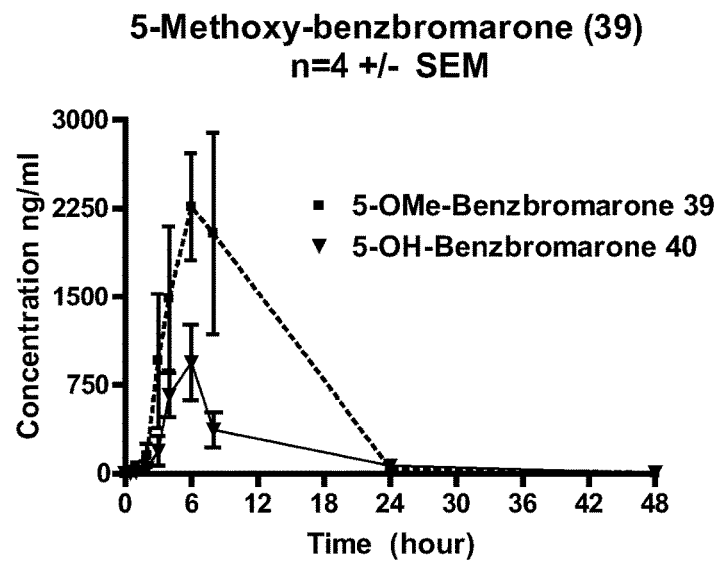
FIG. 12 shows 5-methoxy-benzbromarone 39 and metabolite 40 rat blood concentration data from an oral capsule dose of 39 dosed at 16.5±0.8 mg/kg; rats=260±10 g.
Figure 13:
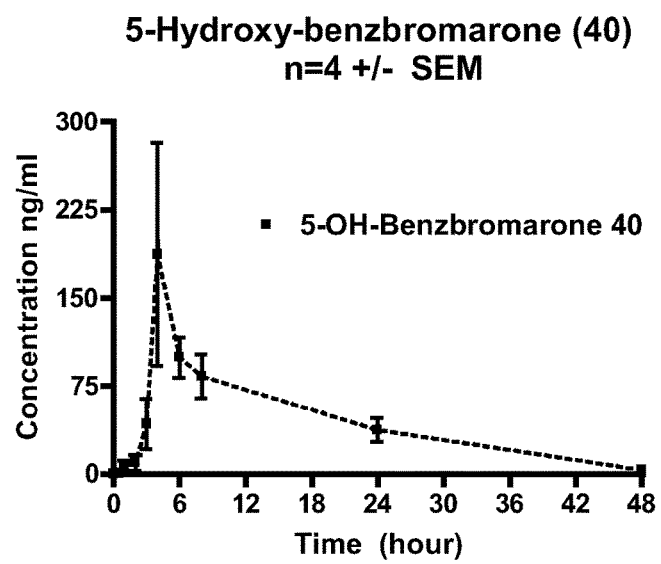
FIG. 13 shows 5-hydroxy-benzbromarone 40 rat blood concentration data from an oral capsule dose of 40 dosed at 15.2±0.4 mg/kg; rats=257±9 g.
Figure 14:
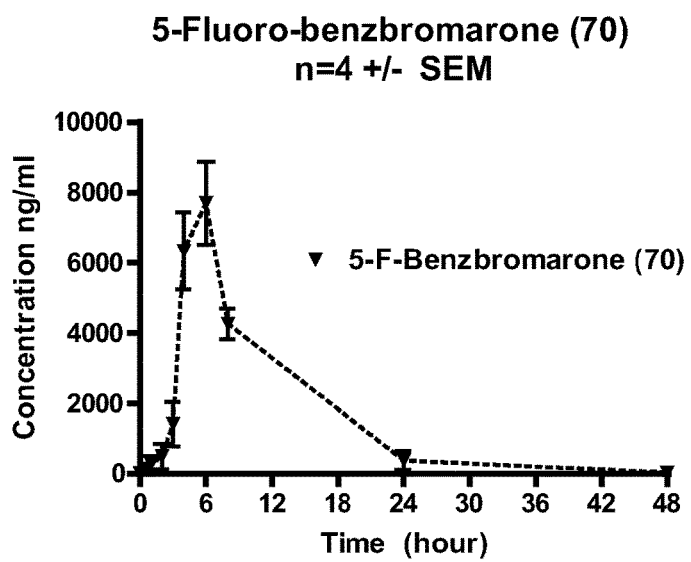
FIG. 14 shows 5-fluoro-benzbromarone 70 rat blood concentration data from an oral capsule dose of 70 dosed at 17.2±0.5 mg/kg; rats=252±9 g.

As summarized in FIG. 8, additional compounds were prepared to further illustrate the importance of various structural requirements in order to be a potent urate transporter inhibitor. Previously, compound 12 and 13 were prepared and used to produce benzbromarone 7. Compound 13 illustrates the importance of the phenol and suggests the notion that hydrogen bonding interactions may be important. Therefore, we prepared analog 51 without OH in the para position, and also para fluoro 52 and para-cyano 53. The importance of inductive effects and mono-versus di-halo analogs were probed by preparing the mono-fluoro, mono-chloro, mono-bromo and mono-iodo analogs 54-56, 58-62. The ortho-methoxy analog 63, and the two dimethoxy analogs 64 and 65 were also prepared. The 5-fluoro- and 7-fluoro precursor's 66-67 and 71-72 were used to generate analogs 68-70 and 73-74, respectively. Examples with the oxygen atom within benzofuran replaced with a nitrogen atom (i.e. indole related series) 75-77 were also prepared. Compound 79, the dichloro analog of 7, was prepared. To further probe the importance of the phenol functionality, dimethyl 81 and 82, and di-tert-butyl analog 84 were prepared. Compound 85, the methoxy analog of 7, was prepared to further compare the importance of the phenolic functionality. A few butyl analogs, 86-88, were prepared to illustrate the importance of the alkyl chain (i.e. ethyl versus butyl). Lastly, a deuterated analog 89 was prepared and used as an internal standard (IS) for the in vivo sample analysis.

Functional Analysis Via Oocytes Expressing hURAT1

Sodium pyruvate, collagenase type I from *Clostridium histolyticum* and sodium dodecyl sulfate (SDS) were obtained from Sigma-Aldrich Chemical Co. (St. Louis, Mo., USA). [$^{14}$C]Urate (55 mCi/mmol) was purchased from Moravek (Brea, Calif.). Gentamicin sulfate and other chemicals for solution preparation were purchased from Wako Pure Chemical Industries, Ltd. (Osaka, Japan). N-(2-hydroxyethyl)piperazine-N'-(2-ethane sulfonic acid) (HEPES) was purchased from Dojindo Laboratories (Kumamoto, Japan).

cRNA synthesis and oocyte injection. The hURATv1 (pCMV6-XL5) plasmids were linearized with XbaI and hURAT2 (pCMV-SPORT6) plasmids were linearized with XhoI. The cRNAs were synthesized in vitro with T7 RNA polymerase (for hURATv1) or SP6 RNA polymerase (for hURAT2) using mMessage mMachine® High yield capped RNA transcription kit (Ambion, Austin, Tex., USA). The polyadenylation of cRNA at 3'-end was performed using poly(A) tailing kit (Ambion, Austin, Tex., USA). Female *Xenopus* frogs (African clawed frogs; 95-120 g) were purchased from Sato Zoushoku (Chiba, Japan) and nurtured in tap water (19±3° C.). Oocytes (1.23±0.10 mg/oocyte) isolated from *Xenopus laevis* were defolliculated with 1.0 mg/ml collagenase in Ca$^{2+}$-free solution (96.0 mM NaCl, 2.0 mM KCl, 1.0 mM MgCl$_2$.6H$_2$O and 5.0 mM HEPES, pH 7.5) at 25+2° C. for 2.0 h. The oocytes were washed in Ca$^{2+}$-free solution and transferred to ND96 solution (96.0 mM NaCl, 2.0 mM KCl, 1.0 mM CaCl$_2$, 1.0 mM MgCl$_2$.6H$_2$O and 5.0 mM HEPES, pH 7.5). Defolliculated *Xenopus* oocytes (stage 1V and V) were injected with 25 ng of capped cRNA and incubated at 18° C. for 2-3 days in ND96 solution containing gentamicin (50 μg/ml) and 2.5 mM sodium pyruvate.

Inhibition study. After incubation of cRNA-injected oocytes (2-3 days), uptake experiments were performed at room temperature in ND96 solution. The uptake experiments were initiated by replacing the initial bath solutions with uptake solutions containing radiolabeled [$^{14}$C]urate (10 μM for hURAT1, 15 μM for hURATv1 and 30 μM for hURAT2) with or without test compound. The uptake was terminated by washing the oocytes with ice-cold uptake solution (5 times @ 1.0 ml each) after 60 min of incubation. The oocytes were solubilized with 5% (w/v) SDS and the radioactivity content determined using liquid scintillation counter (Aloka 3100; Aloka Co., Ltd. Tokyo, Japan). The urate uptake by non-injected (control) oocytes was subtracted from oocytes expressing hURAT1, hURATv1 or hURAT2. The data are presented and reported as the % inhibition. The IC$_{50}$ data were conducted using different compound concentrations.

Part Two: Inhibitor Studies

We have previously used the *Xenopus* oocyte expression system which has been a very useful single cell in vitro tool to probe drug molecules and their interactions with specific transporter proteins (Pombrio et al, 2001; Jutabha et al, 2010; Ohtsu et al, 2007). We have successfully incorporated functional hURAT1, hURAT2, or hURATv1 into oocytes. Summarized in FIG. 15, we tested 5, 7, 8 and 12-50 via hURAT1 expressing oocytes. We conducted a general screen where $^{14}$C-uric acid (10.0 viM) and test compound (50 µM) were placed in the extracellular fluid. Radioactivity inside the oocyte was analyzed after 60 min. Except probenecid 5, when the initial screen using 50 µM test compound produced >60% inhibition, we performed additional experiments with varying concentrations (i.e. 5, 10, 50, 100, 500 nM, and 5, 10 and 50 µM) of the test compound. The data were used to produce $IC_{50}$ values, concentration of compound reducing $^{14}$C-uric acid uptake in hURAT1 expressing oocytes by 50% relative to control oocyte experiments. The $IC_{50}$ values were generated using a sigmoidal dose-response (variable slope) relationship.

We probed the structure-activity relationship of benzbromarone-related compounds. The data in FIG. 15 illustrate that 7 has very potent hURAT1 inhibitor potential. The 6-hydroxy-metabolite 8 was a weaker inhibitor than 7; an $IC_{50}$ 138 nM versus 26 nM, respectively. These data are comparable to MDCK-hURAT1 data where 200 nM and 35 nM (5.7-fold difference) were reported, respectively (Endou and Olkawa, 2009). Compound 12 with one methoxy group in the C-Ring and dimethoxy analogs (14-20, FIG. 5) at 50 µM produced weak-to-no $^{14}$C-urate transport inhibition. Two di-methoxy-compounds (14 and 19) displayed weak inhibition, both contain the C-Ring connected at benzofuran position three. Comparing 12 to benzarone 13 (FIG. 5), the importance for the phenolic —OH in the C-Ring is clear with $IC_{50}$ changing from >50 µM to 2.8 µM. Halogenation of 13 to give 7 results in an inhibitor with very potent activity, a low nano-molar hURAT1 inhibitor (i.e. $IC_{50}$<50 nM).

Metabolite 8 was prepared from 17; C-Ring deprotection to 30 (FIG. 6) followed by halogenation to 45 (FIG. 7) and deprotection. Compound 30 versus B-Ring phenol 31 illustrates the more potent C-Ring phenol inhibitor trend (>50 µM versus 3.9 µM). Comparing 30 and 32 ($IC_{50}$ of 3.9 µM versus 1.1 µM) illustrates a methoxy on B-Ring analog is less potent (higher $IC_{50}$ value) than the diphenol analog. The 6-methoxy regioisomers such as 18, compared to demethoxylated analogs 33, 34 and 35, displayed an inhibitory trend: (18, di-MeO<34, C-Ring —OMe<35, di-OH<33, B-ring —OMe). The 5-methoxy series (FIG. 6, FIG. 15) allowed cleavage of 14 to produce 21, 22, and 23; while 16 produced 27, 28 and 29. The 3-yl series also illustrates the C-Ring phenol ($IC_{50}$ 22 >>21 =23) inhibitor activity.

Compound 15 was deprotected to produce 24, 25 and 26 (FIG. 6); whereas 20 produced 37 and 38 and cleavage of 19 gave 36. Comparing 27-29 (FIG. 15) also illustrates the importance of the C-Ring phenol and that a diphenol may or may not be detrimental to inhibitor activity. Compounds 39-50 (FIG. 7 and FIG. 15) were all brominated analogs, with either one 50, two (40-45, 48 and 49), or three (46 and 47) bromine atoms. Compounds with a methoxy on the B-Ring, and dibromo-phenol functionality on the C-Ring, were more potent inhibitors when C-Ring was connected to A-Ring (39 and 45) than versus B-Ring (41 and 43). The general decreased inhibitor potency trend (i.e. increased $IC_{50}$) was present when 39 and 45 (C-Ring connected to A-Ring analogs) were demethoxylated to 40 and 8, respectively. Conversely, more potent inhibitors (i.e. lower $IC_{50}$) were produced when 41 and 43 (C-Ring connected to B-Ring analogs) were demethoxylated to 42 and 44, respectively. Therefore, a vast amount of data supports the importance of the C-Ring dibromo-phenol; 43 versus 44 (1.44 µM versus 287 nM) shows an example where B-Ring —OH enhanced inhibitor activity.

Depicted in FIG. 8, and summarized by the in vitro data in FIG. 16 and FIG. 17, additional compounds were prepared and illustrate structural requirements for potent inhibitors. The data in FIG. 16 illustrate electronic and steric effects (i.e. —F versus —Cl versus —Br alpha to the phenol) while the data in FIG. 17 demonstrate how our in vitro testing methods generate a procedure to afford preferred compounds (i.e. using the testing procedures described, compounds with a combined % inhibition of ≥160% for hURAT1, hURAT2, and hURATv1 are preferred compounds). However, it will be understood that these examples are included merely for purposes of illustration and are not intended to limit the scope of the invention; for example, while compound 85 does not have a combined % inhibition of ≥160% it may still be a useful pro-drug where the methoxy functionality is metabolized via CYP's to afford potent compound 7.

In addition to the in vitro testing methodology, the invention can be further illustrated by the following in vivo examples where compounds are illustrated to be orally bio-available via administration to male Sprague-Dawley rats. The in-life portion was conducted at East Tennessee State University—Quillen College of Medicine—in an AAALAC accredited facility. All procedures were reviewed and approved by the ETSU Committee on Animal Care. Male Sprague-Dawley rats were purchased from Harlan World Headquarters (Indianapolis, Ind., USA). Animals were housed in groups of three at 22.2±1.1° C. and 55±15% humidity with 12 h dark light cycles. Dosing occurred 2.0-3.0 h after the beginning of a light cycle. All animals had free access to water, fasted 14-16 h prior to dosing in cages with bedding; food was returned 4 h post-dose.

To prepare the formulations, compounds were weighed and CMC was added and mixed. To help remove clumps or aggregates that might have formed while mixing, the material was removed and passed through a 35-mesh sieve screen. After additional mixing, the resulting blend contained ~20 weight percent of the corresponding compound. Using a filling funnel, formulations were encapsulated into hard shell Torpac Lock ring gel (size 9) capsules (Torpac, USA). Rats were dosed orally using a Torpac capsule syringe (Torpac, USA) followed by an immediate water (500 µL) bolus. Using tail-vein collection (i.e. the anterior portion was transected, 2-3 mm), blood samples (125 µL) were collected using mini-capillary blood collection tubes containing EDTA di-potassium salt (SAFE-T-FILL®; RAM Scientific Inc., Yonkers, N.Y., USA). Immediately after filling, individual sample tubes were mixed and stored on dry ice and kept frozen (−80±10° C.) until sample preparation and subsequent LC/MS-MS analysis. Control rat blood collected with K2 EDTA (Lot #163458) was purchased from Bioreclamation LLC (Westbury, N.Y.). The control blood was used to prepare standard curves and used to determine in vivo blood concentration data. Compound 89 was used as an internal standard (IS). Standard curves (SC) were prepared using addition and thorough mixing of various aqueous solutions of the compounds (50 µL) with blood (950 µL). SC were immediately frozen (−80±10° C.). SC were extracted and processed in an analogous fashion as the in vivo samples as follows: an extraction solution containing IS was freshly prepared in a 100 mL volumetric flask containing 4:1 (1:1 acetonitrile:methanol) and water (v/v). In individual sets, the PK sample tubes were removed from the freezer (−80±10° C.) and allowed to thaw on ice (30 min). The tubes were vortexed (3-5 s) and then extraction solution (250 µL) was added, vortex mixed (5 s), sat at RT for 5 min, vortex mixed a 2″ time (5 s), and then centrifuged at 10,000 rpm (5 min) using an Eppendorf minispin centrifuge (Hamburg, Germany). The supernatants were transferred into individual wells of a 96-well plate. The 96-well plate was placed into the LEAP auto-sampler cool-stack (6.0±0.1° C.) and analyzed via LC/MS/MS. An Applied Biosystems Sciex 4000® (Applied Biosystems; Foster City, Calif.) equipped with a Shimadzu HPLC (Shimadzu Scientific Instruments, Inc.; Columbia, Md.) and Leap auto-sampler (LEAP Technologies; Carrboro, N.C.) was used. Liquid chromatography employed an Agilent Technologies, Zorbax extended-C18 50×4.6 mm, 5 micron column at 40° C. with a flow-rate of 0.4 mL/min. The mobile phase consisted of A: 10 mM ammonium acetate, 0.1% formic acid in water, and B: 50:50 ACN:MeOH. Compounds were monitored via electrospray ionization positive ion mode (ESI+) using conditions previously denoted for the individual compounds. The in vivo data have been summarized in FIGS. 9-14 and illustrate that even without the presence of solubilizing agents, these compounds are bio-available and illustrate oral administration proof-of-concept for the development of novel compounds designed for their Uricosuric action.

REFERENCES

Anzai, N.; Kanai, Y.; Endou, H. New insights into renal transport of urate. *Curr. Opin. Rheumatol.* 2007, 19, 151-157.

Anzai, N.; Ichida, K.; Jutabha, P.; Kimura, T.; Babu, E.; Jin, C. J.; Srivastava, S.; Kitamura, K.; Hisatome, I.; Endou, H.; Sakurai, H. Plasma urate level is directly regulated by a voltage-driven urate efflux transporter URATv1 (SLC2A9) in humans. *J. Biol. Chem.* 2008, 283, 26834-26838.

Anzai, N.; Jutabha, P.; Endou, H. Renal Solute Transporters and Their Relevance to Serum Urate Disorder. *Curr. Hypertens. Rev.* 2010, 6, 148-154.

Becker, M. A.; Jolly, M. Hyperuricemia and associated diseases. *Rheum. Dis. Clin. N Am.* 2006, 32, 275-293.

Caulfield, M. J.; Munroe, P. B.; O'Neill, D.; Witkowska, K.; Charchar, F. J.; Doblado, M.; Evans, S.; Eyheramendy, S.; Onipinla, A.; Howard, P.; Shaw-Hawkins, S.; Dobson, R. J.; Wallace, C.; Newhouse, S. J.; Brown, M.; Connell, J. M.; Dominiczak, A.; Farrall, M.; Lathrop, G. M.; Samani, N.J.; Kumari, M.; Marmot, M.; Brunner, E.; Chambers, J.; Elliott, P.; Kooner, J.; Laan, M.; Org, E.; Veldre, G.; Viigimaa, M.; Cappuccio, F. P.; Ji, C.; Lacone, R.; Strazzullo, P.; Moley, K. H.; Cheeseman, C. SLC2A9 is a high-capacity urate transporter in humans. *PLoS Med.* 2008, 5, e197.

Endou, H.; and Olkawa, T. Medicinal Compositions Containing 6-Hydroxybenzbromarone or Salts Thereof. U.S. Pat. No. 7,521,570 B2, 2009.

Enomoto, A.; Kimura, H.; Chairoungdua, A.; Shigeta, Y.; Jutabha, P.; Cha, S. H.; Hosoyamada, M.; Takeda, M.; Sekine, T.; Igarashi, T.; Matsuo, H.; Kikuchi, Y.; Oda, T.; Ichida, K.; Hosoya, T.; Shimokata, K.; Niwa, T.; Kanai, Y.; Endou, H. Molecular identification of a renal urate anion exchanger that regulates blood urate levels. *Nature* 2002, 417, 447-452.

Feig, D. I.; Kang, D. H.; Johnson, R. J. Uric acid and cardiovascular risk. *N. Engl. J. Med.* 2008, 359, 1811-1821.

Jutabha, P.; Anzai, N.; Kitamura, K.; Taniguchi, A.; Kaneko, S.; Yan, K.; Yamada, H.; Shimada, H.; Kimura, T.; Katada, T.; Fukutomi, T.; Tomita, K.; Urano, W.; Yamanaka, H.; Seki, G.; Fujita, T.; Moriyama, Y.; Yamada, A.; Uchida, S.; Wempe, M. F.; Endou, H.; Sakurai, H. Human sodium-phosphate transporter 4 (hNPT4/SLC17A3) as a common renal secretory pathway for drugs and urate *J. Biol. Chem.* 2010, 285, 35123-35132.

Jutabha, P.; Wempe, M. F.; Anzai, N.; Otomo, J.; Kadota, T.; Endou, H. *Xenopus laevis* oocytes expressing human P-glycoprotein: Probing trans- and cis-inhibitory effects on [$^3$H]vinblastine and [$^3$H]digoxin efflux. *Pharmacol. Res.* 2010, 61 76-84.

Kutzing, M. K.; Firestein, B. L. Altered uric acid levels and disease states. *J. Pharmacol. Exp. Ther.* 2008, 324, 1-7.

Lee, M. H.; Graham, G. G.; Williams, K. M.; Day, R. O. A benefit-risk assessment of benzbromarone in the treatment of gout. Was its withdrawal from the market in the best interest of patients? *Drug Saf* 2008, 31, 643-665.

Lemke, T. L.; Williams, D. A. Foye's Principles of Medicinal Chemistry, 6$^{th}$ Edition Lippincott Williams & Wilkins 2008, 998-1001.

McDonald, M. G.; and Rettie, A. E. Sequential Metabolism and Bioactivation of the Hepatotoxin Benzbromarone Formation of Glutathione Adducts from a Catechol Intermediate. *Chem. Res. Toxicol.* 2007, 20, 1833-1842.

Mount, D. B.; Kwon, C. Y.; and Zandi-Nejad, K. Renal urate transport. *Rheum. Dis. Clin. North Am.* 2006, 32, 313-331.

Neogi, T. Clinical Practice. Gout. *New England J. Med.* 2011, 364, 443-452.

Ohtsu, N.; Otomo, J.; Anzai, N.; Sakata, T.; Jutabha, P.; Narikawa, S.; Kadota, T.; Endou, H. Development of the alternative method for renal drug excretion using *Xenopus* oocyte expression system combined with a high throughput method, OOCYTEXPRESS®, AATEX 2007, 14, S1669-671.

Pombrio, J. M.; Giangreco, A.; Li, L.; Wempe, M. F.; Anders, M. W.; Sweet, D. H.; Pritchard, J. B.; Ballatori, N. Mercapturic acids (N-acetylcysteine S-conjugates) as endogenous substrates for the renal organic anion transporter-1, *Mol. Pharm.* 2001, 60, 1091-1099.

Saag, K. G.; and Choi, H. Epidemiology, risk factors, and lifestyle modifications for gout *Arthritis Research and Therapy* 2006, 8 (Suppl. 1:S2).

Sekine, T.; Watanabe, N.; Hosoyamada, M.; Kanai, Y.; Endou, H. Expression Cloning and Characterization of a Novel Multispecific Organic Anion Transporter. *J. Biol. Chem.* 1997, 272, 18526-18529.

Shin, H. J.; Takeda, M.; Enomoto, A.; Fujimura, M.; Miyazaki, H.; Anazi, N.; Endou, H. Interactions of urate transporter URAT1 in human kidney with uricosuric drugs. *Nephrology* 2011, 16, 156-162.

Roch-Ramel, F.; and Guisan, B. Renal Transport of Urate in Humans. *News Physiol. Sci.* 1999, 14, 80-84.

Zubay, G. L. Biochemistry. 4$^{th}$ Edition. Wm. C. Brown Publishers, Dubuque, Iowa. 1998, Chapter 26, 629-665.

We claim:

1. A compound represented by the general Formula III:

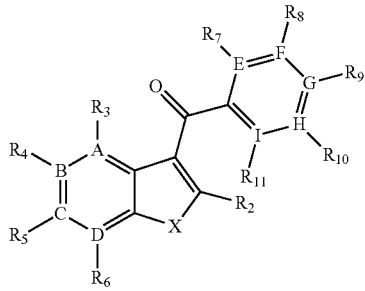

Formula III a pharmaceutically acceptable salt or ester thereof, a solvate thereof, a deuterated or radio-labeled analog thereof, and mixtures of any of the foregoing, wherein:
A-I are individually carbon;
X=—O—;
$R_2$ is methyl, ethyl, trifluoromethyl, or CO—$CH_3$;
$R_3$, $R_6$, $R_7$, and $R_{11}$ are —H;
$R_4$ is —OMe, —OEt, —F, —$CF_3$, or —H;
$R_5$ is —OMe, —OEt, —O—CO—$CH_3$, —H, —F, —$CF_3$, or —O—$CF_3$;
$R_8$ and $R_{10}$ are —Br;
$R_9$ is —OH, and
wherein at least one of $R_4$ and $R_5$ is fluorine.

2. A composition comprising at least one compound of claim 1, wherein the compound is present in an amount of at least 0.01% by weight to about 5.0% by weight.

3. A composition comprising at least one compound of 1, wherein the compound is present in an amount of from about 5.0% to about 95% by weight.

4. A kit comprising:
a composition comprising at least one compound of claim 1,
instructions for administrating the composition comprising at least one compound of claim 1 to a human or mammal.

5. A container, wherein the contents of the container comprise:
at least one compound of claim 1,
wherein the container contains, is labeled, or is otherwise accompanied by instructions for administration to a human or mammal in a manner that results in interacting with selected cells, tissues, or organs for a selected period of time.

6. The compound of claim 1, wherein $R_4$ is fluorine and $R_5$ is H, or $R_4$ is H and $R_5$ is fluorine, or $R_4$ and $R_5$ are fluorine.

7. The compound of claim 6, wherein $R_2$ is methyl or ethyl.

8. The compound of claim 1, wherein
$R_2$ is methyl or ethyl, and
$R_5$ is —H.

9. The compound of claim 8, wherein
$R_2$ is ethyl.

10. The compound of claim 1, wherein the compound is selected from (3,5-dibromo-4-hydroxyphenyl)(2-ethyl-6-fluorobenzofuran-3-yl)methanon, (3,5-dibromo-4-hydroxyphenyl)(2-ethyl-5-fluorobenzofuran-3-yl)methanone, (3,5-dibromo-4-hydroxyphenyl)(2-ethyl-5,6-difluorobenzofuran-3-yl)methanone, (3,5-dibromo-4-hydroxyphenyl)(2-methyl-6-fluorobenzofuran-3-yl)methanone, (3,5-dibromo-4-hydroxyphenyl)(2-methyl-5-fluorobenzofuran-3-yl)methanone, or (3,5-dibromo-4-hydroxyphenyl)(2-methyl-5,6-difluorobenzofuran-3-yl)methanone.

* * * * *